(12) United States Patent
Gilbert et al.

(10) Patent No.: US 9,416,129 B2
(45) Date of Patent: Aug. 16, 2016

(54) TRICYCLIC SUBSTITUTED THIADIAZINE DIOXIDE COMPOUNDS AS BACE INHIBITORS, COMPOSITIONS AND THEIR USE

(71) Applicant: Merck Sharp & Dohme Corp., Rahway, NJ (US)

(72) Inventors: Eric J. Gilbert, Scotch Plains, NJ (US); Jared N. Cumming, Garwood, NJ (US); Andrew W. Stamford, Chatham, NJ (US); Younong Yu, East Brunswick, NJ (US); Jack D. Scott, Scotch Plains, NJ (US); Ulrich Iserloh, Hoboken, NJ (US); Lingyan Wang, East Brunswick, NJ (US); John P. Caldwell, Ringwood, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/433,298

(22) PCT Filed: Oct. 14, 2013

(86) PCT No.: PCT/US2013/064799
§ 371 (c)(1),
(2) Date: Apr. 2, 2015

(87) PCT Pub. No.: WO2014/062553
PCT Pub. Date: Apr. 24, 2014

(65) Prior Publication Data
US 2015/0284379 A1    Oct. 8, 2015

Related U.S. Application Data

(60) Provisional application No. 61/779,366, filed on Mar. 13, 2013, provisional application No. 61/714,969, filed on Oct. 17, 2012.

(51) Int. Cl.
| | | |
|---|---|---|
| *C07D 417/14* | (2006.01) | |
| *C07D 417/10* | (2006.01) | |
| *C07D 417/04* | (2006.01) | |
| *A61K 31/549* | (2006.01) | |
| *A61K 45/06* | (2006.01) | |
| *C07D 495/04* | (2006.01) | |

(52) U.S. Cl.
CPC ............ *C07D 417/14* (2013.01); *A61K 31/549* (2013.01); *A61K 45/06* (2013.01); *C07D 417/10* (2013.01); *C07D 495/04* (2013.01)

(58) Field of Classification Search
CPC .. C07D 417/14; C07D 417/10; C07D 417/04; A61K 31/549; A61K 45/06
USPC .......................................... 544/8; 514/222.5
See application file for complete search history.

(56) References Cited

U.S. PATENT DOCUMENTS

| | | |
|---|---|---|
| 3,423,408 A | 1/1969 | Pfirmann et al. |
| 5,534,520 A | 7/1996 | Fisher et al. |
| 5,889,002 A | 3/1999 | Nielsen et al. |
| 6,225,310 B1 | 5/2001 | Nielsen et al. |
| 7,648,983 B2 | 1/2010 | Audia et al. |
| 2007/0287692 A1 | 12/2007 | Wu et al. |
| 2008/0200445 A1 | 8/2008 | Zhu et al. |
| 2010/0075957 A1 | 3/2010 | Tamura et al. |

(Continued)

FOREIGN PATENT DOCUMENTS

| | | |
|---|---|---|
| EP | 1942105 | 7/2008 |
| WO | 2007049532 A1 | 5/2007 |

(Continued)

OTHER PUBLICATIONS

Esteban, et al., "New 1,2,6-Thiadiazine Dioxide Acyclonucleaosides: Synthesis and Antiviral Evaluation", Bioorganic & Medicinal Chemistry, 1995, p. 1527-1535, vol. 3, No. 11.

(Continued)

*Primary Examiner* — Kahsay Habte
(74) *Attorney, Agent, or Firm* — Keith D. MacMillan; John C. Todaro

(57) ABSTRACT

In its many embodiments, the present invention provides certain iminothiazine dioxide compounds, including compounds Formula (I): (I) and tautomers and stereoisomers thereof, and pharmaceutically acceptable salts of said compounds, said tautomers and said stereoisomers, wherein the middle ring (referred to herein as "ring B") of the tricyclic substituent is an optionally substituted 6-membered ring, and each of the remaining variables shown in the formula are as defined herein. The novel compounds of the invention are useful as BACE inhibitors and/or for the treatment and prevention of various pathologies related thereto. Pharmaceutical compositions comprising one or more such compounds (alone and in combination with one or more other active agents), and methods for their preparation and use, including Alzheimer's disease, are also disclosed.

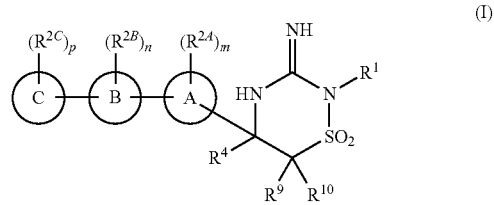

(I)

13 Claims, No Drawings

(56) References Cited

U.S. PATENT DOCUMENTS

| | | | |
|---|---|---|---|
| 2012/0183563 A1 | 7/2012 | Scott et al. |
| 2012/0189642 A1 | 7/2012 | Scott et al. |
| 2012/0258961 A1 | 10/2012 | Suzuki et al. |
| 2015/0274716 A1 | 10/2015 | Gilbert et al. |
| 2015/0284379 A1 | 10/2015 | Gilbert et al. |
| 2015/0353516 A1 | 12/2015 | Cumming et al. |

FOREIGN PATENT DOCUMENTS

| | | | |
|---|---|---|---|
| WO | 2008133274 | | 6/2008 |
| WO | 2008103351 | | 8/2008 |
| WO | 2011044181 | | 4/2011 |
| WO | 2011044184 | | 4/2011 |
| WO | 2011044185 | | 4/2011 |
| WO | 2011044187 | | 4/2011 |
| WO | 2011154374 | | 12/2011 |
| WO | 2011154431 | | 12/2011 |
| WO | 2012138734 | A1 | 10/2012 |
| WO | 2014099768 | A1 | 6/2014 |
| WO | 2014150331 | A1 | 9/2014 |
| WO | 2014150340 | A1 | 9/2014 |
| WO | 2015094930 | A1 | 6/2015 |

OTHER PUBLICATIONS

Getchell, et al., 3-Nitrotyrosine immunoreactivity in olfactory receptor neurons of patients with Alzheimer's disease: implications for impaired odor sensitivity, Neurobiology of Aging 24 (2003) 663-673., accepted Oct. 8, 2002, pp. 663-673.

Guo, et al., Targeting Amyloid-B in Glaucoma Treatment, pp. 13444-13449, PNAS, Aug. 14, 2007, vol. 104,No. 33.

Loane, et al., Amyloid Precursor Protein Secretases as Therapeutic Targets for Traumatic Brain Injury, Nature Medicine, Advance Online Publication, Received Aug. 27, 2008; accepted Feb. 18, 2009; published online Mar. 15, 2009; doi:10.1038/nm.1940, pp. 1-3.

Luo, et al., mice deficient in BACE1, the Alzheimer's B-secretase, have normal phenotype and abolished B-amyloid, Nature Neuroscience, vol. 4, No. 3, Mar. 2001.

McConlogue, et al., Partial reduction of BACE1 as dramatic effects on Alzheimer's plaque and synaptic pathology in APP transgenic mice, J. Biological Chem., vol. 282, No. 36, pp. 26326-26334, Sep. 7, 2007.

Ohno, et al., BACE1 deficiency rescues memory deficits and Cholinergic function in a mouse model of Alzheimer's disease, Neuron, vol. 41, 27-33, Jan. 8, 2004.

Ohno, et al.BACE1 gene deletion prevents neuron loss and memory deficits in 5XFAD APP/PS1 transgenic mice, Neurobiology of disease 26 (2006), pp. 134-145.

Osherovich, L. AB's Dry (AMD) Humor, SciBX 4(26); doi:10.1038/scibx.2011.727, Published online Jun. 30, 2011.

Probst, et al., Small-molecule BACE1 inhibitors:a patent literature review, Expert Opinion on Therapeutic Patents, (2006-2011), 2012, 22(5):511-540.

Roberds, et al., BACE knockout mice are healthy despite lacking the primary B-secretase activity in the brain: implications for Alzheimer's disease therapeutics, Human Mol. Genetics, vol. 10, No. 12, pp. 1317-1324. Apr. 3, 2004.

Scott, et al., "Novel Imino Pyrimidinone B-Secretase (BACE1) Inhibitors. P1 Thiophenes", Poster presentation, American Chemical Society, Sprint 2011.

Solloway, et al., A randomized, double-blind, placebo-controlled clinical trial of intravenous bapineuzumab in patients with mild-to-moderate Alzheimer's disease who are alipoprotein E4 non-carriers, European Federation of Neurological Societies, Stockholm, Sweden, Sep. 12, 2012.

Southan, BACE2 as a New Diabetes Target: a patent review 2010-2012, Expert Opinion on Therapeutic Patents, 2013, Informa UK, Ltd., ISSN 1354-3776, e-1744-7674.

Stamford, et al., Discovery of an Orally Available, Brain Penetrant BACE1 Inhibitor That Affords Robust CNS Aβ Reduction, ACS Med. Chem. Lett. Jul. 12, 2012, 3, 897-902.

Stamford, et al., Inhibitors of BACE for treating Alzheimer's disease: a fragment-based drug discovery story, Current Opinion in Chemical Biology; v:17 i:3 p:320-328; Jun. 2013 Elsevier.

Stamford, et al., "Fragment-based discovery of BACE1 inhibitors, Potential disease-modifying agents for the treatment of Alzheimer's disease", Slide Presentation R. Bryan Miller Symposium, UC Davis, Mar. 7-8, 2013.

Weiner, Further insights into Alzheimer disease pathogenesis, Weiner, M. W. Nat. Rev. Neurol. 9, 65-66 (2013); published online Jan. 22, 2013.

Wyss DF, et al., Combining NMR and X-ray crystallography in fragment-based drug discovery: discovery of highly potent and selective BACE-1 inhibitors. Top Curr Chem. 2012;317:83-114. doi: 10.1007/128_2011_183.

TRICYCLIC SUBSTITUTED THIADIAZINE DIOXIDE COMPOUNDS AS BACE INHIBITORS, COMPOSITIONS AND THEIR USE

FIELD OF THE INVENTION

This invention provides certain tricyclic substituted thiadiazine dioxide compounds in which the middle ring (referred to herein as "ring B") of the tricyclic substituent is an optionally substituted 6-membered ring, and compositions comprising these compounds, as inhibitors of BACE, which may be useful for treating or preventing pathologies related thereto.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis ((β2 microglobulins and complications arising therefrom), neurodegenerative diseases such as scrapie, bovine spongiform encephalitis, Creutzfeld-Jakob disease, traumatic brain injury and the like.

Aβ peptides are short peptides which are made from the proteolytic break-down of the transmembrane protein called amyloid precursor protein ("APP"). Aβ peptides are made from the cleavage of APP by β-secretase activity at a position near the N-terminus of Aβ, and by gamma-secretase activity at a position near the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of Aβ by β-secretase activity. The inhibition of BACE-1 has been shown to inhibit the production of Aβ.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and gamma-secretase activity, can form tertiary structures that aggregate to form amyloid fibrils. Aβ peptides have also been shown to form Aβ oligomers (sometimes referred to as "Aβ aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ, Aβ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS 1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuronal cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of Aβ-driven AD-like pathology, making β-secretase a target for therapeutic intervention in AD. Ohno et al. Neurobiology of Disease, No. 26 (2007), 134-145, report that genetic deletion of BACE-1 in 5XFAD mice abrogates Aβ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that Aβ is ultimately responsible for neuron death in AD and concludes that BACE-1 inhibition has been validated as an approach for the treatment of AD. Roberds et al., Human Mol. Genetics, 2001, Vol. 10, No. 12, 1317-1324, established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation.

More recently, Jonsson, et al. have reported in Nature, Vol. 488, pp. 96-99 (August 2012), that a coding mutation (A673T) in the APP gene protects against Alzheimer's disease and cognitive decline in the elderly without Alzheimer's disease. More specifically, the A allele of rs63750847, a single nucleotide polymorphism (SNP), results in an alanine to threonine substitution at position 673 in APP (A673T). This SNP was found to be significantly more common in a healthy elderly control group than in an Alzheimer's disease group. The A673T substitution is adjacent to the aspartyl protease beta-site in APP, and results in an approximately 40% reduction in the formation of amyloidogenic peptides in a heterologous cell expression system in vitro. Jonsson, et al. report that an APP-derived peptide substrate containing the A673T mutation is processed 50% less efficiently by purified human BACE1 enzyme when compared to a wild-type peptide. Jonsson et al. indicate that the strong protective effect of the APP-A673T substitution against Alzheimer's disease provides proof of principle for the hypothesis that reducing the beta-cleavage of APP may protect against the disease.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., Ann NY Acad Sci 2002; 855:723-31; Crino P B, Martin J A, Hill W D, et al., Ann Otol Rhinol Laryngol, 1995; 104:655-61; Davies D C, et al., Neurobiol Aging, 1993; 14:353-7; Devanand D P, et al., Am J Psychiatr, 2000; 157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and IAPP, but lacking in the other endocrine and exocrine cell types. Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"), Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, Loane, et al. report the targeting of amyloid precursor protein secretases as therapeutic targets for traumatic brain injury. (Loane et al., "Amyloid precursor protein secretases as therapeutic targets for traumatic brain injury", Nature Medicine, Advance Online Publication, published online Mar. 15, 2009.) Still other diverse pathologies characterized by the inappropriate formation and deposition of Aβ or fragments thereof, and/or by the presence of amyloid fibrils, and/or for which inhibitor(s) of BACE-1 is expected to be of therapeutic value are discussed further hereinbelow.

The therapeutic potential of inhibiting the deposition of Aβ has motivated many groups to characterize BACE and to identify inhibitors of BACE-1 and/or BACE-2 and of other secretase enzyme inhibitors. Examples from the patent literature are growing and include WO2006009653, WO2007005404, WO2007005366, WO2007038271, WO2007016012, US2005/0282826, US2007072925, WO2007149033, WO2007145568, WO2007145569, WO2007145570, WO2007145571, WO2007114771, US20070299087, WO2005/016876, WO2005/014540, WO2005/058311, WO2006/065277, WO2006/014762, WO2006/014944, WO2006/138195, WO2006/138264, WO2006/138192, WO2006/138217, WO2007/050721, WO2007/053506, WO2007/146225, WO2006/138230, WO2006/138265, WO2006/138266, WO2007/053506, WO2007/146225, WO2008/073365, WO2008/073370, WO2008/103351, US2009/041201, US2009/041202, WO2010/047372, WO2011/044181, WO2011/044185, WO2011/044187, PCT/US10/51557, PCT/US12/31783, PCT/CN2012/000497, and PCT/US12/051687.

SUMMARY OF THE INVENTION

The present invention provides certain tricyclic substituted thiadiazine dioxide compounds in which the middle ring ("ring B") of the tricyclic substituent is an optionally substituted 6-membered ring, which are collectively or individually referred to herein as "compound(s) of the invention", as described herein. The compounds of the invention are useful as inhibitors of BACE-1 and/or BACE-2.

In one embodiment, the compounds of the invention have the structural Formula (I):

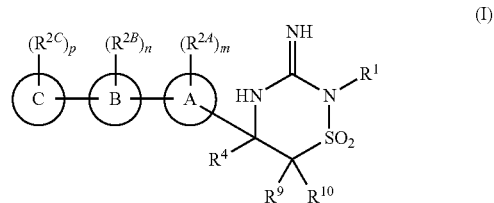

or a tautomer thereof having the structural Formula (I'):

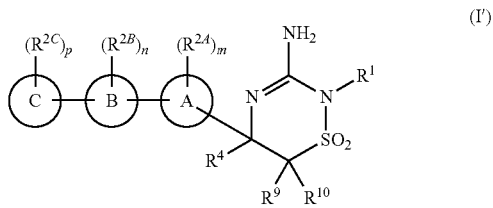

or pharmaceutically acceptable salt thereof, wherein:

$R^1$ is selected from the group consisting of H, lower alkyl, lower heteroalkyl, lower cycloalkyl, and -(lower alkyl)-(lower cycloalkyl) wherein each said lower alkyl, lower heteroalkyl, lower cycloalkyl, and -(lower alkyl)-(lower cycloalkyl) is optionally substituted with fluoro;

ring A is selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

each $R^{2A}$ (when present) is independently selected from the group consisting of: halo, oxo, —OH, —CN, —$SF_5$, —$OSF_5$, —$NO_2$, —$Si(R^5)_3$, —$N(R^6)_2$, —$OR^6$, —$SR^6$, alkyl, haloalkyl, heteroalkyl, alkenyl, alkynyl, cycloalkyl, -alkyl-cycloalkyl, heterocycloalkyl, and -alkyl-heterocycloalkyl,
wherein said alkyl, haloalkyl, heteroalkyl, alkenyl, alkynyl, cycloalkyl, -alkyl-cycloalkyl, heterocycloalkyl, and -alkyl-heterocycloalkyl of $R^{2A}$ are each optionally unsubstituted or substituted with one or more groups independently selected from $R^8$;

m is 0 or more;

ring B is selected from the group consisting of a 6-membered aryl, 6-membered cycloalkyl, 6-membered cycloalkenyl, 6-membered heteroaryl, a 6-membered heterocycloalkyl, and a 6-membered heterocycloalkenyl ring, wherein each said heteroatom containing ring comprises from 1 to 4 ring heteroatoms independently selected from the group consisting of N, N-oxide, O, S, S(O), and $S(O)_2$;

each $R^{2B}$ (when present) is independently selected from the group consisting of halo, —CN, alkyl, cycloalkyl, -alkyl-cycloalkyl, heterocycloalkyl, heteroalkyl, haloalkyl —O-alkyl, —O-cycloalkyl, —O-alkyl-cycloalkyl, —O-heteroalkyl, and —O-haloalkyl;

n is 0 or more;

ring C is selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

each $R^{2C}$ (when present) is independently selected from the group consisting of: halo, oxo, —OH, —CN, —$SF_5$, —$OSF_5$, —$Si(R^5)_3$, —$N(R^6)_2$, —$NR^7C(O)R^6$, —$NR^7S(O)_2R^{12}$, —$NR^7S(O)_2N(R^6)_2$, —$NR^7C(O)N(R^6)_2$, —$NR^7C(O)OR^6$, —$C(O)R^6$, —$C(O)_2R^6$, —$C(O)N(R^6)_2$, —$S(O)R^{12}$, —$S(O)_2R^{12}$, —$S(O)_2N(R^6)_2$, —$OR^6$, —$SR^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl,
wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl of $R^{2C}$ are each optionally unsubstituted or substituted with one or more groups independently selected from $R^8$;

p is 0 or more;

$R^4$ is selected from the group consisting of lower alkyl and lower haloalkyl;

each $R^5$ (when present) is independently selected from the group consisting of alkyl, heteroalkyl, haloalkyl, cycloalkyl, and -alkyl-cycloalkyl;

each $R^6$ (when present) is independently selected from the group consisting of H, alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl,
wherein each said alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl of $R^6$ is unsubstituted or substituted with one or more groups independently selected from halo, —CN, —OH, lower alkyl, lower cycloalkyl, lower heteroalkyl, lower haloalkyl, lower —O-alkyl, lower —O-heteroalkyl, and lower —O-haloalkyl;

each $R^7$ (when present) is independently selected from the group consisting of H, alkyl, heteroalkyl, haloalkyl, cycloalkyl, -alkyl-cycloalkyl, aryl, -alkyl-aryl, heteroaryl, and -alkyl-heteroaryl,
wherein each said cycloalkyl, -alkyl-cycloalkyl, aryl, -alkyl-aryl, heteroaryl, and -alkyl-heteroaryl of $R^7$ is unsubstituted or substituted with one or more groups independently selected from halo, —CN, lower alkyl, lower cycloalkyl, lower heteroalkyl, lower haloalkyl, lower —O-alkyl, lower —O-heteroalkyl, and lower —O-haloalkyl;

each $R^8$ (when present) is independently selected from the group consisting of halo, oxo, —OH, —CN, —$SF_5$, —$OSF_5$, alkyl, —O-alkyl, haloalkyl, haloalkoxy, —$C(O)OR^{11}$, cycloalkyl, -alkyl-cycloalkyl, —O-cycloalkyl, —O-alkyl-cycloalkyl, —O-benzyl, heteroalkyl, —O-heteroalkyl, and -alkyl-OH;

$R^9$ is selected from the group consisting of H, halo, alkyl, cycloalkyl, haloalkyl, and heteroalkyl;

$R^{10}$ is selected from the group consisting of H, halo, alkyl, cycloalkyl, haloalkyl, and heteroalkyl;

$R^{11}$ (when present) is selected from the group consisting of H, lower alkyl, lower heteroalkyl, lower cycloalkyl, and -alkyl-(lower cycloalkyl); and each $R^{12}$ (when present) is independently selected from the group consisting of alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl,
wherein each said alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl of $R^{12}$ is unsubstituted or substituted with one or more groups independently selected from halo, —CN, —OH, lower alkyl, lower cycloalkyl, lower heteroalkyl, lower haloalkyl, lower —O-alkyl, lower —O-heteroalkyl, and lower —O-haloalkyl.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents, simultaneously or sequentially, suitable for treating the patient being treated.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I) or (IA).

In one embodiment, the compounds of the invention have the structural Formula (I) or (I') as described above.

In one embodiment, the compounds of the invention have the structural Formula (IA):

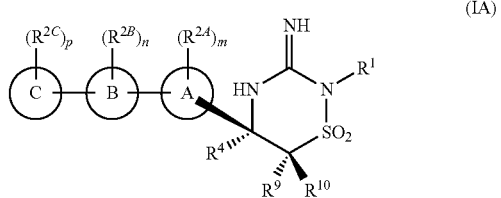

or a tautomer thereof having the structural Formula (IA'):

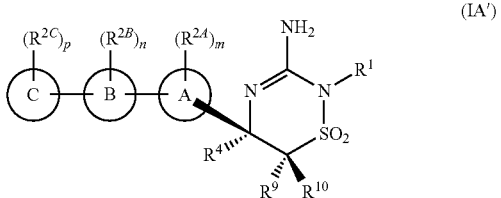

or a pharmaceutically acceptable salt thereof, wherein each variable is as described in Formula (I).

In one embodiment, in each of Formulas (I), (IA), and (IA'): $R^1$ is selected from the group consisting of H, lower alkyl, and cyclopropyl.

In one embodiment, in each of Formulas (I), (IA), and (IA'): $R^1$ is selected from the group consisting of H, methyl, ethyl, cyclopropyl, and cyclopropylmethyl.

In one embodiment, in each of Formulas (I), (IA), and (IA'): $R^1$ is selected from the group consisting of H, methyl, ethyl, and cyclopropyl.

In one embodiment, in each of Formulas (I), (IA), and (IA'): $R^1$ is selected from the group consisting of methyl and ethyl.

In one embodiment, in each of Formulas (I), (IA), and (IA'): $R^1$ is methyl.

In one embodiment, in each of Formulas (I), (IA), and (IA'), $R^9$ is selected from the group consisting of H, halo, lower alkyl, lower cycloalkyl, lower haloalkyl, and lower heteroalkyl.

In one embodiment, in each of Formulas (I), (IA), and (IA'), $R^9$ is selected from the group consisting of H, fluoro, methyl, ethyl, cyclopropyl, —CH$_2$F, —CHF$_2$, —CF$_3$, —CH$_2$OCH$_3$.

In one embodiment, in each of Formulas (I), (IA), and (IA'), $R^9$ is H.

In one embodiment, in each of Formulas (I), (IA), and (IA'), $R^{10}$ is selected from the group consisting of H, halo, lower alkyl, lower haloalkyl, and lower heteroalkyl.

In one embodiment, in each of Formulas (I), (IA), and (IA'), $R^{10}$ is selected from the group consisting of H, fluoro, methyl, ethyl, cyclopropyl, —CH$_2$F, —CHF$_2$, —CF$_3$, —CH$_2$OCH$_3$.

In one embodiment, in each of Formulas (I), (IA), and (IA'), $R^{10}$ is H.

In one embodiment, in each of Formulas (I), (IA), and (IA'), $R^9$ is selected from the group consisting of H, halo, lower alkyl, lower cycloalkyl, lower haloalkyl, and lower heteroalkyl; and $R^{10}$ is H.

In one embodiment, in each of Formulas (I), (IA), and (IA'), $R^9$ is selected from the group consisting of H, fluoro, methyl, ethyl, cyclopropyl, —CH$_2$F, —CHF$_2$, —CF$_3$, —CH$_2$OCH$_3$; and $R^{10}$ is H.

In one embodiment, in each of Formulas (I), (IA), and (IA'), $R^9$ is H; and $R^{10}$ is selected from the group consisting of H, halo, lower alkyl, lower cycloalkyl, lower haloalkyl, and lower heteroalkyl.

In one embodiment, in each of Formulas (I), (IA), and (IA'), $R^9$ is H; and $R^{10}$ is selected from the group consisting of H, fluoro, methyl, ethyl, cyclopropyl, —CH$_2$F, —CHF$_2$, —CF$_3$, —CH$_2$OCH$_3$.

In one embodiment, in each of Formulas (I), (IA), and (IA'), $R^{10}$ is H and $R^9$ is H.

In one embodiment, in each of Formulas (I), (IA), and (IA'), $R^4$ is selected from the group consisting of —CH$_3$, —CH$_2$F, —CHF$_2$, and —CF$_3$.

In one embodiment, in each of Formulas (I), (IA), and (IA'), $R^4$ is selected from the group consisting of —CH$_3$, and —CHF$_2$.

In one embodiment, in each of Formulas (I), (IA), and (IA'):

$R^4$ is selected from the group consisting of —CH$_3$ and —CHF$_2$; and one of $R^9$ and $R^{10}$ is H and the other is selected from the group consisting of H, halo, lower alkyl, lower cycloalkyl, lower haloalkyl, and lower heteroalkyl.

In one embodiment, in each of Formulas (I), (IA), and (IA'):

$R^4$ is selected from the group consisting of —CH$_3$ and —CHF$_2$; and one of $R^9$ and $R^{10}$ is H and the other is selected from the group consisting of H, fluoro, methyl, ethyl, cyclopropyl, —CH$_2$F, —CHF$_2$, —CF$_3$, —CH$_2$OCH$_3$.

In one embodiment, in each of Formulas (I), (IA), and (IA'):

$R^4$ is selected from the group consisting of —CH$_3$ and —CHF$_2$, $R^9$ is H; and $R^{10}$ is H.

In one embodiment, the compounds of the invention have the structural Formula (II):

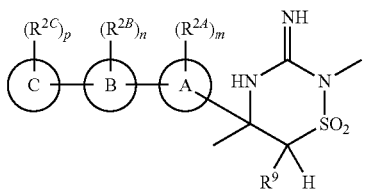
(II)

or a tautomer thereof having the structural Formula (II'):

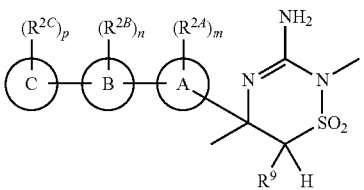
(II')

or pharmaceutically acceptable salt thereof, wherein each variable is as described in Formula (I).

In one embodiment, the compounds of the invention have the structural Formula (IIA):

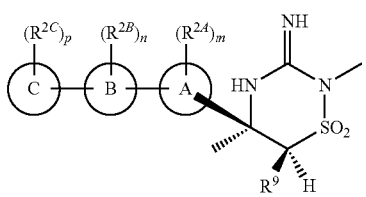
(IIA)

or a tautomer thereof having the structural Formula (IIA'):

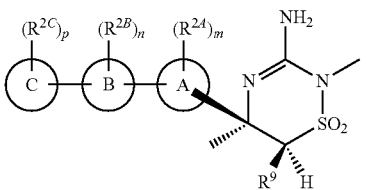
(IIA')

or pharmaceutically acceptable salt thereof, wherein each variable is as described in Formula (I).

In one embodiment, the compounds of the invention have the structural Formula (IIB):

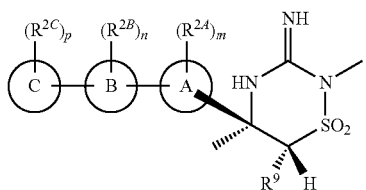
(IIB)

or a tautomer thereof having the structural Formula (IIB'):

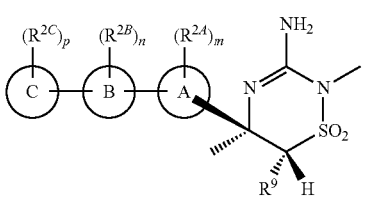
(IIB')

or pharmaceutically acceptable salt thereof, wherein each variable is as described in Formula (I).

In one embodiment, in each of Formulas (II), (II'), (IIA), (IIA'), (IIB), $R^9$ is selected from the group consisting of H, halo, lower alkyl, lower cycloalkyl, lower haloalkyl, and lower heteroalkyl.

In one embodiment, in each of Formulas (II), (II'), (IIA), (IIA'), (IIB), $R^9$ is selected from the group consisting of H, fluoro, methyl, ethyl, cyclopropyl, —$CH_2F$, —$CHF_2$, —$CF_3$, —$CH_2OCH_3$.

In one embodiment, in each of Formulas (II), (II'), (IIA), (IIA'), (IIB), $R^9$ is H.

In one embodiment, in each of Formulas (I), (IA), (IA'), (II), (II'), (IIA), (IIA'), (IIB), and (IIB'): m is 0 or more and ring A is selected from the group consisting of phenyl, pyridyl, pyrazinyl, furanyl, thienyl, pyrimidinyl, pyridazinyl, thiazolyl, thiadiazolyl, isothiazolyl, oxazolyl, oxadiazolyl, isoxazolyl, imidazolyl, pyrazolyl, pyrrolyl, quinazolinyl, benzofuranyl, benzimidazolyl, benzoxazolyl, benzoisoxazolyl, benzothiazolyl, benzoisothiazolyl, benzothienyl, naphthyl, quinolyl, isoquinolyl, indazolyl, indolyl, thienopyridyl, and thienylpyrazolyl.

In one embodiment, in each of Formulas (I), (IA), (IA'), (II), (II'), (IIA), (IIA'), (IIB), and (IIB'): m is 0 or more and ring A is selected from the group consisting of phenyl, pyridyl, thienyl, thiazolyl, pyrazolyl, naphthyl, quinolinyl, benzothienyl, benzimidazolyl, indazolyl, indolyl, and thienopyridyl.

In one embodiment, in each of Formulas (I), (IA), (IA'), (II), (II'), (IIA), (IIA'), (IIB), and (IIB'): m is 0 or more and ring A is selected from the group consisting of phenyl, pyridyl, thienyl, thiazolyl, thienopyridyl, and benzothienyl.

It shall be understood that, in each of Formulas (I), (IA), (IA'), (II), (II'), (IIA), (IIA'), (IIB), and (IIB'), when m (or n or p) is 0 or more, the maximum number of m (or of n or of p) is the maximum number of substitutable hydrogen atoms on the ring to which $R^{2A}$ (or $R^{2B}$ in the case of n or $R^{2C}$ in the case of p) is shown attached.

Thus, in embodiments wherein ring A is a moiety having 4 substitutable hydrogen atoms, m is 0, 1, 2, 3, or 4. In an alternative of such embodiments wherein ring A is a moiety having 4 substitutable hydrogen atoms, m is 0, 1, 2, or 3. In an alternative of such embodiments wherein ring A is a moiety having 4 substitutable hydrogen atoms, m is 0, 1, or 2. In an alternative of such embodiments wherein ring A is a moiety having 4 substitutable hydrogen atoms, m is 0 or 1. In an alternative of such embodiments wherein ring A is a moiety having 4 substitutable hydrogen atoms, m is 0.

In embodiments wherein ring A is a moiety having 3 substitutable hydrogen atoms, m is 0, 1, 2, or 3. In an alternative of such embodiments wherein ring A is a moiety having 3 substitutable hydrogen atoms, m is 0, 1, or 2. In an alternative of such embodiments wherein ring A is a moiety having 3 substitutable hydrogen atoms, m is 0 or 1. In alternative of such embodiments wherein ring A is a moiety having 3 substitutable hydrogen atoms, m is 0.

In embodiments wherein ring A is a moiety having 2 substitutable hydrogen atoms, m is 0, 1, or 2. In an alternative of such embodiments wherein ring A is a moiety having 2 substitutable hydrogen atoms, m is 0 or 1. In alternative of such embodiments wherein ring A is a moiety having 2 substitutable hydrogen atoms, m is 0.

In one embodiment, in each of Formulas (I), (IA), (IA'), (II), (II'), (IIA), (IIA'), (IIB), and (IIB'): each $R^{2A}$ group (when present) is independently selected from the group consisting of halo, oxo, —CN, —SF$_5$, —NHCH$_3$, —N(CH$_3$)$_2$, —OCH$_3$, —OCH$_2$CH$_3$, —O-cyclopropyl, —O—CH$_2$-cyclopropyl, —CH$_2$OCH$_3$, —S(CH$_3$), methyl, ethyl, propyl, cyclopropyl, —CH$_2$-cyclopropyl, —C≡C—CH$_3$, —CF$_3$, —CHF$_2$, —OCF$_3$, and —OCHF$_2$.

In one embodiment, in each of Formulas (I), (IA), (IA'), (II), (II'), (IIA), (IIA'), (IIB), and (IIB'): each $R^{2A}$ group (when present) is independently selected from fluoro, chloro, bromo, —CN, —CF$_3$, —CHF$_2$, —CH$_2$F, cyclopropyl, —OCF$_3$, and —OCHF$_2$.

In one embodiment, in each of Formulas (I), (IA), (IA'), (II), (II'), (IIA), (IIA'), (IIB), and (IIB'): each $R^{2A}$ group (when present) is independently selected from the group consisting of fluoro, chloro, —CHF$_2$, and —CF$_3$.

In one embodiment, in each of Formulas (I), (IA), (IA'), (II), (II'), (IIA), (IIA'), (IIB), and (IIB'): each $R^{2A}$ group (when present) is independently selected from the group consisting of fluoro and chloro.

In one embodiment, in each of Formulas (I), (IA), (IA'), (II), (II'), (IIA), (IIA'), (IIB), and (IIB'):
ring B is selected from the group consisting of phenyl, pyridyl, tetrahydropyridyl, pyrimidinyl, pyrazinyl, triazinyl, tetrazinyl, piperidinyl, and piperazinyl.

In one embodiment, in each of Formulas (I), (IA), (IA'), (II), (II'), (IIA), (IIA'), (IIB), and (IIB'):
ring B is selected from the group consisting of phenyl, pyridyl, tetrahydropyridyl, piperidinyl, pyrimidinyl, and piperazinyl.

In embodiments wherein ring B is a moiety having 4 substitutable hydrogen atoms, n is 0, 1, 2, 3, or 4. In an alternative of such embodiments wherein ring B is a moiety having 4 substitutable hydrogen atoms, n is 0, 1, 2, or 3. In an alternative of such embodiments wherein ring B is a moiety having 4 substitutable hydrogen atoms, n is 0, 1, or 2. In an alternative of such embodiments wherein ring B is a moiety having 3 substitutable hydrogen atoms, n is 0 or 1. In alternative of such embodiments wherein ring B is a moiety having 3 substitutable hydrogen atoms, n is 0.

In embodiments wherein ring B is a moiety having 3 substitutable hydrogen atoms, n is 0, 1, 2, or 3. In an alternative of such embodiments wherein ring B is a moiety having 3 substitutable hydrogen atoms, n is 0, 1, or 2. In an alternative of such embodiments wherein ring B is a moiety having 3 substitutable hydrogen atoms, n is 0 or 1. In alternative of such embodiments wherein ring B is a moiety having 3 substitutable hydrogen atoms, n is 0.

In embodiments wherein ring B is a moiety having 2 substitutable hydrogen atoms, n is 0, 1, or 2. In an alternative of such embodiments wherein ring B is a moiety having 2 substitutable hydrogen atoms, n is 0 or 1. In alternative of such embodiments wherein ring B is a moiety having 2 substitutable hydrogen atoms, n is 0.

In embodiments wherein ring B is a moiety having 1 substitutable hydrogen atom, n is 0 or 1. In an alternative of such embodiments wherein ring B is a moiety having 1 substitutable hydrogen atoms, n is 0.

In one embodiment, in each of Formulas (I), (IA), (IA'), (II), (II'), (IIA), (IIA'), (IIB), and (IIB'):
each $R^{2B}$ (when present) is independently selected from the group consisting of halo, —CN, methyl, ethyl, propyl, cyclopropyl, —CH$_2$-cyclopropyl, —OCH$_3$, —CH$_2$OCH$_3$, —CHF$_2$, —CH$_2$F, —CF$_3$, —OCF$_3$, and —OCHF$_2$.

In one embodiment, in each of Formulas (I), (IA), (IA'), (II), (II'), (IIA), (IIA'), (IIB), and (IIB'):
each $R^{2B}$ (when present) is independently selected from the group consisting of fluoro, chloro, —CN, methyl, cyclopropyl, —CH$_2$OCH$_3$, —CHF$_2$, and —CF$_3$.

In one embodiment, in each of Formulas (I), (IA), (IA'), (II), (II'), (IIA), (IIA'), (IIB), and (IIB'):
each $R^{2B}$ (when present) is independently selected from the group consisting of fluoro, methyl, —CHF$_2$, and —CF$_3$.

In one embodiment, in each of Formulas (I), (IA), (IA'), (II), (II'), (IIA), (IIA'), (IIB), and (IIB'):
ring C is selected from the group consisting of azetidinyl, benzimidazolyl, benzothiazolyl, cyclopropyl, cyclobutyl, dihydroindenyl, dihydrooxazolyl, furanyl, imadazolyl, indenyl, indolyl, isothiazolyl, isoxazolyl, morpholinyl, oxadiazolyl, oxazolyl, phenyl, piperazinyl, pyrazinyl, pyrazolyl, pyridazinyl, pyridyl, pyrimidinyl, pyrazolopyridinyl, pyrrolyl, pyrrolopyridinyl, pyrrolopyrimidinyl, tetrazolyl, thiadiazolyl, thiazolyl, thienyl, thiomorpholinyl, thiomorpholinyl dioxide, and triazolyl.

In one embodiment, in each of Formulas (I), (IA), (IA'), (II), (II'), (IIA), (IIA'), (IIB), and (IIB'):
ring C is selected from the group consisting of azetidinyl, cyclopropyl, cyclobutyl, dihydrooxazolyl, imadazolyl, isothiazolyl, isoxazolyl, morpholinyl, oxadiazolyl, oxazolyl, phenyl, piperazinyl, pyrazinyl, pyrazolyl, pyridazinyl, pyridyl, pyrimidinyl, pyrrolyl, tetrazolyl, thiadiazolyl, thiazolyl, thienyl, thiomorpholinyl, thiomorpholinyl dioxide, and triazolyl.

In one embodiment, in each of Formulas (I), (IA), (IA'), (II), (II'), (IIA), (IIA'), (IIB), and (IIB'): p is 0 and $R^{2C}$ is absent.

In one embodiment, in each of Formulas (I), (IA), (IA'), (II), (II'), (IIA), (IIA'), (IIB), and (IIB'): p is 1 or more and at least one $R^{2C}$ group is present.

In one embodiment, in each of Formulas (I), (IA), (IA'), (II), (II'), (IIA), (IIA'), (IIB), and (IIB'):
each $R^{2C}$ group (when present) is independently selected from the group consisting of halo, oxo, —CN, —SF$_5$, —OSF$_5$, —N(R$^6$)$_2$, —NR$^7$C(O)R$^6$, —NR$^7$S(O)$_2$R$^{12}$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^{12}$, —S(O)$_2$R$^{12}$, —S(O)$_2$N(R$^6$)$_2$, —OR$^6$, —SR$^6$, lower alkyl, lower haloalkyl, lower heteroalkyl, lower alkynyl, aryl, -alkyl-aryl-, cycloalkyl, heteroaryl, -alkyl-heteroaryl, heterocycloalkyl, and heterocycloalkenyl,
  wherein each said lower alkyl, lower haloalkyl, lower heteroalkyl, lower alkynyl, aryl, -alkyl-aryl-, cycloalkyl, heteroaryl, -alkyl-heteroaryl, heterocycloalkyl, and heterocycloalkenyl of $R^{2C}$ (when present) is independently unsubstituted or substituted with one or more groups independently selected from the group consisting of $R^8$.

In one embodiment, in each of Formulas (I), (IA), (IA'), (II), (II'), (IIA), (IIA'), (IIB), and (IIB'):
each $R^{2C}$ group (when present) is independently selected from the group consisting of halo, oxo, —CN, —OR$^6$, —SR$^6$, lower alkyl, lower haloalkyl, lower heteroalkyl, lower alkynyl, aryl, -alkyl-aryl, cycloalkyl, heteroaryl, -alkyl-heteroaryl, heterocycloalkyl, and heterocycloalkenyl,
  wherein each said lower alkyl, lower haloalkyl, lower heteroalkyl, lower alkynyl, aryl, -alkyl-aryl, cycloalkyl, heteroaryl, -alkyl-heteroaryl, heterocycloalkyl, and heterocycloalkenyl of $R^{2C}$ (when present) is independently unsubstituted or substituted with one or more groups independently selected from the group consisting of $R^8$.

An alternative embodiment of $R^6$ when at least one $R^{2C}$ is —$OR^6$, —$N(R^6)_2$, and/or —$SR^6$ includes H, lower alkyl, lower haloalkyl, cyclopropyl, phenyl, and benzyl.

An alternative embodiment of aryl when at least one $R^{2C}$ is aryl or -alkyl-aryl includes phenyl and benzyl. As stated above, each said aryl or -alkyl-aryl group is optionally unsubstituted or substituted with one or more $R^8$ groups.

An alternative embodiment of heteroaryl when at least one $R^{2C}$ is heteroaryl or -alkyl-heteroaryl includes pyridyl, pyrazinyl, pyrrolyl, furanyl, thienyl, pyrimidinyl, pyridazinyl, thiazolyl, thiadiazoyl, isothiazoyl, oxazolyl, oxadiazoyl, isoxazoyl, imidazolyl, pyrazolyl, tetrazoyl, triazoyl, or lower alkyl linked versions thereof. As stated above, each said heteroaryl or -alkyl-heteroaryl group is optionally unsubstituted or substituted with one or more $R^8$ groups.

An alternative embodiment of cycloalkyl when at least one $R^{2C}$ is cycloalkyl includes cyclopropyl, cyclobutyl, cyclopentyl and cyclohexyl. As stated above, each said cycloalkyl group is optionally unsubstituted or substituted with one or more $R^8$ groups.

An alternative embodiment of heterocycloalkyl or heterocycloalkenyl when at least one $R^{2C}$ is heterocycloalkyl or heterocycloalkenyl includes piperidyl, pyrrolidinyl, piperazinyl, morpholinyl, thiomorpholinyl, thiazolidinyl, 1,4-dioxanyl, oxetanyl, tetrahydrofuranyl, tetrahydrothiophenyl. As stated above, each said heterocycloalkyl or heterocycloalkenyl group is optionally unsubstituted or substituted with one or more $R^8$ groups.

In an alternative of each of the preceeding embodiments wherein one or more $R^8$ groups are optionally present, said $R^8$ group is selected from the group consisting of fluoro, chloro, oxo, —CN, methyl, ethyl, propyl, cyclopropyl, —$CH_2$-cyclopropyl, —$C(O)OCH_3$, —$OCH_3$, —$CH_2OCH_3$, —$CHF_2$, —$CH_2F$, —$CF_3$, —$OCF_3$, and —$OCHF_2$.

In one embodiment, in each of Formulas (I), (IA), (IA'), (II), (II'), (IIA), (IIA'), (IIB), and (IIB'):
each $R^{2C}$ group (when present) is independently selected from the group consisting of halo, oxo, —CN, methyl, ethyl, propyl, cyclopropyl, —$CH_2$-cyclopropyl, —$OCH_3$, —$CH_2OCH_3$, —$CHF_2$, —$CH_2F$, —$CF_3$, —$OCF_3$, and —$OCHF_2$.

In one embodiment, in each of Formulas (I), (IA), (IA'), (II), (II'), (IIA), (IIA'), (IIB), and (IIB'):
each $R^{2C}$ (when present) is independently selected from the group consisting of fluoro, chloro, oxo, —CN, methyl, ethyl, propyl, cyclopropyl, —$OCH_3$, —$CHF_2$, —$CH_2F$, —$CF_3$, and —$OCF_3$.

In embodiments wherein ring C is a moiety having a given number of substitutable hydrogen atoms, p is 0, 1, 2, 3, 4, . . . up to said given number of substitutable hydrogen atoms.

Thus, by way of non-limiting example, in embodiments wherein ring C is a moiety having 4 substitutable hydrogen atoms, p is 0, 1, 2, 3, or 4. In an alternative of such embodiments wherein ring C is a moiety having 4 substitutable hydrogen atoms, p is 0, 1, 2, or 3. In an alternative of such embodiments wherein ring C is a moiety having 4 substitutable hydrogen atoms, p is 0, 1, or 2. In an alternative of such embodiments wherein ring C is a moiety having 4 substitutable hydrogen atoms, p is 0 or 1. In an alternative of such embodiments wherein ring C is a moiety having 4 substitutable hydrogen atoms, p is 0.

In embodiments wherein ring C is a moiety having 3 substitutable hydrogen atoms, p is 0, 1, 2, or 3. In an alternative of such embodiments wherein ring C is a moiety having 3 substitutable hydrogen atoms, p is 0, 1, or 2. In an alternative of such embodiments wherein ring C is a moiety having 3 substitutable hydrogen atoms, p is 0 or 1. In alternative of such embodiments wherein ring C is a moiety having 3 substitutable hydrogen atoms, p is 0.

In embodiments wherein ring C is a moiety having 2 substitutable hydrogen atoms, p is 0, 1, or 2. In an alternative of such embodiments wherein ring C is a moiety having 2 substitutable hydrogen atoms, p is 0 or 1. In alternative of such embodiments wherein ring C is a moiety having 2 substitutable hydrogen atoms, p is 0.

In one embodiment, in each of Formulas (I), (IA), (IA'), (II), (II'), (IIA), (IIA'), (IIB), and (IIB'):
ring A is selected from the group consisting of phenyl, pyridyl, thienyl, thiazolyl, thienopyridyl, and benzothienyl;
ring B is selected from the group consisting of phenyl, pyridyl, tetrahydropyridyl, piperidinyl, pyrimidinyl, and piperazinyl;
ring C is selected from the group consisting of azetidinyl, benzimidazolyl, benzothiazolyl, cyclopropyl, cyclobutyl, dihydroindenyl, dihydrooxazolyl, furanyl, imadazolyl, indenyl, indolyl, isothiazolyl, isoxazolyl, morpholinyl, oxadiazolyl, oxazolyl, phenyl, piperazinyl, pyrazinyl, pyrazolyl, pyridazinyl, pyridyl, pyrimidinyl, pyrazolopyridinyl, pyrrolyl, pyrrolopyridinyl, pyrrolopyrimidinyl, tetrazolyl, thiadiazolyl, thiazolyl, thienyl, thiomorpholinyl, thiomorpholinyl dioxide, and triazolyl;
and each of m, $R^{2A}$, n, $R^{2B}$, p, and $R^{2C}$ is as defined in any of the embodiments or alternative embodiments described hereinabove.

In an alternative of the immediately preceeding embodiment, ring C is selected from the group consisting of azetidinyl, cyclopropyl, cyclobutyl, dihydrooxazolyl, imadazolyl, isothiazolyl, isoxazolyl, morpholinyl, oxadiazolyl, oxazolyl, phenyl, piperazinyl, pyrazinyl, pyrazolyl, pyridazinyl, pyridyl, pyrimidinyl, pyrrolyl, tetrazolyl, thiadiazolyl, thiazolyl, thienyl, thiomorpholinyl, thiomorpholinyl dioxide, and triazolyl.

Specific non-limiting examples of compounds of the invention are shown in the table of examples below. While only one tautomeric form of each compound is shown in the tables, it shall be understood that all tautomeric forms of the compounds are contemplated as being within the scope of the non-limiting examples.

In another embodiment, 1 to 3 carbon atoms of the compounds of the invention may be replaced with 1 to 3 silicon atoms so long as all valency requirements are satisfied.

In another embodiment, there is provided a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents which may be useful in combination with the compounds of the invention include those selected from the group consisting of: (a) drugs that may be useful for the treatment of Alzheimer's disease and/or drugs that may be useful for treating one or more symptoms of Alzheimer's disease, (b) drugs that may be useful for inhibiting the synthesis Aβ, (c) drugs that may be useful for treating neurodegenerative diseases, and (d) drugs that may be useful for the treatment of type II diabetes and/or one or more symptoms or associated pathologies thereof.

Non-limiting examples of additional therapeutic agents which may be useful in combination with the compounds of the invention include drugs that may be useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Non-limiting examples of additional therapeutic agents for that may be useful in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer).

Another embodiment provides a method of preparing a pharmaceutical composition comprising the step of admixing at least one compound of the invention, or a tautomer or stereoisomer thereof, or pharmaceutically acceptable salt or solvate of said compound, said stereoisomer, or said tautomer, and a pharmaceutically acceptable carrier or diluent.

Another embodiment provides a method of inhibiting β-secretase comprising exposing a population of cells expressing β-secretase to at least one compound of the invention, or a tautomer or stereoisomer thereof, or pharmaceutically acceptable salt or solvate of said compound, said stereoisomer, or said tautomer, in an amount effective to inhibit β-secretase. In one such embodiment, said population of cells is in vivo. In another such embodiment, said population of cells is ex vivo. In another such embodiment, said population of cells is in vitro.

Additional embodiments in which the compounds of the invention may be useful include: a method of inhibiting β-secretase in a patient in need thereof. A method of inhibiting the formation of Aβ from APP in a patient in need thereof. A method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer or stereoisomer thereof, or pharmaceutically acceptable salt or solvate of said compound, said stereoisomer, or said tautomer, in a therapeutically effective amount to inhibit said pathology or condition in said patient.

Additional embodiments in which the compounds of the invention may be useful include: a method of treating, preventing, and/or delaying the onset of one or more pathologies associated with Aβ and/or one or more symptoms of one or more pathologies associated with Aβ. Non-limiting examples of pathologies which may be associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, said method(s) comprising administering to said patient in need thereof at least one compound of the invention, or a tautomer or stereoisomer thereof, or pharmaceutically acceptable salt or solvate of said compound, said stereoisomer, or said tautomer, in an amount effective to inhibit said pathology or pathologies.

Another embodiment in which the compounds of the invention may be useful includes a method of treating Alzheimer's disease, wherein said method comprises administering an effective (i.e., therapeutically effective) amount of one or more compounds of the invention (or a tautomer or stereoisomer thereof, or pharmaceutically acceptable salt or solvate of said compound, said stereoisomer, or said tautomer), optionally in further combination with one or more additional therapeutic agents which may be effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

Another embodiment in which the compounds of the invention may be useful includes a method of treating mild cognitive impairment ("MCI"), wherein said method comprises administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment. In one such embodiment, treatment is commenced prior to the onset of symptoms.

Another embodiment in which the compounds of the invention may be useful includes a method of preventing, or alternatively of delaying the onset, of mild cognitive impairment or, in a related embodiment, of preventing or alternatively of delaying the onset of Alzheimer's disease. In such embodiments, treatment can be initiated prior to the onset of symptoms, in some embodiments significantly before (e.g., from several months to several years before) the onset of symptoms to a patient at risk for developing MCI or Alzheimer's disease. Thus, such methods comprise administering, prior to the onset of symptoms or clinical or biological evidence of MCI or Alzheimer's disease (e.g., from several months to several yeards before, an effective (i.e., therapeutically effective), and over a period of time and at a frequency of dose sufficient for the therapeutically effective degree of inhibition of the BACE enzyme over the period of treatment, an amount of one or more compounds of the invention (or a tautomer or stereoisomer thereof, or pharmaceutically acceptable salt or solvate of said compound, said stereoisomer, or said tautomer) to a patient in need of treatment.

Another embodiment in which the compounds of the invention may be useful includes a method of treating Down's syndrome, comprising administering an effective (i.e., therapeutically effective) amount of one or more compounds of the invention (or a tautomer or stereoisomer thereof, or pharmaceutically acceptable salt or solvate of said compound, said stereoisomer, or said tautomer) to a patient in need of treatment.

Another embodiment in which the compounds of the invention may be useful includes a kit comprising, in separate containers, in a single package, pharmaceutical compositions for use in combination, wherein one container comprises an effective amount of a compound of the invention (or a tautomer or stereoisomer thereof, or pharmaceutically acceptable salt or solvate of said compound, said stereoisomer, or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1 and/or BACE-2.

In various embodiments, the compositions and methods disclosed above and below wherein the compound(s) of the invention is a compound or compounds selected from the group consisting of the exemplary compounds of the invention described below.

In another embodiment, the invention provides for the use of a compound of the invention, or a tautomer or stereoisomer thereof, or pharmaceutically acceptable salt or solvate of said compound, said stereoisomer, or said tautomer, in the manufacture of a medicament which may be useful in: the treatment, the delay of onset, and/or the prevention of one or more $A\beta$ pathologies and/or in the treatment, the delay of onset, and/or the prevention of one or more symptoms of one or more $A\beta$ pathologies.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

In the various embodiments described herein, each variable is selected independently of the others unless otherwise indicated.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the aforesaid bulk composition and individual dosage units.

"Halogen" (or "halo") means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl and t-butyl.

"Haloalkyl" means an alkyl as defined above wherein one or more hydrogen atoms on the alkyl is replaced by a halo group defined above.

"Heteroalkyl" means an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), S(O)$_2$, and —NH—, —N(alkyl)-. Non-limiting examples include ethers, thioethers, amines, and the like.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, heterocycloalkyl, etc. indicates a divalent moiety, e.g., —CH$_2$CH$_2$— is ethylene, and

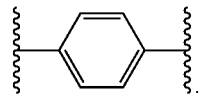 [SMILES: *c1ccc(*)cc1]

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl.

"Alkenylene" means a difunctional group obtained by removal of a hydrogen from an alkenyl group that is defined above. Non-limiting examples of alkenylene include —CH=CH—, —C(CH$_3$)=CH—, and —CH=CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moities include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic mono- or multicyclic ring system comprising about 3 to about 10 carbon atoms, preferably about 5 to about 10 carbon atoms. In some embodiments, cycloalkyl rings contain about 5 to about 7 ring atoms. The term "lower cycloalkyl" encompasses 3 to about 5 ring carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

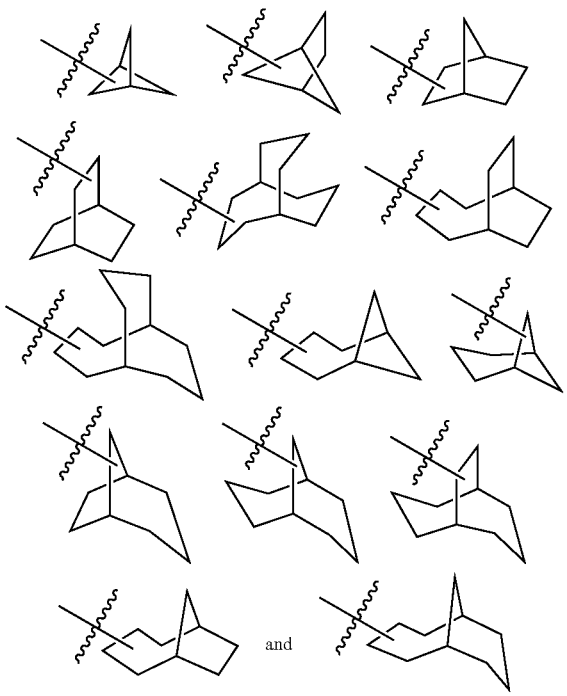

"Cycloalkenyl" means a non-aromatic mono or multicyclic ring system comprising about 3 to about 10 carbon atoms, preferably about 5 to about 10 carbon atoms which contain at least one carbon-carbon double bond. Preferred cycloalkenyl rings contain about 5 to about 7 ring atoms. The cycloalkenyl can be optionally substituted with one or more substituents, which may be the same or different, as described herein. The term "monocyclic cycloalkenyl" refers to monocyclic versions of cycloalkenyl groups described herein and includes non-aromatic 3- to 7-membered monocyclic cycloalkyl groups which contains one or more carbon-carbon double bonds. Non-limiting examples include cyclopropenyl, cyclobutenyl, cyclopentenyl, cyclohexenyl, cyclohetpenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

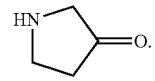

As used herein, the term "monocyclic heterocycloalkyl" refers monocyclic versions of the heterocycloalkyl moities described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and $S(O)_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

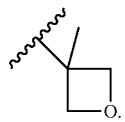

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more substituents, which may be the same or different, as described herein. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidinone (or pyrrolone):

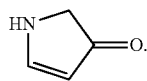

As used herein, the term "monocyclic heterocycloalkenyl" refers to monocyclic versions of the heterocycloalkenyl moities described herein and include 4- to 7-membered monocyclic heterocycloalkenyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, dihydrothiophenyl, and dihydrothiopyranyl, and oxides thereof.

It should be noted that in hetero-atom containing ring systems of this invention, there are no hydroxyl groups on carbon atoms adjacent to a N, O or S, as well as there are no N or S groups on carbon adjacent to another heteroatom.

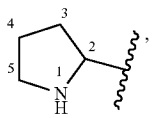

there is no —OH attached directly to carbons marked 2 and 5.

As used herein, the term "multicyclic group" refers to a fused ring system comprising two (bicyclic), three (tricyclic), or more fused rings, wherein each ring of the fused ring system is independently selected from the group consisting of phenyl, monocyclic heteroaryl, monocyclic cycloalkyl, monocyclic cycloalkenyl, monocyclic heterocycloalkyl, and monocyclic heterocycloalkenyl, as defined above. The point of attachment to the parent moiety is to any available ring carbon or (if present) ring heteroatom on any of the fused rings. It shall be understood that each of the following multicyclic groups pictured may be unsubstituted or substituted, as described herein. Only the point of attachment to the parent moiety is shown by the wavy line.

The term multicyclic group includes bicyclic aromatic groups. Non-limiting examples of multicyclic groups which are bicyclic aromatic groups include:

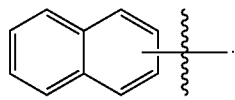

The term multicyclic group thus includes bicyclic heteroaromatic groups comprising from 1 to 3 ring heteroatoms, each said ring heteroatom being independently selected from the group consisting of N, O, and S, S(O), S(O)$_2$, and oxides of N, O, and S, and oxides thereof.

The term multicyclic group includes saturated bicyclic cycloalkyl groups. Non-limiting examples of multicyclic groups which are saturated bicyclic cycloalkyl groups include the following:

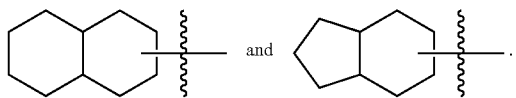

The term multicyclic group includes partially unsaturated bicyclic cycloalkyl groups. Non-limiting examples of multicyclic groups which comprise partially unsaturated bicyclic cycloalkyl groups include the following:

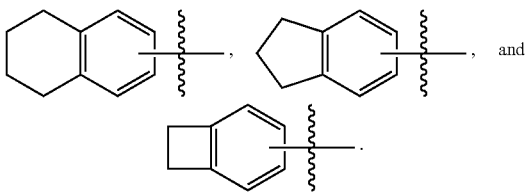

The term multicyclic groups includes partially or fully saturated bicyclic groups comprising from 1 to 3 ring heteroatoms, each said ring heteroatom is independently selected from the group consisting of N, O, and S, S(O), S(O)$_2$, and oxides of N, O, and S.

The term multicyclic group includes aromatic tricyclic groups, cycloalkyl tricyclic groups, as well as heteroaromatic and partially and fully saturated tricyclic groups. For tricyclic groups comprising ring heteroatoms, said tricyclic groups comprise one or more (e.g., from 1 to 5) ring heteroatoms, wherein each said ring heteroatom is independently selected from N, O, and S, S(O), S(O)$_2$, and oxides of N, O, and S:

"Arylalkyl" (or "aralkyl") means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" (or as "-alkyl-aryl") to indicate the point of attachment to the parent moiety. Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. Preferred groups contain a lower alkyl group. Such alkyl groups may be straight or branched, unsubstituted and/or substituted as described herein.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Alkoxy" means an alkyl-O-group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^6$ in $—N(R^6)_2$, or a variable appears more than once in a structure presented herein, the variables can be the same or different.

The line —, as a bond generally indicates a mixture of, or either of, the possible isomers, e.g., containing (R)- and (S)-stereochemistry. For example:

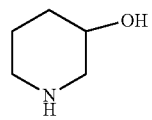

means containing both

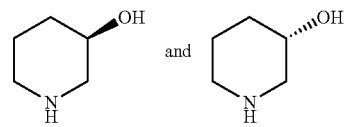

The wavy line ~~~, as used herein, indicates a point of attachment to the rest of the compound. Lines drawn into the ring systems, such as, for example:

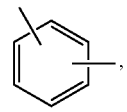

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

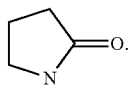

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

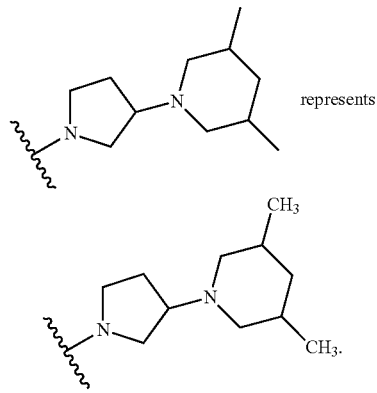

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation compring one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

Compounds of the invention can be made using procedures known in the art. The following reaction schemes show typical procedures, but those skilled in the art will recognize that other procedures can also be suitable. Reactions may involve monitoring for consumption of starting material, and there are many methods for such monitoring, including but not limited to thin layer chromatography (TLC) and liquid chromatography mass spectrometry (LCMS), and those skilled in the art will recognize that where one method is specified, other non-limiting methods may be substituted.

Techniques, solvents and reagents may be referred to by their abbreviations as follows:

| | |
|---|---|
| [1,1'-Bis(diphenylphosphino)ferrocene]-dichloropalladium(II): PdCl$_2$dppf | 3-Chloroperoxybenzoic acid: mCPBA |
| 1-(3-Dimethylaminopropyl)-3-ethylcarbodiimide hydrochloride: EDCI | Acetonitrile: MeCN |
| | Allyl carbamate: Alloc |
| 1,2-dimethoxyethane: DME | Aqueous: aq. |
| 2-(Trimethylsilyl)ethanol: TMSethanol | Atmosphere: atm |
| 2-(Trimethylsilyl)ethoxycarbonyl: Teoc | Benzyl: Bn |
| Bis(2-oxo-3-oxazolidinyl)phosphinic chloride: BOPCl | Lithium diisopropylamide: LDA |
| n-Butyllithium: n-BuLi | Methanesulfonyl chloride: MeSO$_2$Cl |
| Centimeters: cm | Methanol: MeOH |
| Ceric ammonium nitrate: CAN | Methyl magnesium bromide: MeMgBr |
| Concentrated: conc. | Microliters: μl or μL |
| Dichloromethane: DCM | Milligrams: mg |
| 2-Dicyclohexylphosphino-2',4',6'-triisopropylbiphenyl: Xphos | Milliliters: mL |
| Diisopropylamine: iPr$_2$NH | Millimoles: mmol |
| Diisopropylethylamine: DIEA or iPr$_2$NEt | N-bromosuccinimide: NBS |
| Dimethylacetamide: DMA | n-Butyllithium: nBuLi or n-BuLi |
| Dimethylformamide: DMF | Nuclear magnetic resonance spectroscopy: NMR |
| Dimethylsulfoxide: DMSO | Palladium(II) acetate: Pd(OAc)$_2$ |
| Diphenylphosphoryl azide: DPPA | paramethoxy benzyl: PMB |
| Ether or diethyl ether: Et$_2$O | Petroleum ether: PE |
| Ethyl: Et | Preparative: prep |
| Ethyl acetate: AcOEt or EtOAc or EA | Retention time: t$_R$ |
| Ethyl alcohol: EtOH | Reverse Phase: RP |
| Example: Ex. or ex. | Room temperature (ambient, ~25° C): rt or RT |
| Grams: g | Supercritical Fluid Chromatography: SFC |
| Hexanes: hex | tert-Butoxycarbonyl: t-Boc or Boc |
| High performance liquid chromatography: HPLC | Tetrahydrofuran: THF |
| High resolution mass spectrometry: HRMS | Thin layer chromatography: TLC |
| Hours: hrs or h | Triethylamine: Et$_3$N or TEA |
| Iron(III) acetylacetonate: Fe(acac)$_3$ | Trifluoroacetic acid: TFA |
| Inhibition: Inh. | 2,4,6-Tripropyl-1,3,5,2,4,6-trioxatriphosphorinane-2,4-6-trioxide (1-propanephosphonic anhydride): T3P |
| Liquid chromatography mass Spectrometry: LCMS | |

Method A

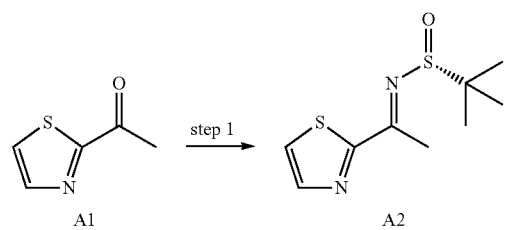

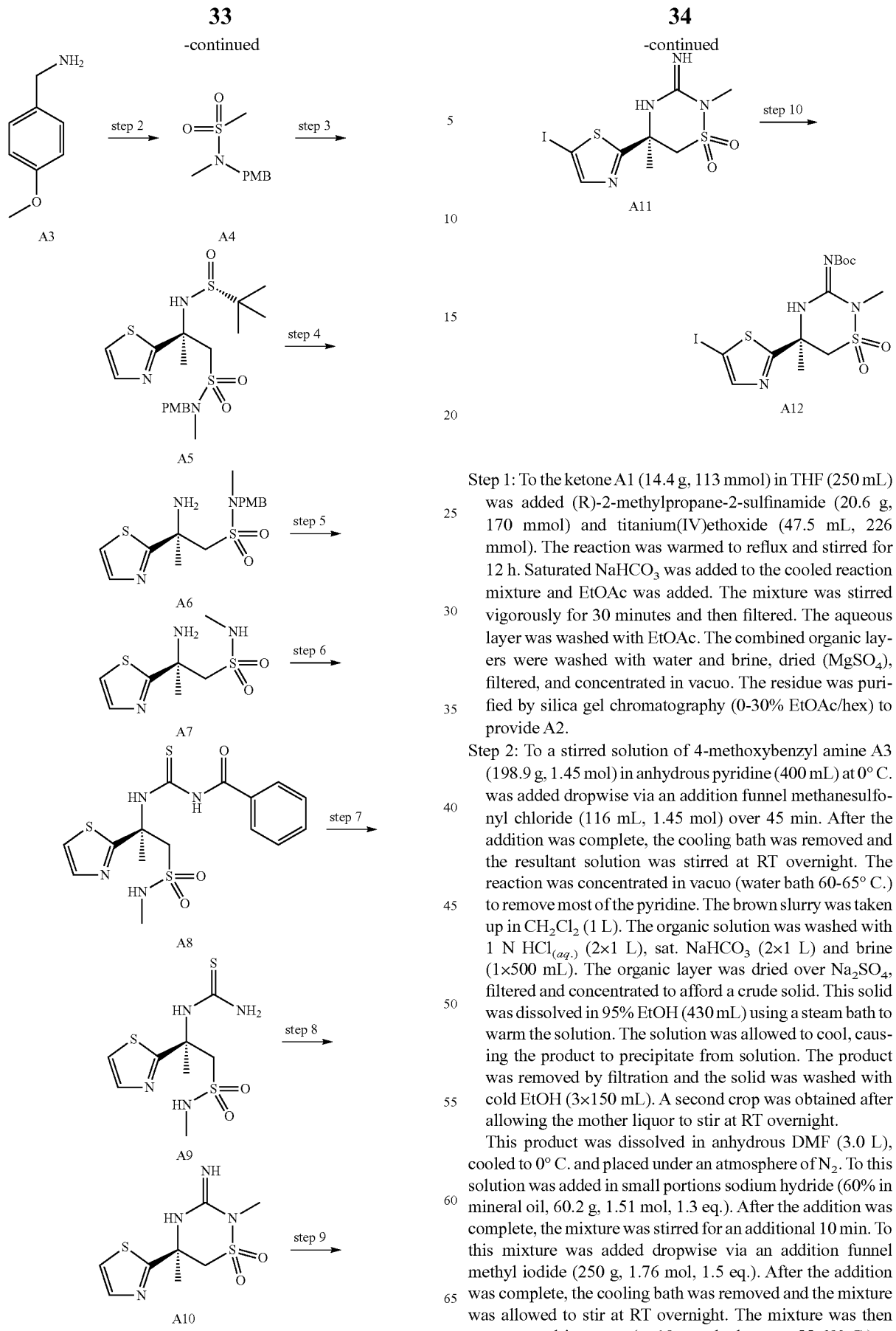

Step 1: To the ketone A1 (14.4 g, 113 mmol) in THF (250 mL) was added (R)-2-methylpropane-2-sulfinamide (20.6 g, 170 mmol) and titanium(IV)ethoxide (47.5 mL, 226 mmol). The reaction was warmed to reflux and stirred for 12 h. Saturated NaHCO$_3$ was added to the cooled reaction mixture and EtOAc was added. The mixture was stirred vigorously for 30 minutes and then filtered. The aqueous layer was washed with EtOAc. The combined organic layers were washed with water and brine, dried (MgSO$_4$), filtered, and concentrated in vacuo. The residue was purified by silica gel chromatography (0-30% EtOAc/hex) to provide A2.

Step 2: To a stirred solution of 4-methoxybenzyl amine A3 (198.9 g, 1.45 mol) in anhydrous pyridine (400 mL) at 0° C. was added dropwise via an addition funnel methanesulfonyl chloride (116 mL, 1.45 mol) over 45 min. After the addition was complete, the cooling bath was removed and the resultant solution was stirred at RT overnight. The reaction was concentrated in vacuo (water bath 60-65° C.) to remove most of the pyridine. The brown slurry was taken up in CH$_2$Cl$_2$ (1 L). The organic solution was washed with 1 N HCl$_{(aq.)}$ (2×1 L), sat. NaHCO$_3$ (2×1 L) and brine (1×500 mL). The organic layer was dried over Na$_2$SO$_4$, filtered and concentrated to afford a crude solid. This solid was dissolved in 95% EtOH (430 mL) using a steam bath to warm the solution. The solution was allowed to cool, causing the product to precipitate from solution. The product was removed by filtration and the solid was washed with cold EtOH (3×150 mL). A second crop was obtained after allowing the mother liquor to stir at RT overnight.

This product was dissolved in anhydrous DMF (3.0 L), cooled to 0° C. and placed under an atmosphere of N$_2$. To this solution was added in small portions sodium hydride (60% in mineral oil, 60.2 g, 1.51 mol, 1.3 eq.). After the addition was complete, the mixture was stirred for an additional 10 min. To this mixture was added dropwise via an addition funnel methyl iodide (250 g, 1.76 mol, 1.5 eq.). After the addition was complete, the cooling bath was removed and the mixture was allowed to stir at RT overnight. The mixture was then concentrated in vacuo (p=10 torr, bath temp=55-60° C.) to remove ca. 2.5 L of DMF. Some solids precipitated from the solution. The product was partitioned between 5 L ice water, 5 L Et$_2$O and 500 mL of EtOAc. The organic layer was separated. The aqueous layer was extracted with Et$_2$O (2×1 L). The combined organic layers were washed with brine (2×1 L), dried over Na$_2$SO$_4$, filtered and concentrated. The oily solid was stirred with hexanes using a wire stir blade to powderize the solid. The solid was removed by filtration and washed with hexanes (2×250 mL). The solid was dissolved in hexanes/EtOAc (1:1, 450 mL) using a steam bath to warm the mixture. An off white precipitate formed on cooling and was filtered off to provide A4 (182 g). The remaining mother liquor was purified via flash chromatography (SiO$_2$: 1:1 hexanes:EtOAc) to afford additional A4.

Step 3: To a solution of A4 (12.4 g, 54 mmol) in THF (120 mL) at −78° C. was added n-BuLi (2.5 M in hexanes, 21.6 mL, 54 mmol). The reaction was stirred at −78° C. for 45 minutes after which time A2 (8.3 g, 36 mmol) in THF (30 mL) was added via cannula. The reaction was stirred at −78° C. for 1 hour. Saturated NH$_4$Cl$_{(aq)}$ (100 mL) was added and the reaction allowed to warm to room temperature. The mixture was extracted with EtOAc. The combined organic layers were washed with water and brine. The organic layer was dried (NaSO$_4$), filtered, and concentrated in vacuo. The residue was purified by silica gel chromatography (0-50% EtOAc/hex) to provide A5 (6.8 g, 41%). The impure fractions were repurified by silica gel chromatography (30-50% EtOAc/hex) to provide additional A5.

Step 4: To A5 (6.8 g, 15 mmol) in DCM (50 mL) and MeOH (50 mL) was added HCl in dioxane (4.0 M, 17 mL, 69 mmol). The reaction was stirred at room temperature for 1 h and then concentrated in vacuo to provide A6 which was used without further purification.

Step 5: To A6 (6.7 g, 19 mmol) in DCM (50 mL) was added TFA (50 mL) and 2-mercaptoacetic acid (6.6 mL, 94 mmol). The reaction was stirred at room temperature for 14 h. The reaction was concentrated in vacuo and 1N HCl$_{(aq)}$ was added. The mixture was extracted with ether. The aqueous layer was then basified with solid potassium carbonate. The mixture was then extracted with EtOAc. The EtOAc layers were washed with water and brine, dried (Na$_2$SO$_4$), filtered, and concentrated in vacuo to provide A7. The residue was used without further purification.

Step 6: To A7 (4.4 g, 19 mmol) in DCM (200 mL) was added benzyl isothiocyanate (3.1 mL, 23 mmol). The reaction was stirred at room temperature for 1 hour and then concentrated in vacuo. The residue was purified by silica gel chromatography (0-50% EtOAc/hex) to provide A8.

Step 7: To A8 (5.0 g, 13 mmol) in MeOH (50 mL) was added sodium methoxide in methanol (25 wt %, 7.9 mL, 22 mmol). The reaction was stirred at room temperature for 1 hour after which 1N HCl$_{(aq)}$ (20 mL) was added. The mixture was concentrated in vacuo and water was added. The mixture was extracted with EtOAc. The combined organic layers were washed with water and brine, dried (MgSO$_4$), filtered, and concentrated in vacuo. The residue was purified by silica gel chromatography (30-80% EtOAc/hex) to provide A9.

Step 8: To A9 (3.7 g, 13 mmol) in EtOH (100 mL) was added potassium carbonate (1.9 g, 14 mmol) followed by methyl iodide (0.86 mL, 14 mmol) in EtOH (10 mL). The reaction was stirred at room temperature for 3 h. The reaction was filtered and the filtrate concentrated in vacuo. The residue was purified by silica gel chromatography (50-100%) to provide A10.

Step 9: To A10 (1.0 g, 4.2 mmol) in TFA (10 mL) was added N-iodosuccinimide (1.4 g, 6.2 mmol). The reaction was warmed to 60° C. and stirred for 1 h. The reaction mixture was poured into ice water and solid potassium carbonate was added to basify solution. The mixture was extracted with EtOAc. The combined organic layers were washed with water and brine, dried (MgSO$_4$), filtered, and concentrated in vacuo. The residue was purified by silica gel chromatography (50-100% EtOAc/hex) to provide A11.

Step 10: To A11 (0.55 g, 1.4 mmol) in DCM (20 mL) was added TEA (0.40 mL, 2.9 mmol) and (Boc)$_2$O (0.62 g, 2.9 mmol). The reaction was stirred at room temperature for 18 h. The reaction was loaded directly onto a silica gel column and dried with nitrogen. The silica gel column was then eluted with 0-25% EtOAc/hex to provide A12.

TABLE 1

The following compounds were prepared using similar procedures to that described in Method A, steps 1-8 and 10, using the appropriate starting materials.

Compounds

A13

[Structure: thiophene ring with Br substituent connected to a chiral carbon bearing a thiadiazine ring with NBoc, N-Me, S(=O)$_2$ groups]

A14

[Structure: thiophene ring with Cl substituent connected to a chiral carbon bearing a thiadiazine ring with NBoc, N-Me, S(=O)$_2$ groups]

A15

[Structure: thiophene ring with F substituent connected to a chiral carbon bearing a thiadiazine ring with NBoc, N-Me, S(=O)$_2$ groups]

A16

[Structure: phenyl ring with Br and F substituents connected to a chiral carbon bearing a thiadiazine ring with NBoc, N-Me, S(=O)$_2$ groups]

Method B

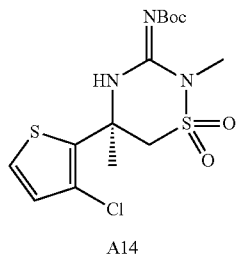

A14

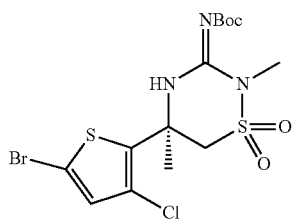

B1

To a solution of the thiophene A14 (2.2 g, 5.6 mmol) in DMF in an aluminum foil wrapped round bottom flask under an atmosphere of $N_2$ was added NBS (2.7 g, 15 mmol). The resultant solution was heated to 50° C. with stirring for 8 hours. The solution was cooled to RT. To the solution was added an aqueous solution of $NaHCO_3$ and $Na_2S_2O_5$. The aqueous layer was extracted EtOAc. The organic layer was washed with sat $NaHCO_{3(aq)}$ (2×). The organic layer was dried over $Na_2SO_4$, filtered and concentrated. The crude product was purified via flash chromatography ($SiO_2$:gradient elution 100:0 to 83:17 hexanes:EtOAc) to afford the bromothiophene B1.

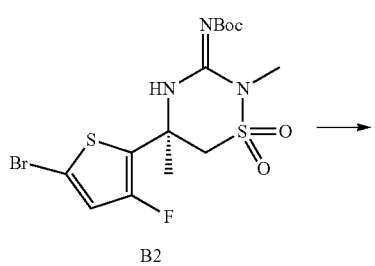

B2

The bromothiophene B2 was prepared in a similar manner as B1 in Method B starting from the fluorothiophene A15.

Method C

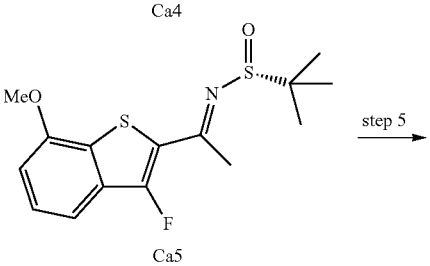

B2

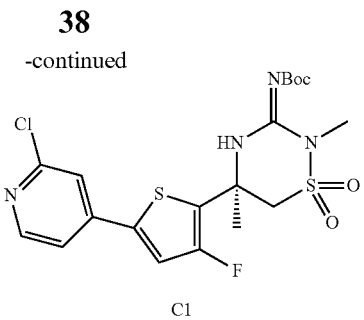

C1

To B2 (0.40 g, 0.88 mmol) in dioxane (4 mL) was added 2-chloro-4-(4,4,5,5-tetramethyl-1,3,2-dioxaborolan-2-yl)pyridine (0.23 g, 0.96 mmol), aqueous potassium carbonate (1 M, 2.6 mL, 2.6 mmol) and $PdCl_2(dppf)$ (0.13 g, 0.17 mmol). The reaction was warmed to 65° C. and stirred for 4 h. The cooled reaction was filtered through a bed of Celite and the filtrate was concentrated in vacuo. The residue was purified by silica gel chromatography (30% EtOAc/hex) to provide C1.

Method Ca

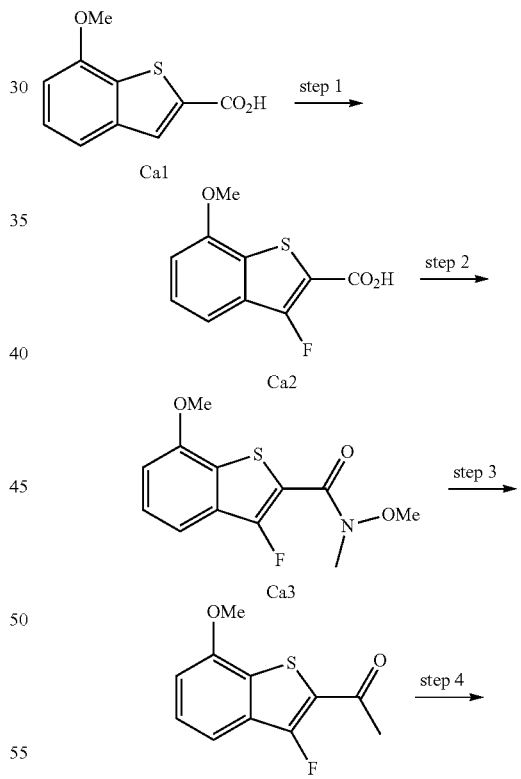

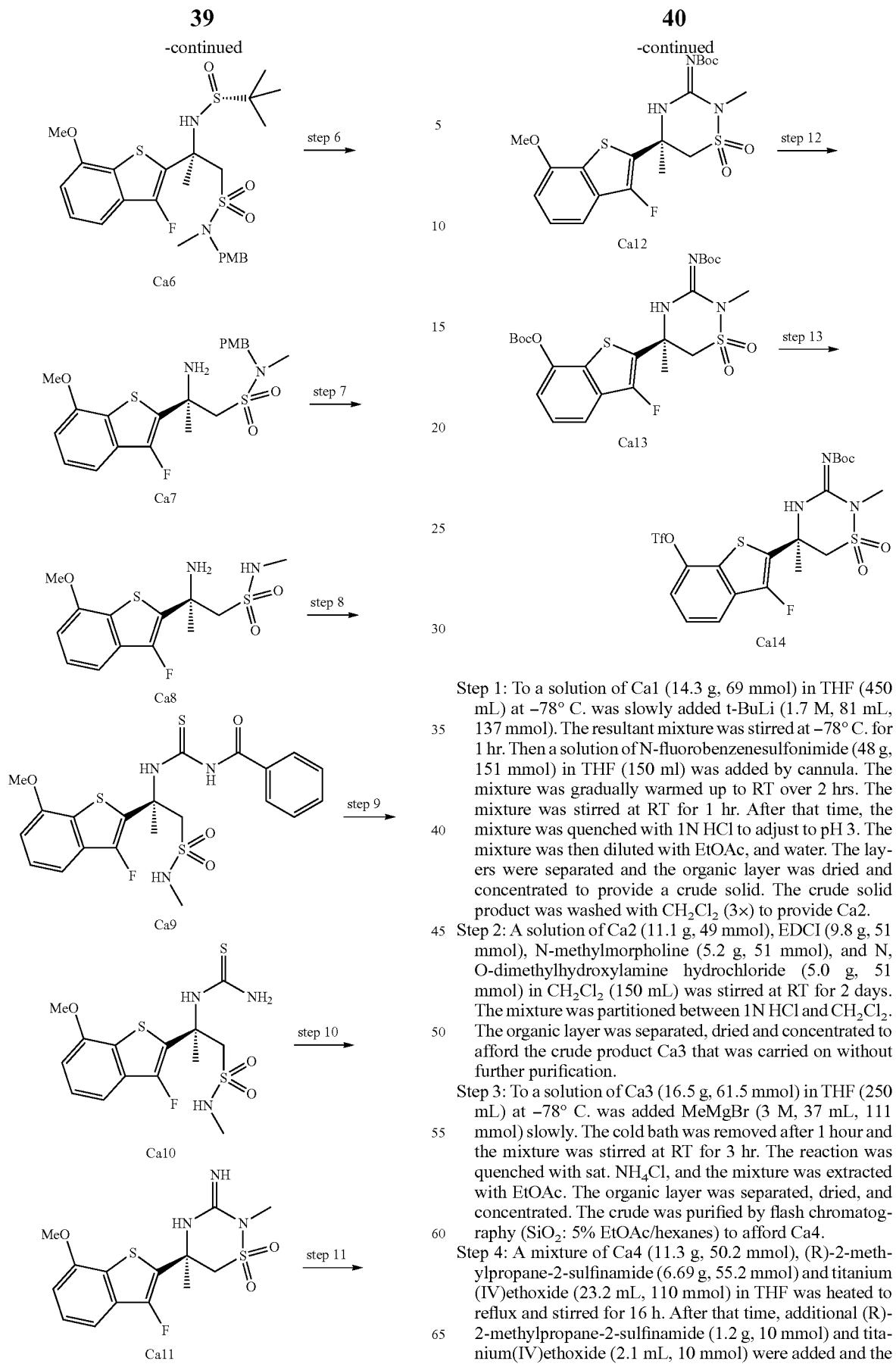

Step 1: To a solution of Ca1 (14.3 g, 69 mmol) in THF (450 mL) at −78° C. was slowly added t-BuLi (1.7 M, 81 mL, 137 mmol). The resultant mixture was stirred at −78° C. for 1 hr. Then a solution of N-fluorobenzenesulfonimide (48 g, 151 mmol) in THF (150 ml) was added by cannula. The mixture was gradually warmed up to RT over 2 hrs. The mixture was stirred at RT for 1 hr. After that time, the mixture was quenched with 1N HCl to adjust to pH 3. The mixture was then diluted with EtOAc, and water. The layers were separated and the organic layer was dried and concentrated to provide a crude solid. The crude solid product was washed with $CH_2Cl_2$ (3×) to provide Ca2.

Step 2: A solution of Ca2 (11.1 g, 49 mmol), EDCI (9.8 g, 51 mmol), N-methylmorpholine (5.2 g, 51 mmol), and N,O-dimethylhydroxylamine hydrochloride (5.0 g, 51 mmol) in $CH_2Cl_2$ (150 mL) was stirred at RT for 2 days. The mixture was partitioned between 1N HCl and $CH_2Cl_2$. The organic layer was separated, dried and concentrated to afford the crude product Ca3 that was carried on without further purification.

Step 3: To a solution of Ca3 (16.5 g, 61.5 mmol) in THF (250 mL) at −78° C. was added MeMgBr (3 M, 37 mL, 111 mmol) slowly. The cold bath was removed after 1 hour and the mixture was stirred at RT for 3 hr. The reaction was quenched with sat. $NH_4Cl$, and the mixture was extracted with EtOAc. The organic layer was separated, dried, and concentrated. The crude was purified by flash chromatography ($SiO_2$: 5% EtOAc/hexanes) to afford Ca4.

Step 4: A mixture of Ca4 (11.3 g, 50.2 mmol), (R)-2-methylpropane-2-sulfinamide (6.69 g, 55.2 mmol) and titanium (IV)ethoxide (23.2 mL, 110 mmol) in THF was heated to reflux and stirred for 16 h. After that time, additional (R)-2-methylpropane-2-sulfinamide (1.2 g, 10 mmol) and titanium(IV)ethoxide (2.1 mL, 10 mmol) were added and the mixture was heated to reflux for an additional 8 hours.

Water was added to the mixture followed by the addition of EtOAc. The resultant mixture was filtered through a pad of Celite and the organic layer was separated, dried and concentrated. The crude product was purified by flash chromatography (SiO$_2$; 15% EtOAc/hexanes) to afford Ca5.

Step 5: To a −78° C. solution of A4 (14.5 g, 63.2 mmol) in THF (250 mL) was added nBuLi (2.5 M in hexanes, 25.3 mL, 63.2 mmol). The mixture was stirred at −78° C. for an hour. To the resultant solution was added via cannula a precooled (−78° C.) solution of Ca5 (13.8 g, 42.1 mmol) in THF (50 mL). The resultant mixture was stirred at −78° C. for 4 hr. After that time, the reaction was quenched with water and the mixture was slowly warmed up to RT. The mixture was then extracted with EtOAc. The organic layer was dried and concentrated. The crude product was purified by flash chromatography (SiO$_2$; gradient elution 35-50% EtOAc/hexanes) to afford Ca6.

Step 6: To a solution of Ca6 (21.2 g, 38.1 mmol) in CH$_2$Cl$_2$ was added a solution of HCl (4 N in dioxane, 57.1 mL, 228 mmol). The resultant solution was stirred at RT for 2 h. After that time the solution was concentrated to afford Ca7 that was carried on to the next step.

Step 7: To Ca7 (17.2 g, 38 mmol) in CH$_2$Cl$_2$ (100 mL) was added TFA (100 mL) and 2-mercaptoacetic acid (20 mL, 288 mmol). The reaction was stirred at room temperature for 16 h. To the solution was added sat NaHCO$_3$, solid NaOH and K$_2$CO$_3$ to basify the aqueous layer. The mixture was then extracted with EtOAc. The EtOAc layers were washed with water and brine, dried (Na$_2$SO$_4$), filtered, and concentrated in vacuo to provide Ca8. The residue was used without further purification.

Step 8: To Ca8 (12.7 g, 38 mmol) in CH$_2$Cl$_2$ (200 mL) was added benzyl isothiocyanate (6.7 mL, 50 mmol). The reaction was stirred at room temperature for 16 hours and then concentrated in vacuo to afford Ca9 that was carried on without further purification.

Step 9: To Ca9 (19 g, 38 mmol) in MeOH (150 mL) was added sodium methoxide in methanol (25 wt %, 22 mL, 38 mmol). The reaction was stirred at room temperature for 2 hours. The mixture was concentrated in vacuo and sat. NaHCO$_3$ was added. The mixture was extracted with CH$_2$Cl$_2$. The organic layer was dried (MgSO$_4$), filtered, and concentrated in vacuo to afford Ca10 that was used without further purification.

Step 10: To Ca10 (15 g, 38 mmol) in EtOH (150 mL) was added methyl iodide (2.9 mL, 46 mmol). The reaction was stirred at room temperature overnight. The mixture was concentrated in vacuo and sat. NaHCO$_3$ was added. The mixture was extracted with EtOAc. The organic layer was dried, filtered, and concentrated in vacuo. The residue was taken up in EtOH (150 mL) and the resultant solution was heated to reflux for 2 hours. The mixture was concentrated in vacuo and sat. NaHCO$_3$ was added. The mixture was extracted with EtOAc. The organic layer was dried, filtered, and concentrated in vacuo to afford Ca11 that was used without further purification.

Step 11: Compound Ca11 was converted to Ca12 using a method similar to that described in Method A Step 10.

Step 12: To a 0° C. solution of Ca12 (6.0 g, 13 mmol) in toluene (100 mL) was added slowly a solution of BBr$_3$ (1M, 53 mL, 53 mmol). After 5 mins the cold bath was removed and the mixture was stirred at RT for 2 hrs. The mixture was quenched with water, extracted with EtOAc. The organic layer was separated. The aqueous layer was neutralized by sat. NaHCO$_3$, and solid K$_2$CO$_3$ followed by extraction with EtOAc. The combined organic layers were dried and concentrated. To the crude product was added DCM (100 mL), Boc$_2$O (5.8 g, 26 mmol) and iPr$_2$NEt (8.5 g, 66 mmol). The mixture was stirred at RT overnight. To the mixture was then added catalytic DMAP and stirred for an additional 1 hour. To the mixture was added 1 M HCl. The aqueous layer was extracted with DCM. The organic layer was dried and filtered. The crude product was purified by flash chromatography (20% EtOAc/hexanes) to afford Ca13.

Step 13: To a solution of Ca13 (5.7 g, 10 mmol) in DCM (50 mL) was added NaOMe (4.5 g, 21 mmol). The mixture was stirred at RT for 2 h. To the mixture was added 1 N HCl. The aqueous layer was extracted with DCM. The organic layer was dried and concentrated. To the residue was added pyridine (40 mL) and trifluoromethanesulfonic anhydride (3.5 g, 12 mmol). The mixture was stirred at RT for 2 h. The mixture was partitioned between 1 N HCl and DCM. The organic layer was separated, dried and concentrated. The crude product was purified by flash chromatography (20% EtOAc/hexanes) to afford Ca14.

Method Cb

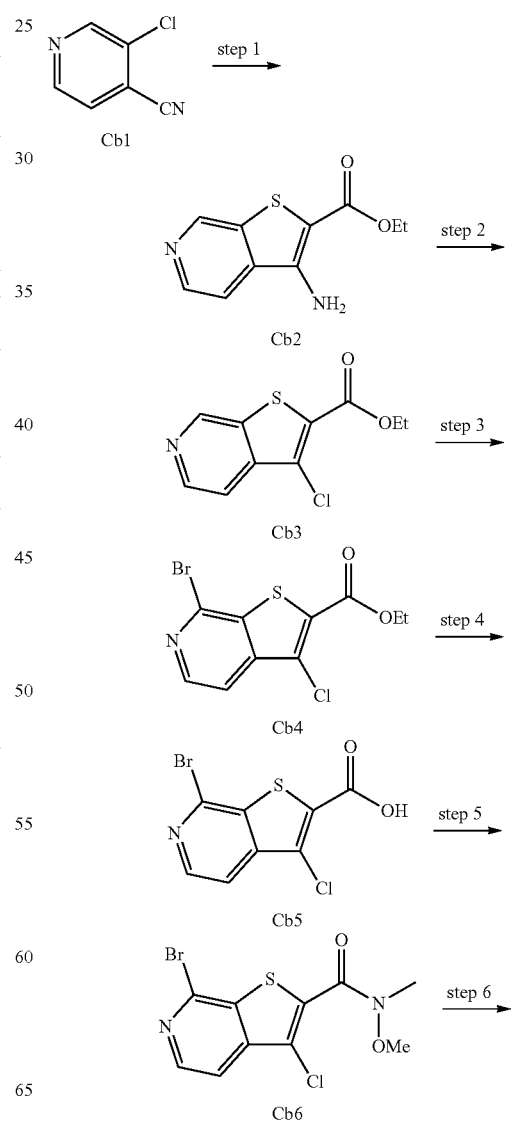

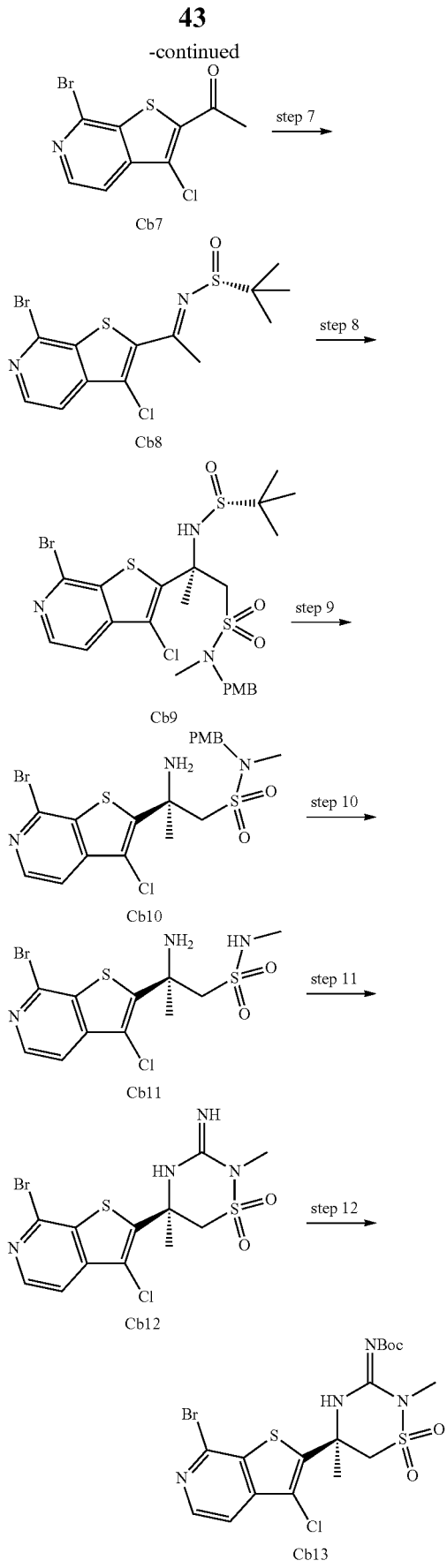

Step 1: To a stirred solution of Cb1 (29.9 g, 216 mmol) and ethyl 2-mercaptoacetate (25.9 g, 216 mmol) in DMF (181 mL) at 0° C. was added KOtBu (24.18 g, 216 mmol) and the mixture was stirred at 0° C. for 0.5 hours. After that time, the mixture was warmed to rt with continued stirring overnight. The mixture was quenched with water and the precipitate filtered off to afford Cb2.

Step 2: To a mechanically stirred slurry of Cb2 (27.7 g, 125 mmol) in 12 N HCl (111 mL) precooled partially in a dry ice-acetone bath (−30° C.) was added dropwise a solution of sodium nitrite (9.89 g, 143 mmol) in water (83 mL). The resulting suspension was aged for 60 min (temperature remained between −10° C. and 0° C.). After that time, the mixture was cooled back to −30° C. Copper(I) chloride (13.57 g, 137 mmol) was added in one portion. The temperature of the mixture was allowed to rise to 12° C. during a course of 2 h. To the mixture was added additional sodium nitrite (2.15 g, 31.2 mmol) in water (20 mL). The mixture was allowed to warm to rt with stirring overnight. The mixture was then extracted with $CH_2Cl_2$ (10×250 mL). The combined organic layers were washed with 250 mL sat. $NaHCO_3$. The organic layer was then concentrated. Triethylamine was added to the crude residue and the product was filtered through a silica gel plug eluting with 99:1 DCM:Et$_3$N. The crude product was then purified via silica gel chromatography (gradient elution 20-50% EtOAc-Hexanes+1% TEA) to afford Cb3.

Step 3: To a stirred solution of Cb3 (27.7 g, 125 mmol) in $CH_2Cl_2$ (161 mL) at 0° C. was added m-CPBA (11.22 g, 50.1 mmol) and the mixture was allowed to slowly warm to rt with stirring overnight. To the mixture was added $CH_2Cl_2$ (100 mL) and the mixture was then washed with 1N NaOH (40 mL). The aqueous layer was extracted with $CH_2Cl_2$ (2×) and the combined organic layers were washed with brine. The organic layer was concentrated and dried over $Na_2SO_4$. The crude material was taken up in DCM (161 mL) and cooled to 0° C. To the solution was added phosphoryl bromide (38.3 g, 134 mmol) and the slurry was allowed to slowly warm to RT overnight with stirring. The mixture was poured into ice and aqueous $NaHCO_3$. Additional aqueous $NaHCO_3$ was added to adjust the pH>9. The aqueous layer was extracted with $CH_2Cl_2$ (2×). The combined organic layers were then washed with brine. The crude product was purified by silica gel chromatography (gradient elution 5-15% EtOAc-Hexanes+1% TEA) to afford Cb4.

Step 4: To a solution of Cb4 (5.0 g, 15.6 mmol) in THF (120 mL) at 0° C. was added 1N LiOH (23 mL, 23 mmol). The mixture was stirred at 0° C. for 45 mins, then warmed up to RT. The mixture was acidified by the addition of 1N HCl. The resulting precipitate was filtered off and washed with water to afford Cb5.

Step 5: A solution of Cb5 (9.1 g, 31 mmol), EDCI (6.3 g, 33 mmol), N,O-dimethylhydroxylamine hydrochloride (3.2 g, 33 mmol) and N-methylmorpholine (3.3 g, 33 mmol) in $CH_2Cl_2$ was stirred at RT for 2.5 days. After that time, additional N,O-dimethylhydroxylamine hydrochloride (0.9 g, 9.3 mmol), EDCI (1.8 g, 9.3 mmol) and N-methylmorpholine (0.93 g, 9.3 mmol) were added and the mixture was stirred for an additional 6 hr at RT. The mixture was then quenched with water and the mixture was extracted with a mixture of EtOAc and hexanes. The organic layer was separated, dried and concentrated. The crude product was purified by flash chromatography ($SiO_2$: 30% EtOAc/hexanes) to afford Cb6.

Step 6: Compound Cb6 was converted to Cb7 using a method similar to that described in Method P Step 3.

Step 7: Compound Cb7 was converted to Cb8 using a method similar to that described in Method A Step 1.

Step 8: To a −78° C. solution of A4 (5.53 g, 24.11 mmol) in THF (65 ml) was added nBuLi (9.65 mL, 24.1 mmol). The mixture was stirred at −78° C. for an hour. A solution of Cb8 (6.33 g, 16.08 mmol) in THF (20 ml) was added by cannula. The mixture was stirred at −78° C. for another 4 hr. After that time, the reaction was quenched with water at −78° C. and the mixture was slowly warmed up to RT. The mixture was then extracted with EtOAc. The organic layer was dried and concentrated. The crude product was purified by flash chromatography (SiO$_2$; gradient elution 50-100% EtOAc/hexanes) to afford a product that was further purified by SFC (Column-OJ-H, solvent 30% EtOH in 120 bar CO$_2$; temp 40° C., detector: UV 200 nm) to afford Cb9.

Step 9: Compound Cb9 was converted to a sample containing Cb10 using a method similar to that described in Method A Step 4.

Step 10: To a solution of the above sample containing Cb10 (1.7 g total sample mass) in CH$_2$Cl$_2$ (10 mL) was added TFA (10 mL) and 1,3-dimethoxybenzene (5 mL). The resulting solution was stirred at RT for 16 hours. After that time, the solution was partitioned between 1 M HCl (aq.) and Et$_2$O. The layers were separated and the aqueous layer was basified by the addition of solid K$_2$CO$_3$. The aqueous layer was then extracted with EtOAc. The organic layer was dried, filtered and concentrated in vacuo to afford a sample containing Cb11.

Step 11: To a solution of the above sample containing Cb11 (1.28 g total sample mass) in propanenitrile (15 mL) was added a solution of cyanogen bromide (5 M in MeCN, 0.83 mL, 4.2 mmol). The resulting solution was heated in a sealed tube at 125° C. for 3 hours. After that time, additional cyanogen bromide (0.4 mL, 2.0 mmol) was added and the solution was heated for an additional 6 hours at 125° C. The solution was cooled to RT and partitioned between sat NaHCO$_3$ (aq.) and EtOAc. The organic layer was separated, dried over Na$_2$SO$_4$, filtered and concentrated to afford a crude product that contained Cb12. This material was carried onto step 12 without purification.

Step 12: A sample containing compound Cb12 was converted to a sample containing Cb13 using a method similar to that described in Method A Step 10.

Method D

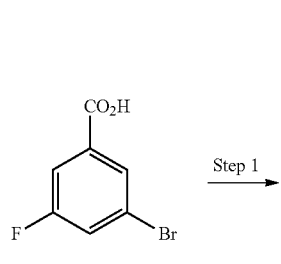

Step 1: To 3-bromo-5-fluorobenzoic acid (4.0 g, 18.3 mol) in EtOAc (45 mL) was added formic acid hydrazide (1.1 g, 18.3 mmol), TEA (7.6 mL, 54.8 mmol), and 1-propanephosphonic acid cyclic anhydride (50% solution in EtOAc, 27.2 mL, 45.7 mmol). The mixture was warmed to 80° C. and stirred for 12 h. The cooled mixture was added to water and then extracted with EtOAc. The combined organic layers were washed with water and brine, dried (MgSO$_4$), filtered, and concentrated in vacuo. The residue was purified by silica gel chromatography (0-25% EtOAc/hex) to provide D1.

TABLE 2

Using the procedure described in Method D, the following carboxylic acids were converted to oxadiazoles.

| Carboxylic Acid | Oxadiazole |
|---|---|
| 3-bromobenzoic acid | D2 |
| 2-fluoro-5-bromobenzoic acid | D3 |
| 2-fluoro-3-bromobenzoic acid | D4 |
| 5-bromonicotinic acid | D5 |
| 3-bromo-4-fluorobenzoic acid | D6 |

Method E

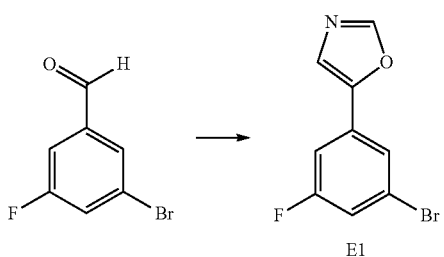 [SMILES: O=Cc1cc(F)cc(Br)c1 ; Fc1cc(Br)cc(-c2cnco2)c1]

To 3-bromo-5-fluorobenzaldehyde (4.8 g, 24 mmol) in MeOH (79 mL) was added potassium carbonate (6.6 g, 48 mmol) and toluenesulphonylmethyl isocyanide (5.1 g, 26 mmol). The reaction was warmed to reflux and stirred for 4 h. The cooled reaction was concentrated in vacuo and water was added to the residue. The precipitate was filtered, washed with water, and air-dried. The solid was taken up into DCM and dried (MgSO₄), filtered, and concentrated in vacuo to provide E1.

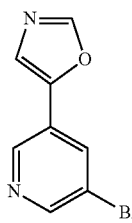

E2

Bromide E2 was prepared in the same manner as E1 in Method E except that 5-bromonicotinaldehyde was used instead of 3-bromo-5-fluorobenzaldehyde.

Method F

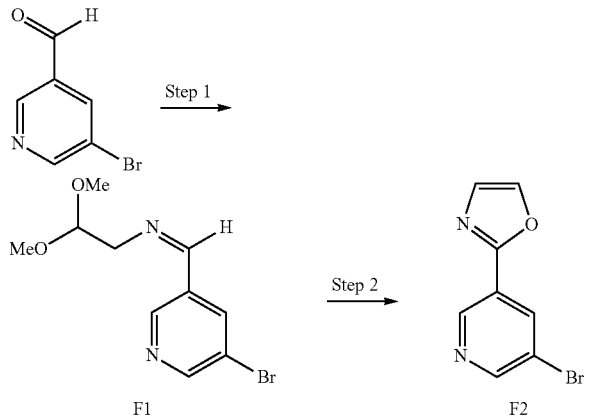

Step 1: To 5-bromonicotinaldehyde (1.5 g, 8.1 mmol) in toluene (80 mL) was added 2,2-dimethoxyethanamine (1.1 mL, 10 mmol). The mixture was warmed to reflux and water was removed using a Dean-Stark apparatus. After 2.5 h, the reaction was cooled and poured into EtOAc. The mixture was washed with water and brine, dried (MgSO₄), filtered, and concentrated in vacuo to provide F1.

Step 2: To the imine F1 prepared in step 1 (5.5 g, 20 mmol) cooled to 0° C. was added concentrated sulfuric acid (40 mL, 750 mmol) followed by phosphorous pentoxide (3.7 g, 26 mmol). The mixture was then warmed to 100° C. and stirred for 30 minutes. The cooled reaction mixture was poured onto ice and the pH was adjusted to ~pH 8 using concentrated NH₄OH. The resultant mixture was extracted with DCM. The combined organic layers were washed with water and brine, dried (MgSO₄), filtered, and concentrated in vacuo. The residue was purified by silica gel chromatography (0-30% EtOAc/hex) over 30 minutes to provide F2.

Method G

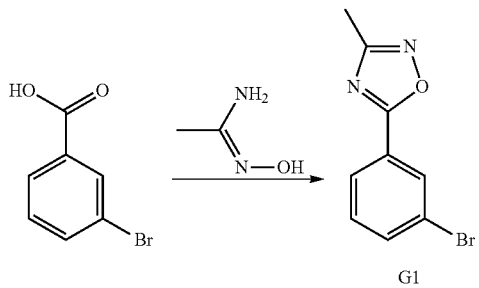

To 3-bromobenzoic acid (2.0 g, 10 mmol) in ethyl acetate (33 mL) was added N-hydroxyacetamide (0.73 g, 10 mmol), TEA (4.2 mL, 30 mmol), and T3P (50% solution in EtOAc, 15 mL, 25 mmol). The reaction was warmed to 80° C. and stirred for 3 hours. The cooled reaction was poured into water and the mixture was extracted with EtOAc. The combined organics were washed with water and brine, dried (MgSO₄), filtered, and concentrated in vacuo. The residue was purified by silica gel chromatography (0-20% EtOAc/hex over 20 minutes) to provide G1.

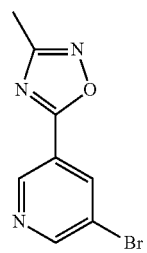

G2

Bromide G2 was prepared in the same manner as G1 in Method G except that 4-bromopicolinic acid was used instead of 3-bromobenzoic acid.

Method H

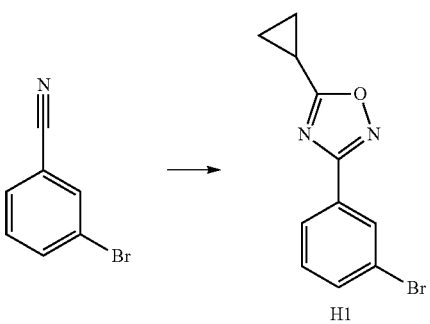

To 3-bromobenzonitrile (2.0 g, 11 mmol) in t-butanol (26 mL) was added hydroxylamine (1.1 g, 17 mmol). The reaction was warmed to 60° C. and stirred for 3 hours. The reaction was cooled and the solvent was removed in vacuo. To the resulting oil was added dioxane (30 mL), pyridine (60 mL), and cyclopropanecarbonyl chloride (1.2 mL, 13 mmol). The reaction was warmed to 100° C. and stirred for 16 hours.

The reaction was cooled and concentrated in vacuo to dryness. The residue was taken up into EtOAc and washed with water. The organic layer was dried (MgSO₄), filtered, and concentrated in vacuo. The residue was purified by silica gel chromatography (0-10% EtOAc/hex over 20 minutes) to provide H1.

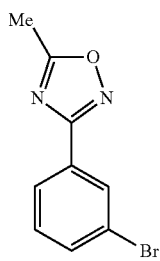

Bromide H2 was prepared in a similar manner to H1 except that acetyl chloride was used instead of cyclopropanecarbonyl chloride in Method H.

Method I

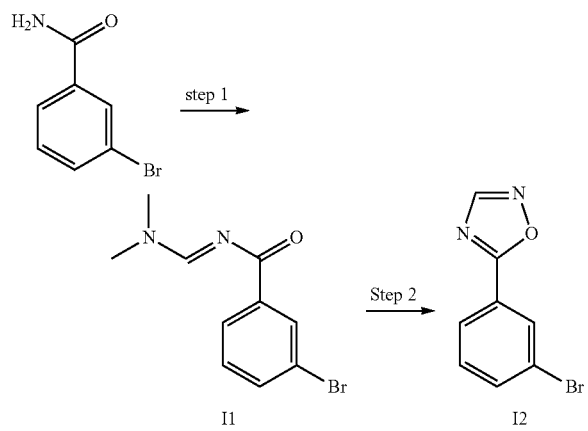

Step 1 To 3-bromobenzamide (0.52 g, 2.6 mmol) was added N,N-dimethylformamide dimethyl acetal (4.2 mL, 31 mmol). The reaction was stirred at 100° C. for 6 h and then concentrated in vacuo to I1 that was carried on directly without purification.

Step 2 To I1 prepared in step 1 (0.66 g, 2.6 mmol) in dioxane (2.8 mL) and water (2 mL) was added hydroxylamine hydrochloride (0.23 g, 3.4 mmol), sodium hydroxide (0.14 g, 3.4 mmol), and acetic acid (3.9 mL, 68 mmol). The reaction was warmed to 90° C. and stirred for 7 hours. The cooled reaction mixture was concentrated in vacuo. The residue was taken up into DCM and washed with saturated NaHCO₃. The organic layer was dried (MgSO₄), filtered, and concentrated in vacuo. The residue was purified by silica gel chromatography (0-20% EtOAc/hex over 20 minutes) to provide I2.

Method J

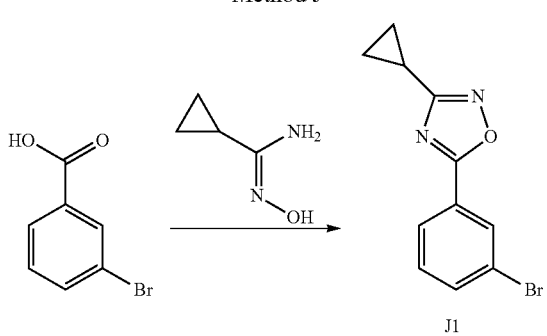

To 3-bromobenzoic acid (3.0 g, 15 mmol) in EtOAc (50 mL) was added N'-hydroxycyclopropanecarboximidamide (1.5 g, 15 mmol), TEA (6.2 mL, 45 mmol). T3P (50% solution in EtOAc, 22 mL, 37 mmol) was slowly added at room temperature. The reaction mixture was warmed to 80° C. and stirred for 5 hours. The cooled reaction mixture was poured into water and the mixture was extracted with EtOAc. The combined organic layers were washed with saturated NaHCO₃ and brine. The organic layer was dried (MgSO₄), filtered, and concentrated in vacuo to provide J1.

Bromide J2 was prepared in a similar manner to J1 in Method J except that 4-bromopicolinic acid was used instead of 3-bromobenzoic acid.

Method K

Step 1: To 3-bromobenzoic acid (2.0 g, 10 mmol) in EtOAc (50 mL) was added cyclopropanecarbohydrazide (1.0 g, 10 mmol), TEA (2.8 mL, 20 mmol), and T3P (50% solution in EtOAc, 8.9 mL, 15 mmol). The reaction mixture was warmed to 80° C. and stirred for 36 h. To the cooled reaction was added water. The mixture was extracted with EtOAc. The combined organics were washed with water and brine, dried (MgSO$_4$), filtered, and concentrated in vacuo. The residue was triturated with DCM to provide K1.

Step 2:

To K1 (0.14 g, 0.50 mmol) in THF (2.5 mL) was added Burgess reagent (0.36 g, 1.5 mmol). The reaction was warmed to 75° C. and stirred for 2 h. The reaction was concentrated in vacuo and the residue was purified by silica gel chromatography (0-30% EtOAc/hex over 30 minutes) to provide K2.

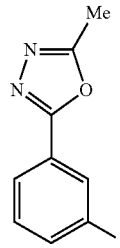

K3

The oxadiaozle K3 was prepared in a similar manner as K2 in Method K except that acetohydrazide was used instead of cyclopropanecarbohydrazide in step 1.

Method L

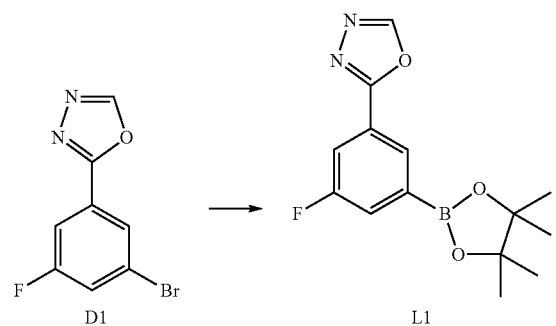

D1      L1

Step 2: To the bromide D1 (1.7 g, 7.1 mmol) in THF (8.9 mL) was added bis(pinacolato)-diboron (2.1 g, 8.3 mmol), 1,3-bis-(diisopropylphenyl)-imidazolium chloride (0.18 g, 0.43 mmol), palladium acetate (0.05 g, 0.2 mmol) and potassium acetate (1.7 g, 17.8 mmol). Nitrogen was bubbled through the reaction mixture for 5 minutes. The reaction was then warmed to reflux and stirred for 2 h. The cooled mixture was passed through a pad of silica gel. The filtrate was concentrated in vacuo and the residue was purified by silica gel chromatography (0-30% EtOAc/hex) to provide the boronate ester L1.

Method M

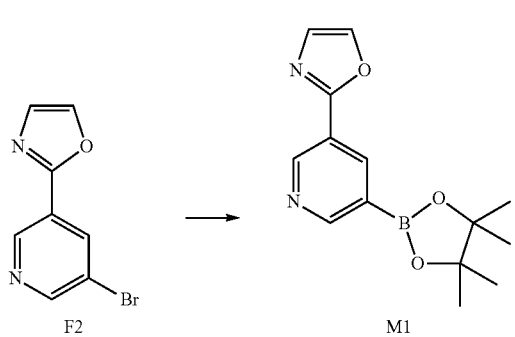

F2      M1

To the bromide F2 (0.50 g, 2.2 mmol) in DMSO (7.4 mL) was added Bis(pinacolato)diboron and potassium acetate (0.65 g, 6.7 mmol). Nitrogen was bubble through the reaction for 10 minutes after which PdCl$_2$(dppf) (0.08 g, 0.11 mmol) was added. Nitrogen was bubbled through the reaction for another 5 minutes after which the reaction was warmed to 80° C. and stirred for 16 h. Water was added to the cooled reaction mixture and the mixture was extracted with EtOAc. The combined organic layers were washed with water and brine, dried (MgSO$_4$), filtered, and concentrated in vacuo. The residue was purified by silica gel chromatography (0-10% MeOH/EtOAc over 30 minutes) to provide M1.

TABLE 3

The following bromides in Table 3 were converted to the boronate ester using Method L or Method M

| Bromide | Method | Boronate Ester | Bromide | Method | Boronate Ester |
|---------|--------|----------------|---------|--------|----------------|
| D2 | M | M2 | E1 | L | L7 |

TABLE 3-continued
The following bromides in Table 3 were converted to the boronate ester using Method L or Method M
| Bromide | Method | Boronate Ester | Bromide | Method | Boronate Ester |
|---|---|---|---|---|---|
| 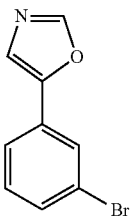 [SMILES: Brc1cccc(-c2cnco2)c1] Aldrich | L | 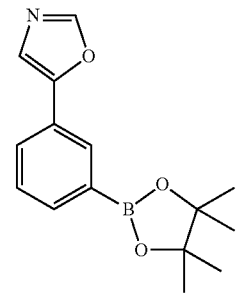 L2 | 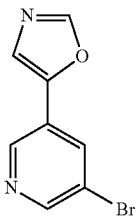 E2 | M | 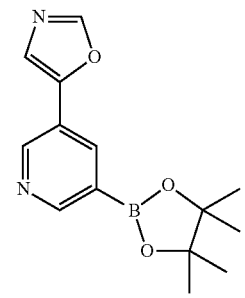 M8 |
| 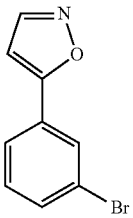 [SMILES: Brc1cccc(-c2ccno2)c1] Aldrich | M | 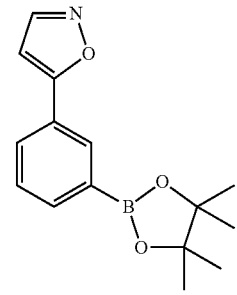 M3 | 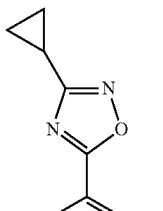 J1 | L | 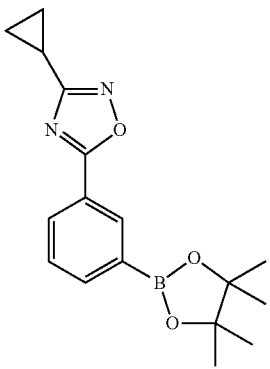 L8 |
| 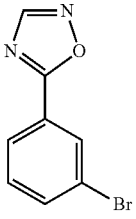 [SMILES: Brc1cccc(-c2ncno2)c1] I2 | L | 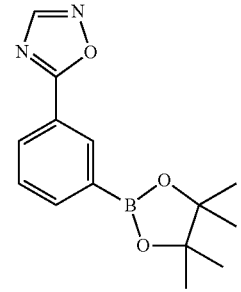 L3 | 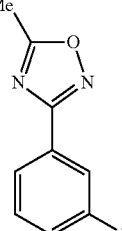 H2 | L | 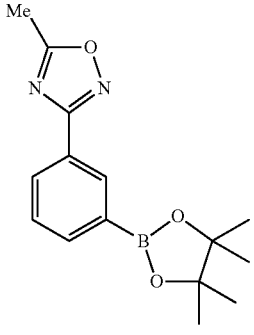 L9 |
| 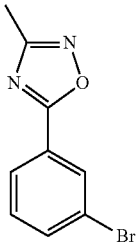 G1 | L | 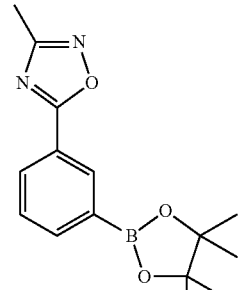 L4 | 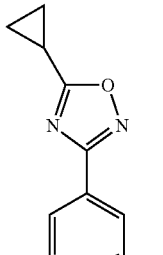 H1 | L | 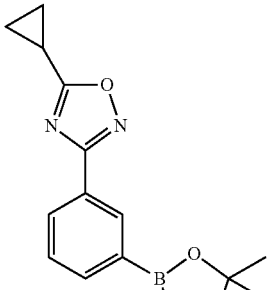 L10 |

TABLE 3-continued
The following bromides in Table 3 were converted to the boronate ester using Method L or Method M
| Bromide | Method | Boronate Ester | Bromide | Method | Boronate Ester |
|---|---|---|---|---|---|
| 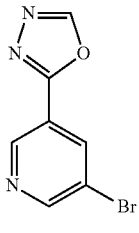 D5 | M | 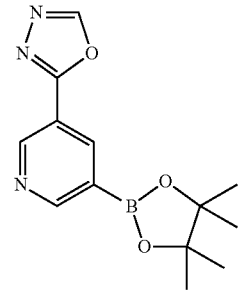 M4 | 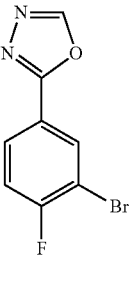 D6 | M | 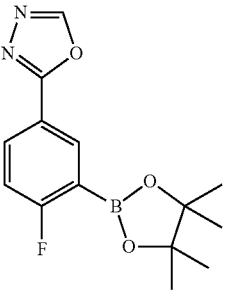 M9 |
| 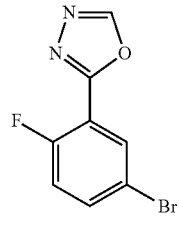 D3 | M | 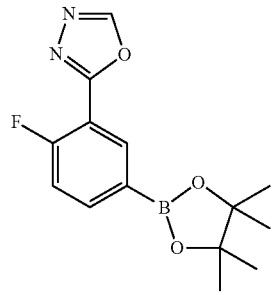 M5 |  D4 | M | 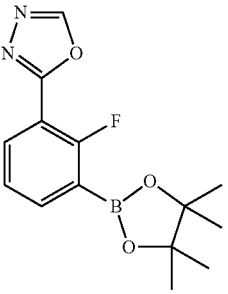 M10 |
| 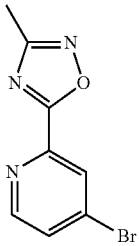 G2 | M | 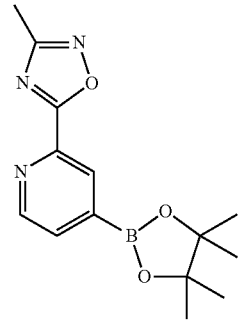 M6 | 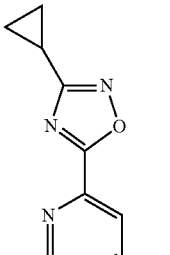 J2 | M | 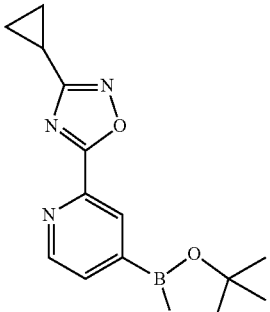 M11 |
| 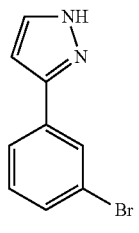 | L | 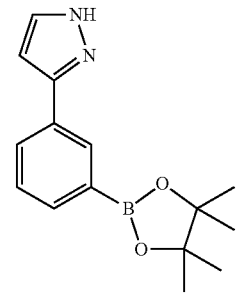 L5 | 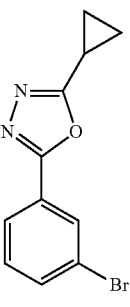 K2 | L | 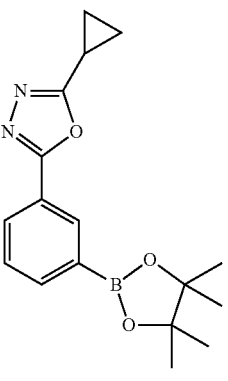 L11 |

TABLE 3-continued

The following bromides in Table 3 were converted to the boronate ester using Method L or Method M

| Bromide | Method | Boronate Ester | Bromide | Method | Boronate Ester |
|---|---|---|---|---|---|
| K3 | L | L6 | | L | L12 |
| F2 | M | M7 | | | |

Method N

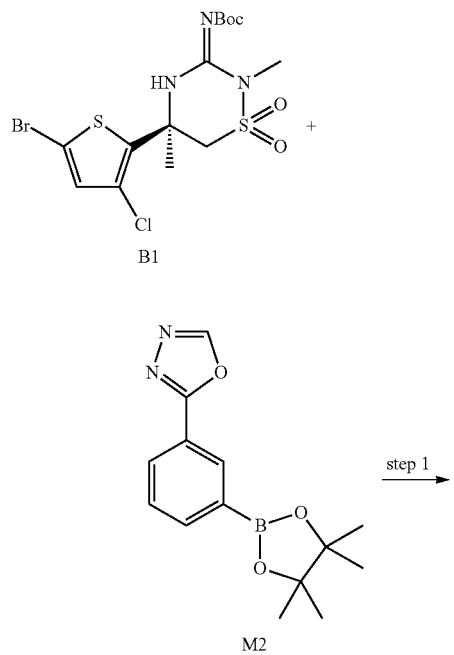

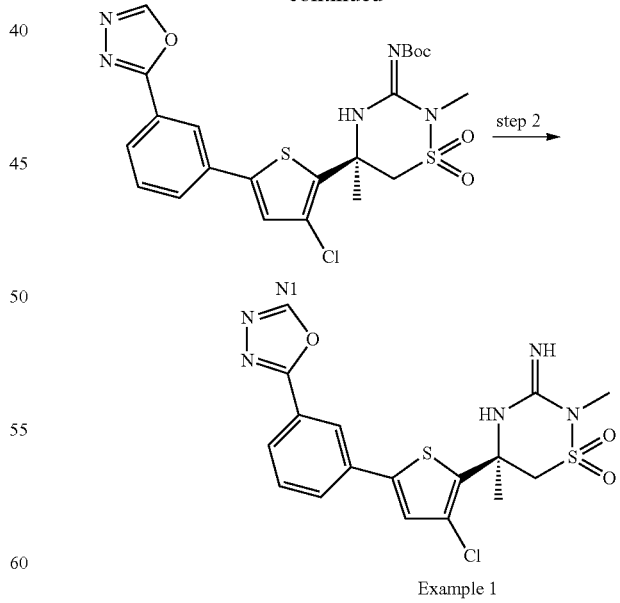

Example 1

Step 1: To the bromide B1 (0.21 g, 0.44 mmol) in t-butanol (1.5 mL) was added the boronate ester M2 (0.22 g, 0.79 mmol) followed by potassium carbonate (2.0 M, 0.33 mL, 0.66 mmol). Nitrogen was bubbled through the reaction mixture for 5 minutes. PdCl$_2$(dppf) (0.064 g, 0.088 mmol) and nitrogen was bubbled through the mixture for 5 minutes. The reaction was warmed to 65° C. and stirred for 3 h. To the cooled reaction mixture was added water. The mixture was extracted with EtOAc. The combined organics were washed with water and brine, dried (MgSO$_4$), filtered, and concentrated in vacuo. The residue was taken up into DCM (2 mL) and (Boc)$_2$O (0.14 g, 0.66 mmol) was added. The reaction was stirred at room temperature for 12 h. The reaction was loaded directly onto a silica gel column and dried with nitrogen gas. The substrate was purified by eluting with 0-50% EtOAc/hex over 30 minutes to provide N1.

Step 2: To N1 (0.21 g, 0.39 mmol) in DCM (1.2 mL) was added TFA (0.6 mL). The reaction was stirred at room temperature for 2 h and then concentrated in vacuo. The residue was taken up into DCM and washed with saturated NaHCO$_3$, water, and brine. The organic layer was dried (MgSO$_4$), filtered, and concentrated in vacuo to provide a foam. The foam was purified by reverse phase chromatography using a Biotage SP1 system (Varian SuperFlash C18 SF25-55 g: 5% (2 column volumes), 5-100% (10 column volumes) 0.1% formic acid/acetonitrile//0.1% formic acid/water) to provide Example 1.

TABLE 4

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 1 | B1 | M2 | | 438 (438) | B 1.49 | 1.6 |
| 2 | B2 | M2 | | 422 (422) | A 1.98 | 1.7 |

TABLE 4-continued
Using the procedure described in Method N, the following examples were prepared utilizing the appropriate bromide and boronate ester.
| Ex. # | Bromide | Boronate Ester | Example | M + H Obs. (Exp) | LCMS Cond. ($t_R$ min) | BACE1 Ki (nM) |
|---|---|---|---|---|---|---|
| 3 | 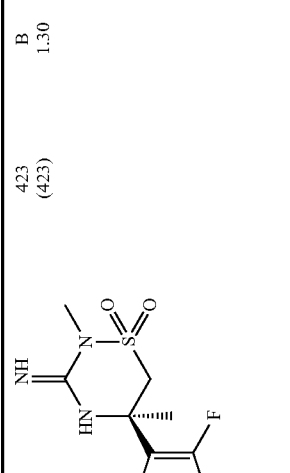 B2 | 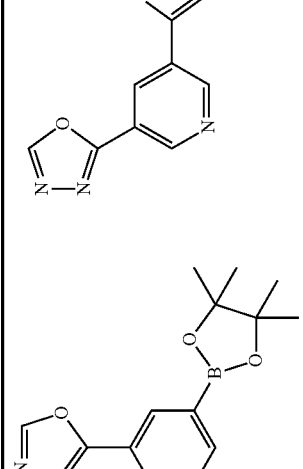 M4 | 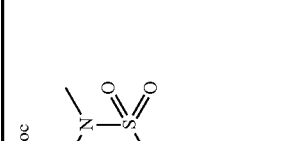 | 423 (423) | B 1.30 | 7.5 |
| 4 | 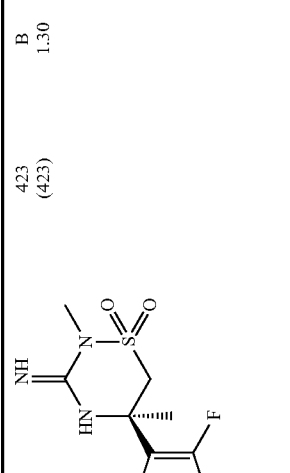 B2 | 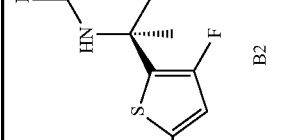 L5 | 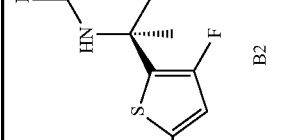 | 420 (420) | B 1.52 | 10.7 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 5 | B1 | M4 | | 439 (439) | B 1.38 | 3.7 |
| 6 | B1 | L12 | | 437 (437) | A 2.06 | 4.7 |
| 7 | B2 | L12 | | 421 (421) | A 2.03 | 8.7 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 8 | A16 | L12 | | 415 (415) | A 2.05 | 1951 |
| 9 | B1 | M7 | | 438 (438) | B 1.45 | 6.9 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 10 | B2 | M7 | | 422 (422) | A 1.91 | 15.7 |
| 11 | B1 | L2 | | 437 (437) | A 2.07 | 1.7 |
| 12 | B2 | L2 | | 421 (421) | A 2.04 | 3.3 |

TABLE 4-continued
Using the procedure described in Method N, the following examples were prepared utilizing the appropriate bromide and boronate ester.
| Ex. # | Bromide | Boronate Ester | Example | M + H Obs. (Exp) | LCMS Cond. ($t_R$ min) | BACE1 Ki (nM) |
|---|---|---|---|---|---|---|
| 13 | 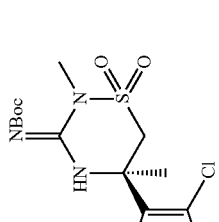 B1 | 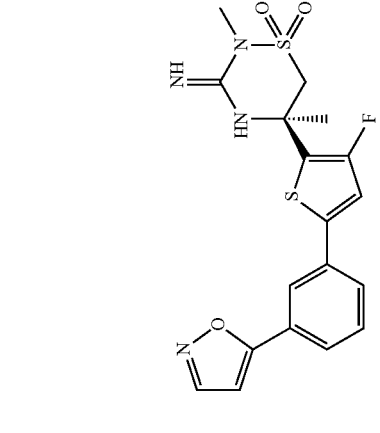 M3 | 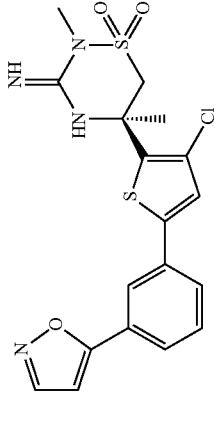 | 437 (437) | A 2.11 | 6.5 |
| 14 | 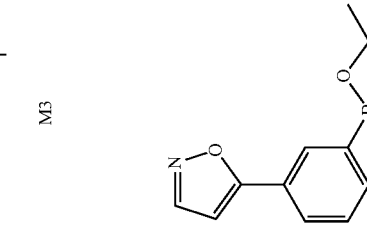 B2 | 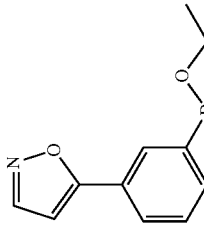 M3 | 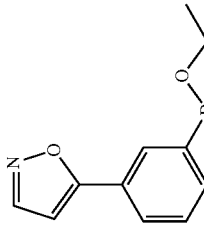 | 421 (421) | A 2.07 | 6.9 |

TABLE 4-continued
Using the procedure described in Method N, the following examples were prepared utilizing the appropriate bromide and boronate ester.
| Ex. # | Bromide | Boronate Ester | Example | M + H Obs. (Exp) | LCMS Cond. ($t_R$ min) | BACE1 Ki (nM) |
|---|---|---|---|---|---|---|
| 15 | 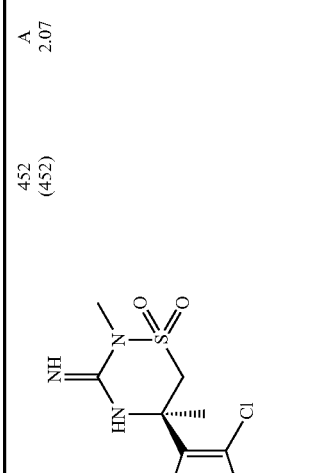 B1 | 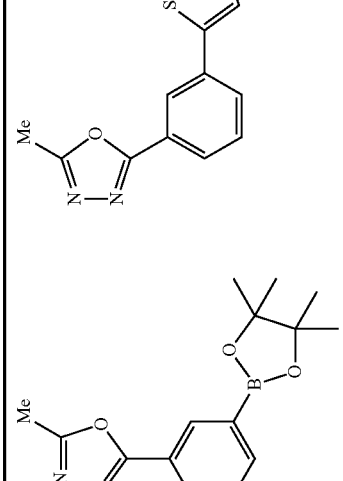 L6 | 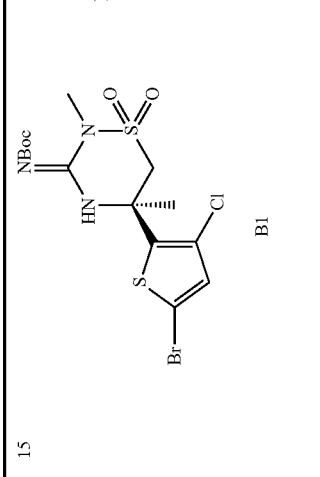 | 452 (452) | A 2.07 | 129 |
| 16 |  B2 | 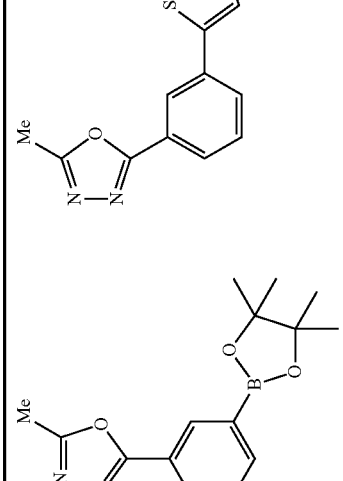 L6 | 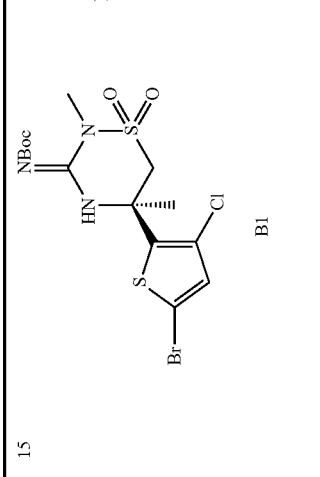 | 436 (436) | A 2.03 | 232 |

TABLE 4-continued
Using the procedure described in Method N, the following examples were prepared utilizing the appropriate bromide and boronate ester.
| Ex. # | Bromide | Boronate Ester | Example | M + H Obs. (Exp) | LCMS Cond. ($t_R$ min) | BACE1 Ki (nM) |
|---|---|---|---|---|---|---|
| 17 | 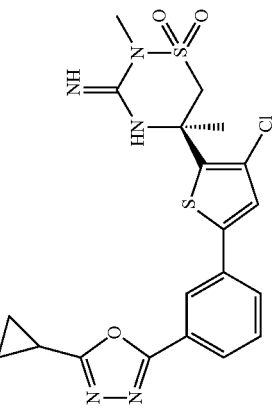 B1 | 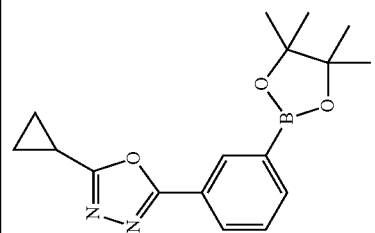 L11 | 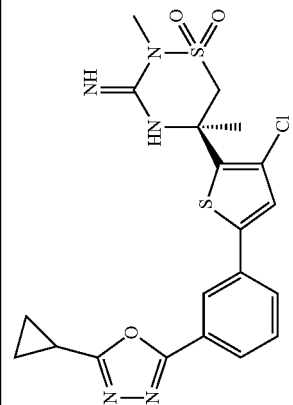 | 478 (478) | A 2.08 | 203 |
| 18 | 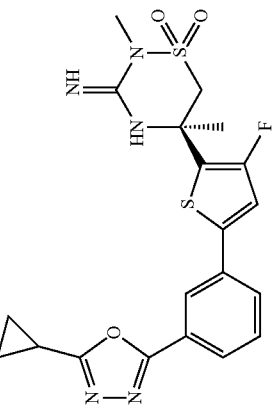 B2 | 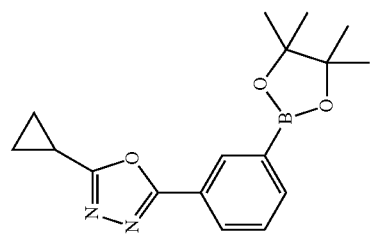 L11 | 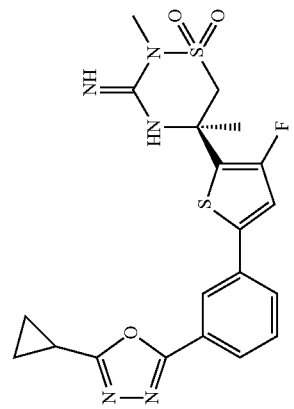 | 462 (462) | A 2.04 | 177 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 19 | A13 | M2 | | 404 (404) | A 1.87 | 19.2 |
| 20 | B1 | M8 | | 438 (438) | B 1.61 | 11.9 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 21 | B2 | M8 | | 422 (422) | B 1.55 | 18.4 |
| 22 | A13 | M8 | | 404 (404) | B 1.45 | 85.9 |
| 23 | B1 | | | 455 (455) | B 1.62 | 11.4 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$, min) | BACE1 Ki (nM) |
|---|---|---|---|---|---|---|
| 24 | A13 | L7 | | 421 (421) | B 1.78 | 81.0 |
| 25 | B2 | L7 | | 439 (439) | B 1.81 | 12.5 |
| 26 | A12 | L12 | | 404 (404) | 1.74 | 43.6 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 27 | A12 | M2 | | 405 (405) | B 1.54 | 13.8 |
| 28 | B1 | L1 | | 456 (456) | B 1.54 | 0.5 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 29 | B2 | L1 | | 440 (440) | B 1.50 | 1.2 |
| 30 | A16 | L1 | | 434 (434) | B 1.52 | 869 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 31 | B1 | M9 | | 456 (456) | B 1.55 | 1.7 |
| 32 | B2 | M9 | | 440 (440) | B 1.50 | 1.1 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 33 | B1 | M5 | | 456 (456) | B 1.52 | 5.5 |
| 34 | B2 | M5 | | 440 (440) | B 1.47 | 6.7 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 35 | B1 | M10 | | 456 (456) | B 1.51 | 60.7 |
| 36 | B2 | M10 | | 440 (440) | B 1.46 | 1149 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. (t_R min) | BACE1 Ki (nM) |
|---|---|---|---|---|---|---|
| 37 | B1 | L4 | | 452 (452) | B 1.66 | 25.9 |
| 38 | B2 | L4 | | 436 (436) | B 1.61 | 29.1 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 39 | B1 | M11 | | 478 (478) | B 1.78 | 419 |
| 40 | B2 | M11 | | 462 (462) | B 1.73 | 623 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. (t$_R$ min) | BACE1 Ki (nM) |
|---|---|---|---|---|---|---|
| 41 | B1 | L9 | | 452 (452) | B 1.67 | 13.4 |
| 42 | B2 | L9 | | 436 (436) | B 1.62 | 25.4 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 43 | A13 | L1 | | 422 (422) | B 1.49 | 8.8 |
| 44 | B1 | L10 | | 462 (462) | B 1.79 | 267 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 45 | B2 | L10 | | 462 (462) | B 1.74 | 323 |
| 46 | B1 | | | 438 (438) | B 1.62 | 3.3 |
| 47 | B2 | | | 422 (422) | B 1.57 | 3.9 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 48 | B2 | L3 | | 422 (422) | B 1.57 | 0.87 |
| 49 | B1 | M6 | | 453 (453) | B 1.49 | 18.7 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 50 | B2 | M6 | | 437 (437) | B 1.44 | 56.3 |
| 51 | B1 | M11 | | 479 (479) | B 1.56 | 127 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 52 | B2 | M11 | | 463 (463) | B 1.51 | 498 |
| 53 | B1 | L6 | | 452 (452) | B 2.07 | 129 |

TABLE 4-continued

Using the procedure described in Method N, the following examples were prepared utilizing the appropriate bromide and boronate ester.

| Ex. # | Bromide | Boronate Ester | Example | M + H Obs. (Exp) | LCMS Cond. ($t_R$ min) | BACE1 Ki (nM) |
|---|---|---|---|---|---|---|
| 54 | B2 | | | 431 (431) | B 1.16 | 132 |
| 55 | B2 | | | 433 (433) | B 1.34 | 1252 |

TABLE 4-continued
Using the procedure described in Method N, the following examples were prepared utilizing the appropriate bromide and boronate ester.
| Ex. # | Bromide | Boronate Ester | Example | M + H Obs. (Exp) | LCMS Cond. ($t_R$ min) | BACE1 Ki (nM) |
|---|---|---|---|---|---|---|
| 56 | 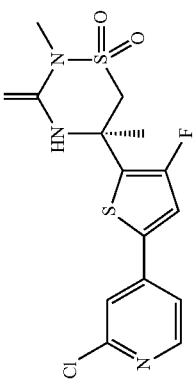 | 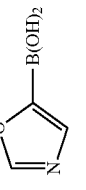 | 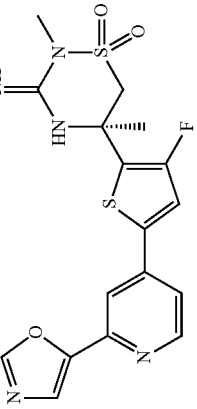 | 422 (422) | B 1.73 | 23.5 |

113
Method O

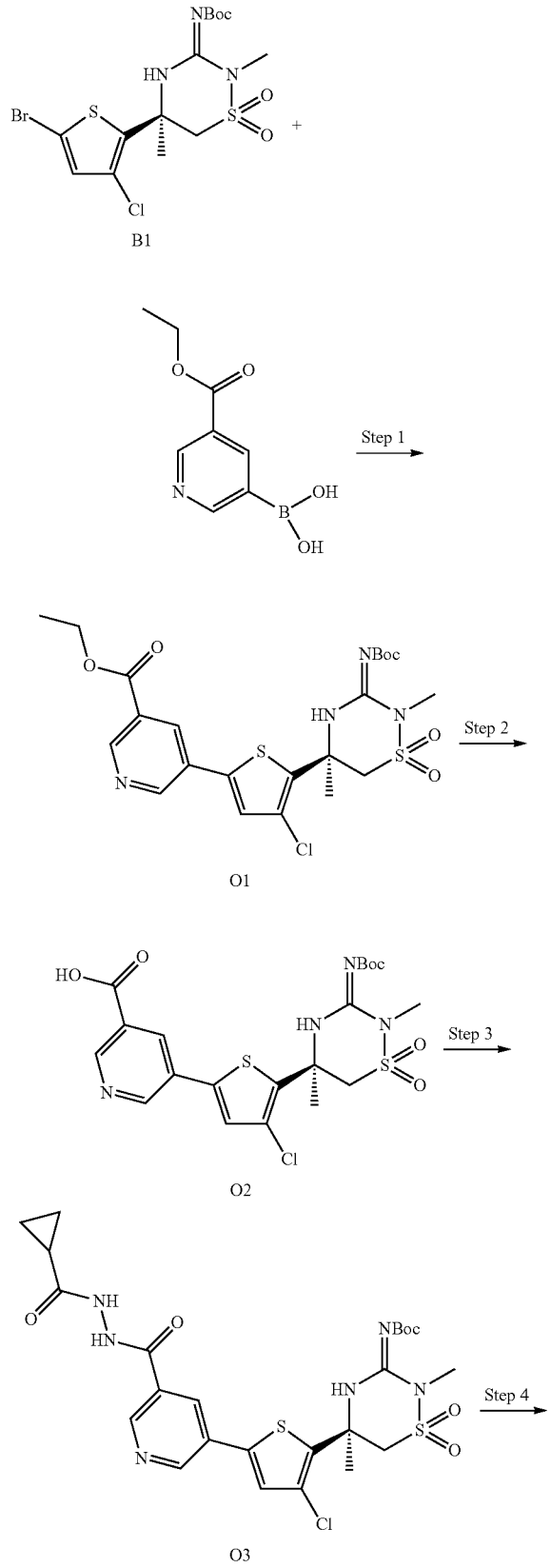

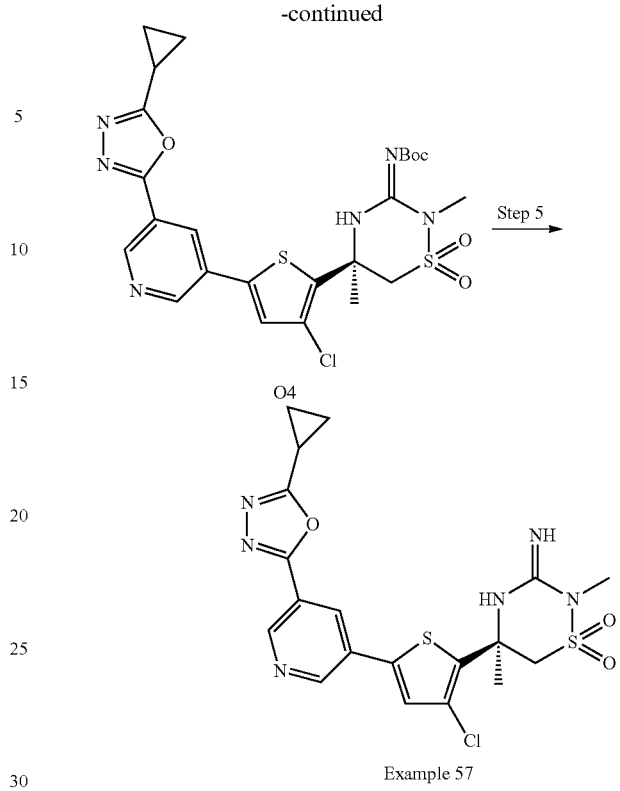

Example 57

Step 1: To B1 (1.0 g, 2.2 mmol) in t-butanol (7.4 mL) was added (5-(ethoxycarbonyl)pyridin-3-yl)boronic acid (0.78 g, 4.0 mmol) followed by aqueous 2 M $K_2CO_3$ (1.7 mL, 3.3 mmol). Nitrogen was bubbled through the reaction mixture for 5 minutes after which $PdCl_2$(dppf) (0.32 g, 0.44 mmol) was added. Nitrogen was bubbled through the reaction mixture for 5 additional minutes. The reaction was heated to 65° C. and stirred for 3 h. EtOAc was added to the cooled reaction. The mixture was washed with water and brine. The organic layer was dried ($MgSO_4$), filtered, and concentrated in vacuo. The residue was taken up into DCM (7 mL) and $(Boc)_2O$ (0.73 g, 3.3 mmol) was added. The reaction was stirred at room temperature for 20 h. The reaction was purified directly by silica gel chromatography (0-40% EtOAc/hex) to provide O1.

Step 2: To O1 (0.96 g, 1.7 mmol) in THF (5.9 mL) was added 2 M LiOH (2.2 mL, 4.4 mmol). The reaction was stirred at room temperature for 2.5 h. The mixture was acidified to pH-5-6 using aqueous saturated citric acid solution. The mixture was extracted with EtOAc. The combined organics were washed with water and brine, dried ($MgSO_4$), filtered, and concentrated in vacuo to provide O2.

Step 3: To O2 (0.20 g, 0.39 mmol) in THF (1.3 mL) was added cyclopropanecarbohydrazide (0.051 g, 0.51 mmol), N,N-diisopropylethylamine (0.15 g, 1.2 mmol) and T3P (50% solution in EtOAc, 0.32 mL, 0.54 mmol). The reaction was stirred at room temperature for 15 h. Water was added and the mixture was extracted with EtOAc. The combined organic layers were washed with water and brine, dried ($MgSO_4$), filtered and concentrated in vacuo to provide O3.

Step 4: To O3 (0.23 g, 0.38 mmol) in THF (1.9 mL) was added Burgess reagent (0.18 g, 0.76 mmol). The mixture was warmed to 80° C. and stirred for 1 h. Water was added to the cooled reaction. The mixture was extracted with EtOAc. The combined organics were washed with water and brine, dried (MgSO₄), filtered, and concentrated in vacuo. The residue was purified by silica gel chromatography (0-60% EtOAc/hex over 30 minutes) to provide O4.

Step 5: To O4 (0.11 g, 0.19 mmol) in DCM (1 mL) was added TFA (0.30 mL, 3.9 mmol). The reaction was stirred at room temperature for 1 h and then concentrated in vacuo. The residue was taken up into DCM and washed with saturated NaHCO₃, water, and brine. The organic layer was dried (MgSO₄), filtered, and concentrated in vacuo. The residue was taken up into DCM and excess 2N HCl in ether was added after which the heterogeneous mixture was concentrated in vacuo to provide Example 57 as the HCl salt.

Example 58 was prepared in the same manner as Example 57 in Method O except that (5-fluoro-2-(methoxycarbonyl)pyridin-4-yl)boronic acid was used instead of (2-(ethoxycarbonyl)pyridin-4-yl)boronic acid in step 1 and formic hydrazide was used instead of cyclopropanecarbohydrazide in step 3.

Example 58

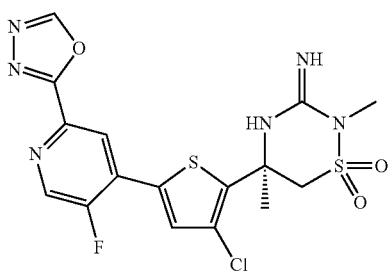

Example 59

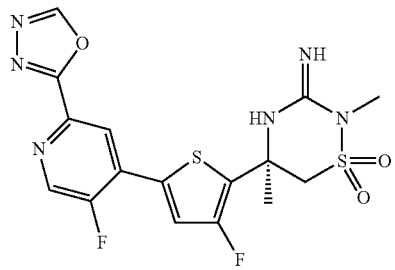

Example 59 was prepared in the same manner as Example 57 in Method O except that (5-fluoro-2-(methoxycarbonyl)pyridin-4-yl)boronic acid was used instead of (2-(ethoxycarbonyl)pyridin-4-yl)boronic acid and B2 was used in stead of B1 in step 1. In step 3, formic hydrazide was used instead of cyclopropanecarbohydrazide.

TABLE 5

| Ex. number | Example | M + H Obs. (Exp) | LCMS Cond. ($t_R$ min) | BACE1 Ki (nM) |
|---|---|---|---|---|
| 57 |  | 479 (479) | A 2.03 | 566.2 |
| 58 | 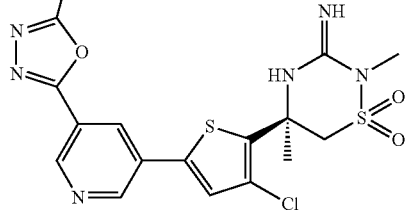 | 457 (457) | B 1.60 | 68.29 |
| 59 | 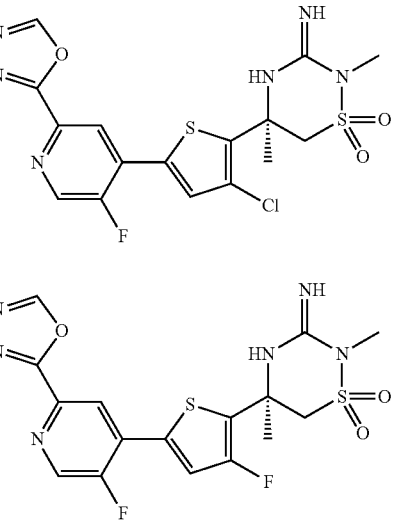 | 441 (441) | B 1.54 | 107 |

Method P

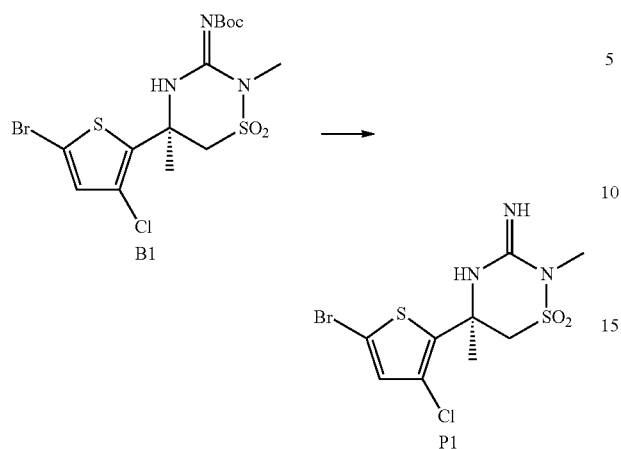

P1 was prepared from B1 using the procedure described in Method O, step 5 with the exception that 2N HCl was not added after neutralization and P1 was obtained in neutral form.

Method Q

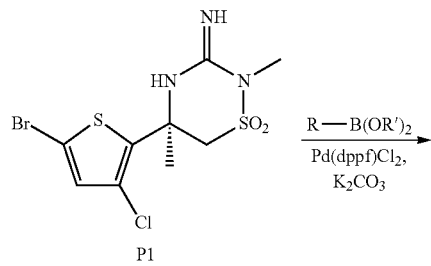

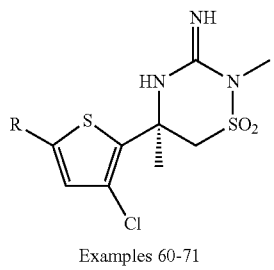

Examples 60-71

Parallel Preparation of Examples 60-71

To a set of microwave vials containing mixtures of reactant P1 (25 mg, 0.067 mmol), the appropriate boronic acid or pinocol ester (1.5 equiv.), and [1,1'-bis(diphenylphosphino)ferrocene]dichloro palladium(II)(9.82 mg, 0.013 mmol) in 1,4-dioxane (2 mL) was added potassium carbonate (27.8 mg, 0.20 mmol) in water (0.20 mL). Reactions were carried out at 120° C. for 20 minutes in a microwave reactor. Water (2 mL) and EtOAc (2 mL) were added, stirred for 10 minutes. The organic layers were separated, transferred to a set of vials, and concentrated. Each crude product was redissolved in 1 mL of DMSO and filtered. The crude products were purified by mass triggered HPLC (Waters XBridge C18 column, 5 μm, 19×100 mm, using gradient ranges from 10-30% initial to 35-98% final MeCN (0.1% NH$_4$OH) in water (0.1% NH$_4$OH) to provide the Examples 60-71.

TABLE 6

Utilizing the procedure described in Method Q, P1 was converted to the following examples using the appropriate boronic acid or boronate ester.

| Example no. | Example | M + H Obs. (Exp) | LCMS Method; ($t_R$ min) | BACE1 Ki (nM) |
|---|---|---|---|---|
| 60 | | 436 (436) | C 0.98 | 57.0 |
| 61 | | 503 (503) | C 0.87 | 693 |

TABLE 6-continued

Utilizing the procedure described in Method Q, P1 was converted to the following examples using the appropriate boronic acid or boronate ester.

| Example no. | Example | M + H Obs. (Exp) | LCMS Method; ($t_R$ min) | BACE1 Ki (nM) |
|---|---|---|---|---|
| 62 | | 446 (446) | C 1.19 | 161 |
| 63 | | 437 (437) | C 1.03 | 30.3 |
| 64 | | 447 (447) | C 0.95 | 2103 |
| 65 | | 447 (447) | C 1.02 | 3520 |
| 66 | | 456 (456) | C 0.89 | 5904 |
| 67 | | 437 (437) | C 1.02 | 2265 |

TABLE 6-continued

Utilizing the procedure described in Method Q, P1 was converted to the following examples using the appropriate boronic acid or boronate ester.

| Example no. | Example | M + H Obs. (Exp) | LCMS Method; ($t_R$ min) | BACE1 Ki (nM) |
|---|---|---|---|---|
| 68 | | 437 (437) | C 0.83 | 429 |
| 69 | | 437 (437) | C 0.96 | 4231 |
| 70 | | 453 (453) | C 1.03 | 827 |
| 71 | | 437 (437) | C 0.84 | 1600 |

Method R

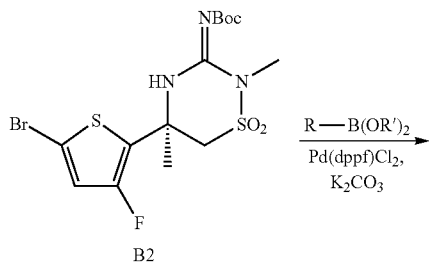

B2

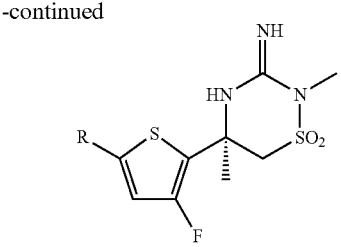

Examples 72-77

Parallel Preparation of Examples 72-77

To a set of microwave vials containing mixtures of reactant B2 (30 mg, 0.066 mmol), the appropriate boronic acid or boronate ester (1.3 equiv.), and [1,1'-bis(diphenylphosphino)

ferrocene]dichloro palladium(II) (9.62 mg, 0.013 mmol) in 1,4-Dioxane (2 mL) was added potassium carbonate (27.3 mg, 0.20 mmol) in water (0.20 mL). Reactions were carried out at 120° C. for 20 minutes in a microwave reactor. Water (2 mL) and EtOAc (2 mL) were added, stirred for 10 minutes. The organic layers were separated, transferred to a set of vials, and concentrated. Each crude product was redissolved in 1 mL of DMSO and filtered. The crude products were purified by mass triggered HPLC (Waters XBridge C18 column, 5 μm, 30×100 mm, using gradient ranges from 10% initial to 52% final MeCN (0.1% NH$_4$OH) in water (0.1% NH$_4$OH) to provide the Examples 72-77.

TABLE 7

Utilizing the procedure described in Method R, B2 was converted to the following examples using the appropriate boronic acid or boronate ester.

| Example no. | Example | M + H Obs. (Exp) | LCMS Method; (t$_R$ min) | BACE1 Ki (nM) |
|---|---|---|---|---|
| 72 | | 435 (435) | C 0.79 | 67.2 |
| 73 | | 432 (432) | C 0.78 | 338 |
| 74 | | 432 (432) | C 0.77 | 199 |
| 75 | | 435 (435) | C 0.79 | 2783 |

TABLE 7-continued

Utilizing the procedure described in Method R, B2 was converted to the following examples using the appropriate boronic acid or boronate ester.

| Example no. | Example | M + H Obs. (Exp) | LCMS Method; ($t_R$ min) | BACE1 Ki (nM) |
|---|---|---|---|---|
| 76 | [structure] | 421 (421) | C 0.74 | 112 |
| 77 | [structure] | 421 (421) | C 0.74 | 162 |

Method S

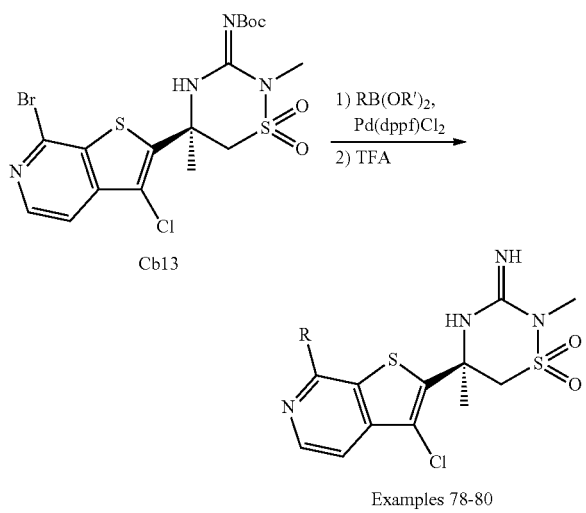

Parallel Preparation of Examples 78-80

To a set of 2-dram vials containing a stir bar was added the appropriate boronic acid/pinacol ester. To each vial was then added PdCl$_2$(dppf)-CH$_2$Cl$_2$ adduct (6.78 mg, 8.30 µmol). The vials were transferred to a glove bag under an atmosphere of nitrogen. To each vial was then added a solution of the bromide Cb13 (29 mg, 0.055 mmol) in Dioxane (1 mL) followed by K$_2$CO$_3$ (1M, 0.166 mL, 0.166 mmol). The vials were capped, removed from the glove bag and placed into a preheated aluminum block at 65° C. The mixtures were stirred at that temperature for 4 hours. To each vial was then added water (2 mL) followed by DCM (2 mL). The mixtures were transferred to a Varian Bond Elute reservoir and the organic layer was drained into a 2-dram vial. To each of the aqueous layers was added additional DCM (1 mL). The organic layer was again drained into the 2-dram vials. The combined organic layers were concentrated in vacuo. Each crude product was redissolved in 1 mL of DMSO and filtered. The crude products were purified by mass triggered HPLC [Waters XBridge C18 column, 5 µm, 19×100 mm, gradient ranges from 15-20% initial to 55-60% final MeCN (0.1% NH$_4$OH) in water (0.1% NH$_4$OH) 50 mL/min, 8 min run time] to provide Examples 78-80.

TABLE 8

| Ex. number | Example | M + H Obs. (Exp) | LCMS Method; ($t_R$ min) | BACE1 Ki (nM) |
|---|---|---|---|---|
| 78 | [structure] | 463.10 (463) | C (0.91) | 162 |

TABLE 8-continued

| Ex. number | Example | M + H Obs. (Exp) | LCMS Method; ($t_R$ min) | BACE1 Ki (nM) |
|---|---|---|---|---|
| 79 | 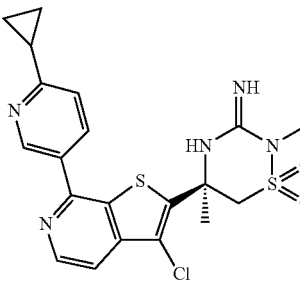 | 462.10 (462) | C (0.94) | 282 |
| 80 | 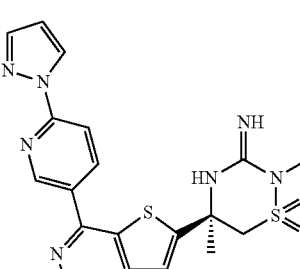 | 488.10 (488) | C (0.97) | 10 |

Method T

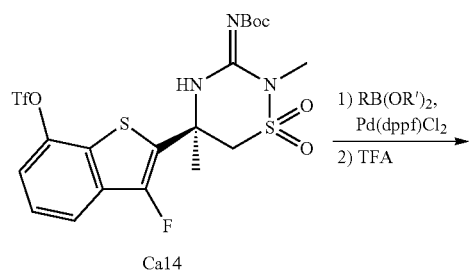

Ca14

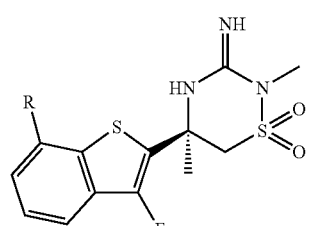

Examples 81-89

Parallel Preparation of Examples 81-89

To a set of 2-dram vials containing a stir bar was added the appropriate boronic acid/pinacol ester. To each vial was then added PdCl$_2$(dppf)-CH$_2$Cl$_2$ adduct (6.78 mg, 8.30 μmol). The vials were transferred to a glove box under an atmosphere of nitrogen. To each vial was then added a solution of the triflate Ca14 (29 mg, 0.055 mmol) in Dioxane (1 mL) followed by K$_2$CO$_3$ (1M, 0.166 mL, 0.166 mmol). The vials were capped then removed from the glove bag and placed into a preheated aluminum block at 65° C. The mixtures were stirred at that temperature for 4 hours. To each vial was added water (2 mL) to followed by DCM (2 mL). The mixtures were transferred to a Varian Bond Elute reservoir and the organic layer was drained into a 2-dram vial. To each of the aqueous layers was added additional DCM (1 mL). The organic layer was again drained into the 2-dram vials. The combined organic layers were concentrated in vacuo. Each crude product was redissolved in 1 mL of DMSO and filtered. The crude products were purified by mass triggered HPLC using the following conditions: [Waters Sunfire C18 column, 5 μm, 19×100 mm, gradient elution range from 10-15% initial to 35-55% final MeCN (0.1% TFA) in water (0.1% TFA) 50 mL/min, 8 min run time.] Examples 81-89 were repurified by mass triggered HPLC using the following conditions: [Waters XBridge C18 column, 5 μm, 19×100 mm, gradient ranges from 25-30% initial to 65-70% final MeCN (0.1% NH$_4$OH) in water (0.1% NH$_4$OH) 50 mL/min, 8 min run time].

TABLE 9
| Ex. number | Example | M + H Obs. (Exp) | LCMS Method; ($t_R$ min) | BACE1 Ki (nM) |
|---|---|---|---|---|
| 81 | 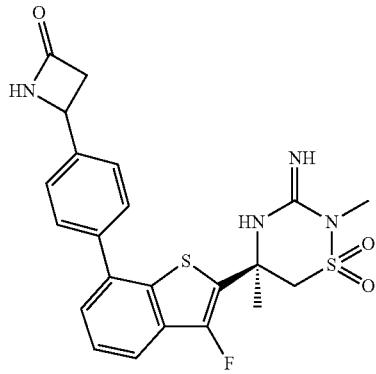 [SMILES: CN1C(=N)N[C@](C)(c2sc3c(-c4ccc(C5CC(=O)N5)cc4)cccc3c2F)CS1(=O)=O] | 473 | C (0.91) | 184.0 |
| 82 | 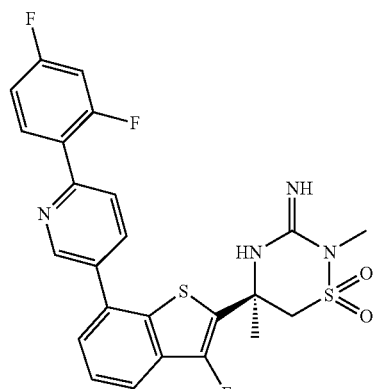 | 517 | C (1.16) | 93.0 |
| 83 | 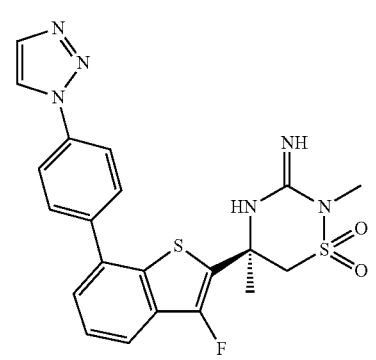 [SMILES: CN1C(=N)N[C@](C)(c2sc3c(-c4ccc(-n5ccnn5)cc4)cccc3c2F)CS1(=O)=O] | 471 | C (0.96) | 19.0 |
| 84 | 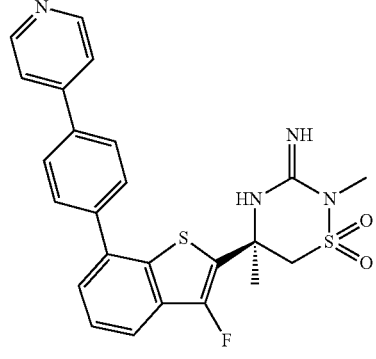 [SMILES: CN1C(=N)N[C@](C)(c2sc3c(-c4ccc(-c5ccncc5)cc4)cccc3c2F)CS1(=O)=O] | 481 | C (1.04) | 351.0 |

TABLE 9-continued

| Ex. number | Example | M + H Obs. (Exp) | LCMS Method; ($t_R$ min) | BACE1 Ki (nM) |
|---|---|---|---|---|
| 85 | | 537 | C (0.97) | 6521.0 |
| 86 | | 484 | C (0.94) | 5616.0 |
| 87 | | 471 | C (1.04) | 10.0 |
| 88 | | 496 | C (1.12) | 9135.0 |

TABLE 9-continued

| Ex. number | Example | M + H Obs. (Exp) | LCMS Method; ($t_R$ min) | BACE1 Ki (nM) |
|---|---|---|---|---|
| 89 | | 470 | C (1.05) | 37.0 |

Method U

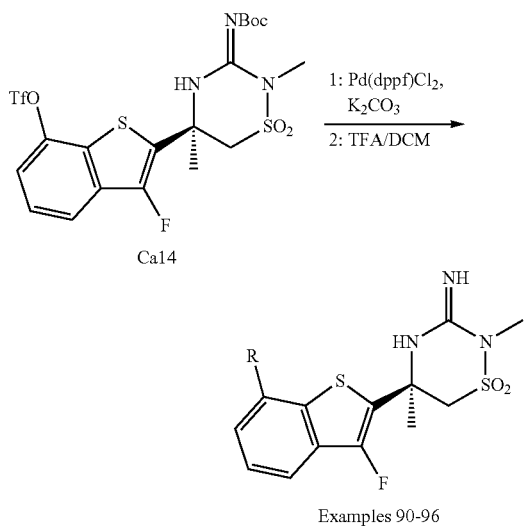

Parallel Preparation of Examples 90-96

To a set of vials containing mixtures of reactant Ca14 (30 mg, 0.052 mmol), boronic acid or boronate ester (1.5 equiv.), and [1,1'-bis(diphenylphosphino)ferrocene]dichloro palladium(II) (7.6 mg, 0.010 mmol) in 1,4-dioxane (2 mL) were added potassium carbonate (21.6 mg, 0.16 mmol) in water (0.16 mL). Reactions were carried out at 120° C. for 20 minutes in a microwave reactor. Water (2 mL) and EtOAc (2 mL) were added, stirred for 10 minutes. The organic layers were separated and concentrated, then added 1 mL of $CH_2Cl_2$ and 0.3 mL of TFA. The reaction mixtures were stirred for 3 hour, concentrated. Each crude product was redissolved in 1 mL of DMSO and filtered. The crude products were purified by mass triggered HPLC (Waters Sunfire C18 column, 5 μm, 19×100 mm, using gradient from 15% to 50% MeCN (0.1% Formic acid) in water (0.1% Formic acid); Waters XBridge C18 column, 5 μm, 19×100 mm, using gradient ranges from 20-45% initial to 60-90% final MeCN (0.1% $NH_4OH$) in water (0.1% $NH_4OH$) to provide the Examples 90-96.

TABLE 10

| Example no. | Example | M + H Obs. (Exp) | LCMS Method; ($t_R$ min) | BACE1 Ki (nM) |
|---|---|---|---|---|
| 90 | | 471 (471) | C 1.05 | 104 |

TABLE 10-continued

| Example no. | Example | M + H Obs. (Exp) | LCMS Method; ($t_R$ min) | BACE1 Ki (nM) |
|---|---|---|---|---|
| 91 | | 487 (487) | C 1.11 | 797 |
| 92 | | 471 (471) | C 1.31 | 1658 |
| 93 | | 503 (503) | C 0.97 | 3840 |
| 94 | | 490 (490) | C 0.99 | 1500 |

TABLE 10-continued

| Example no. | Example | M + H Obs. (Exp) | LCMS Method; ($t_R$ min) | BACE1 Ki (nM) |
|---|---|---|---|---|
| 95 | | 502 (502) | C 1.04 | 9756 |
| 96 | | 445 (445) | C 1.03 | 327 |

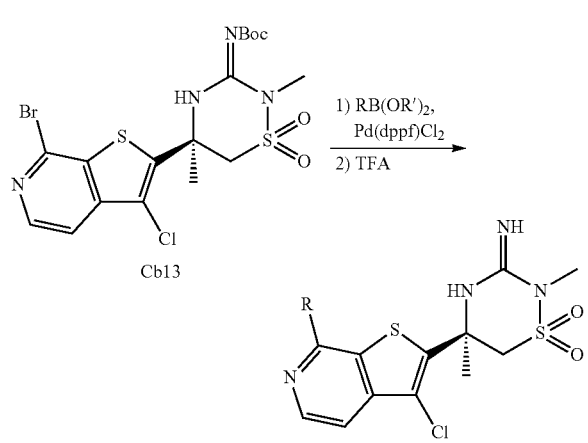

Examples 97-106

Parallel Preparation of Examples 97-106

Examples 97-106 were prepared using a procedure similar to that described in Scheme S. Examples 97 and 98 were isolated after the crude residues were purified by mass triggered preparative HPLC [Waters XBridge C18 column, 5 μm, 19×100 mm, using a gradient range from 15% initial to 60-70% final MeCN (0.1% NH$_4$OH) in water (0.1% NH$_4$OH), 50 mL/min, 8 min run]. Examples 99-106 were isolated after the crude residues were purified by mass triggered preparative HPLC [Waters Sunfire C18 column, 5 μm, 19×100 mm, using a gradient from 15% to 50% MeCN (0.1% TFA) in water (0.1% TFA), 50 mL/min, 8 min run].

TABLE 11

| Example no. | Example | LCMS M + H Obs. | Method; ($t_R$ min) | BACE1 Ki (nM) |
|---|---|---|---|---|
| 97 | | 489.1 | C (0.92) | 61.2 |
| 98 | | 555.1 | C (1.07) | 424.7 |
| 99 | | 488.1 | C (1.05) | 224 |
| 100 | | 488.1 | C (1.00) | 115.7 |

TABLE 11-continued
| Example no. | Example | LCMS M + H Obs. | Method; ($t_R$ min) | BACE1 Ki (nM) |
|---|---|---|---|---|
| 101 | 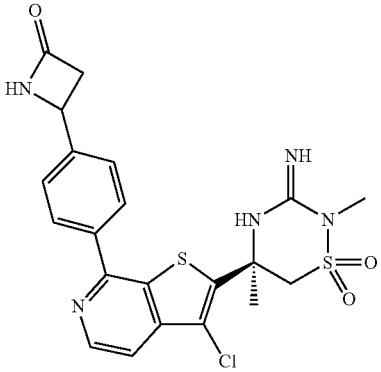 [SMILES: CN1C(=N)N[C@](C)(c2sc3c(-c4ccc(C5CC(=O)N5)cc4)nccc3c2Cl)CS1(=O)=O] | 490.1 | C (0.85) | 959.2 |
| 102 | 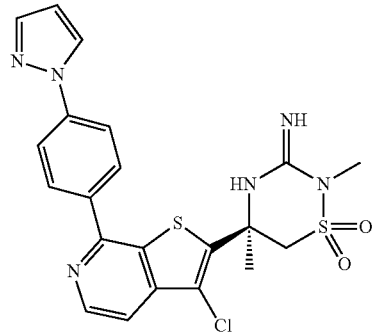 [SMILES: CN1C(=N)N[C@](C)(c2sc3c(-c4ccc(-n5cccn5)cc4)nccc3c2Cl)CS1(=O)=O] | 487.1 | C (0.99) | 29.86 |
| 103 | 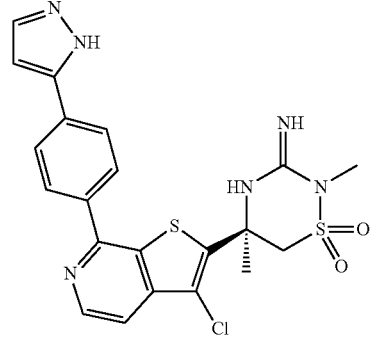 [SMILES: CN1C(=N)N[C@](C)(c2sc3c(-c4ccc(-c5ccn[nH]5)cc4)nccc3c2Cl)CS1(=O)=O] | 451.1 | C (0.92) | 35.55 |

TABLE 11-continued
| Example no. | Example | LCMS M + H Obs. | Method; ($t_R$ min) | BACE1 Ki (nM) |
|---|---|---|---|---|
| 104 | 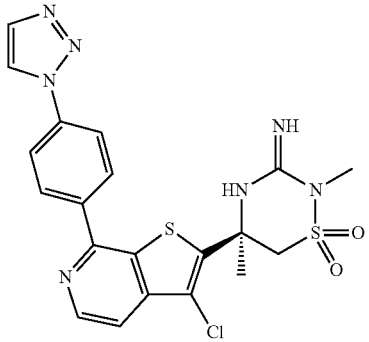 [SMILES: CN1C(=N)N[C@](C)(c2sc3c(-c4ccc(-n5ccnn5)cc4)nccc3c2Cl)CS1(=O)=O] | 488.1 | C (0.91) | 86.07 |
| 105 | 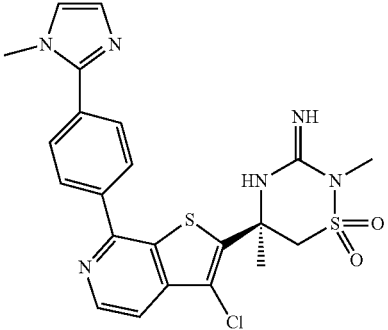 [SMILES: CN1C(=N)N[C@](C)(c2sc3c(-c4ccc(-c5nccn5C)cc4)nccc3c2Cl)CS1(=O)=O] | 501.1 | C (0.88) | 1639 |
| 106 | 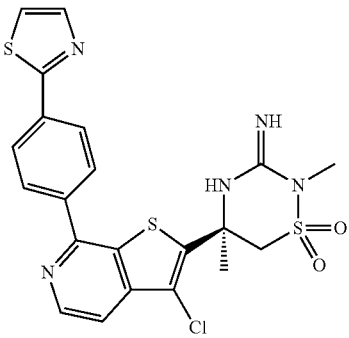 [SMILES: CN1C(=N)N[C@](C)(c2sc3c(-c4ccc(-c5nccs5)cc4)nccc3c2Cl)CS1(=O)=O] | 504.0 | C (1.04) | 270.3 |

Method W

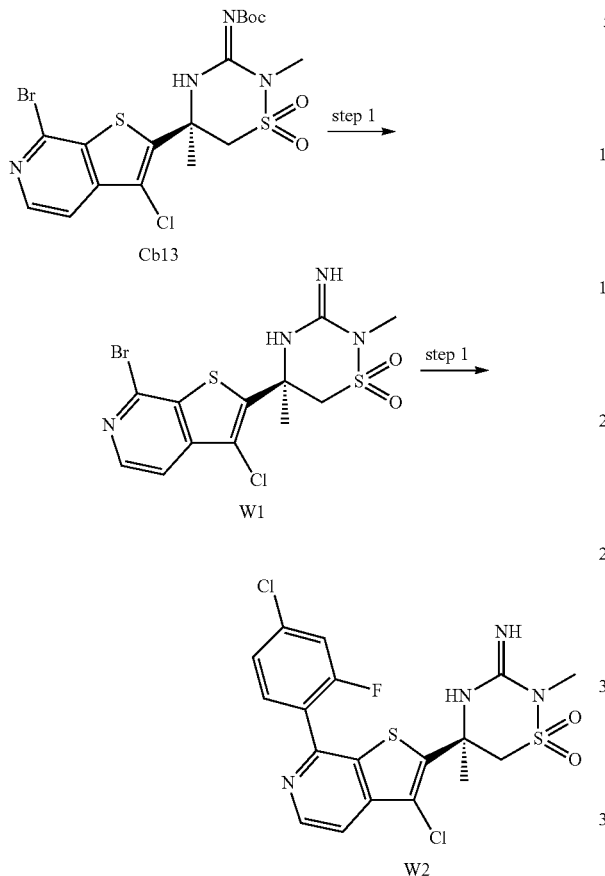

Step 1: To a solution of Cb13 (4.0 g, 7.6 mmol) in DCM (150 mL) was added TFA (15 mL) and the resultant solution was stirred at RT for 16 hours. After that time, the solution was concentrated in vacuo. The residue was partitioned between DCM and sat. NaHCO$_3$$_{(aq.)}$. The layers were separated. The aqueous layer was extracted with EtOAc. The combined organic layers were dried over Na$_2$SO$_4$, filtered and concentrated to afford W1.

Step 2: A mixture of W1 (1.7 g, 4.0 mmol) and (4-chloro-2-fluorophenyl)boronic acid (0.84 g, 4.8 mmol) in dioxane (150 mL) was degassed by bubbling nitrogen through it for 5 min. To the mixture was then added Pd(dppf)Cl$_2$-DCM adduct (0.15 g, 0.20 mmol) followed by an aqueous solution of K$_2$CO$_3$ (2 M, 6.0 mL, 12 mmol). The resultant mixture was heated to 65° C. with stirring overnight. After that time, the mixture was allowed to cool to RT. The mixture was then washed with sat. NaHCO$_3$$_{(aq.)}$. The aqueous layer was extracted with DCM. The combined organic layers were dried over Na$_2$SO$_4$, filtered and concentrated. The crude residue was purified via flash chromatography [SiO$_2$, gradient elution 0-20% MeOH (with 30% conc. NH$_4$OH) in DCM] followed by further purification via SFC (Berger Multigram SFC, column: Princeton Chromatography CN, 20×250 mm, solvent: 20% MeOH (0.1% NH$_4$OH)/CO$_2$, 50 mL/min, 100 bar, 35° C., UV 230 nm. to afford W2.

Method X

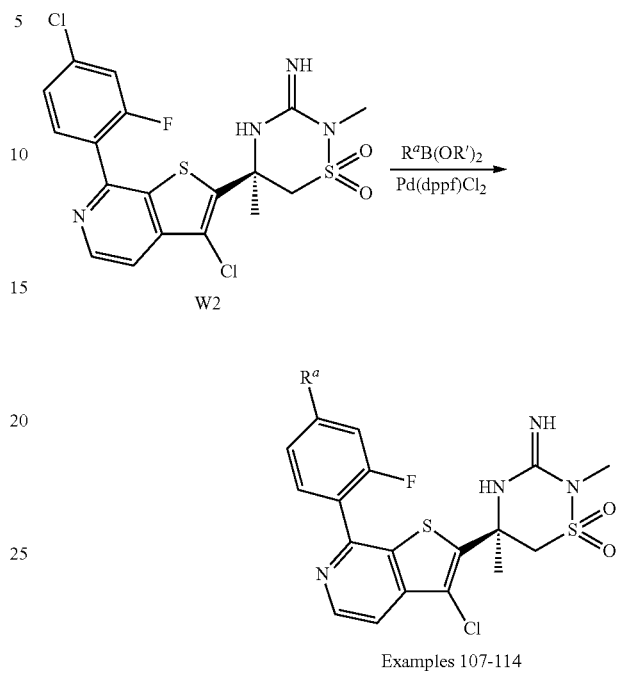

Examples 107-114

Parallel Preparation of Examples 107-114

To a set of 2-dram vials each containing a solution of W2 (30 mg, 0.062 mmol) and a stir bar was added the appropriate boronic acid/pinacol ester (0.074 mmol) (note: tert-butyl 4-(4,4,5,5-tetramethyl-1,3-dioxolan-2-yl)-1H-pyrazole-1-carboxylate was used to prepare Example 114) followed by an aqueous solution of K$_3$PO$_4$ (1M, 0.19 mL, 0.19 mmol). The vials were capped and transferred into a glove box under an atmosphere of nitrogen. To each vial was then added chloro(2-dicyclohexylphosphino-2',4',6'-triisopropyl-1,1'-biphenyl)[2-(2'-amino-1,1'-biphenyl)]palladium(II) (2.4 mg, 0.0031 mmol). The vials were capped, removed from the glove box and placed into a preheated aluminum block at 65° C. The mixtures were stirred at that temperature for 4 hours. To each vial was then added water (1 mL) followed by DCM (2 mL). The layers from each vial were separated and the organic layers were transferred into a new set of vials. The organic solvent was removed in vacuo. To the vial containing the intermediate residue used to prepare Example 114 was added DCM (1 mL) followed by TFA (0.5 mL). This vial was shaken at RT for 2 hours and the solvent was removed in vacuo. Each crude product was dissolved in 1 mL of DMSO and filtered. Example 107 was isolated after the crude residue was purified by mass triggered preparative HPLC [Waters Sunfire C18 column, 5 μm, 19×100 mm, using a gradient from 20% to 55% MeCN (0.1% TFA) in water (0.1% TFA), 25 mL/min, 12 min run]. Examples 108-114 were isolated after the crude residues were purified by mass triggered preparative HPLC [Waters XBridge C18 column, 5 μm, 19×100 mm, using a gradient range from 20-30% initial to 60-80% final MeCN (0.1% NH$_4$OH) in water (0.1% NH$_4$OH), 25 mL/min, 12 min run time].

| Example no. | Example | M + H Obs. | LCMS Method; ($t_R$ min) | BACE1 Ki (nM) |
|---|---|---|---|---|
| 107 | 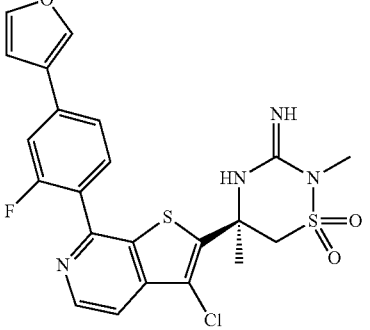 | 505.05 | C (0.94) | 19.72 |
| 108 | 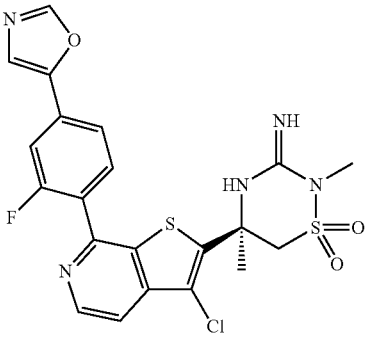 [SMILES: CN1C(=N)N[C@](C)(c2sc3c(-c4ccc(-c5cnco5)cc4F)nccc3c2Cl)CS1(=O)=O] | 506.05 | C (0.84) | 35.16 |
| 109 | 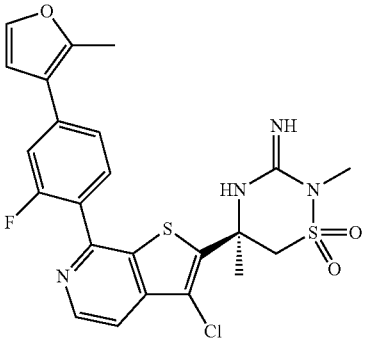 [SMILES: Cc1occc1-c1ccc(-c2nccc3c(Cl)c([C@]4(C)CS(=O)(=O)N(C)C(=N)N4)sc23)c(F)c1] | 519.07 | C (0.85) | 524.9 |
| 110 | 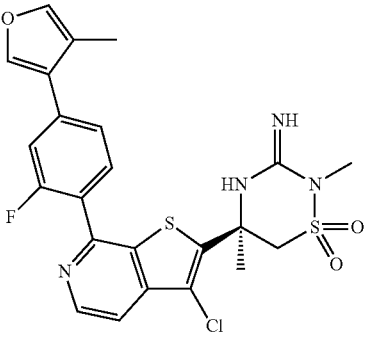 [SMILES: Cc1cocc1-c1ccc(-c2nccc3c(Cl)c([C@]4(C)CS(=O)(=O)N(C)C(=N)N4)sc23)c(F)c1] | 519.07 | C (1.01) | 111.5 |

-continued
| Example no. | Example | LCMS M + H Obs. | Method; ($t_R$ min) | BACE1 Ki (nM) |
|---|---|---|---|---|
| 111 | 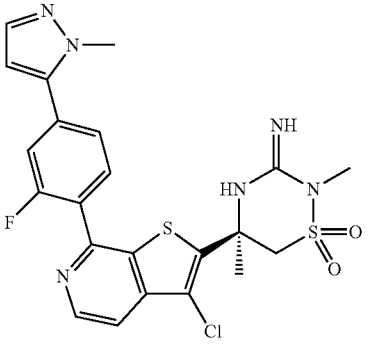 [SMILES: CN1C(=N)N[C@](C)(c2sc3c(-c4ccc(-c5ccnn5C)cc4F)nccc3c2Cl)CS1(=O)=O] | 519.08 | C (0.86) | 196.7 |
| 112 | 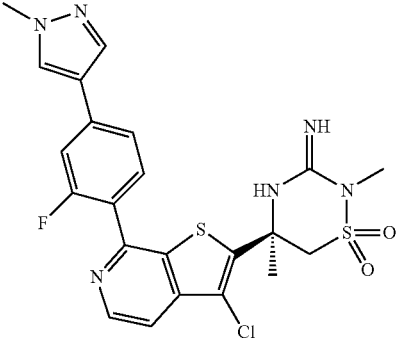 [SMILES: CN1C(=N)N[C@](C)(c2sc3c(-c4ccc(-c5cnn(C)c5)cc4F)nccc3c2Cl)CS1(=O)=O] | 519.08 | C (0.82) | 290.8 |
| 113 | 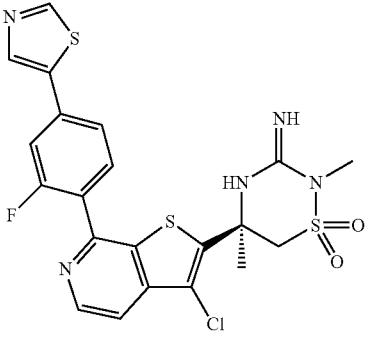 [SMILES: CN1C(=N)N[C@](C)(c2sc3c(-c4ccc(-c5cncs5)cc4F)nccc3c2Cl)CS1(=O)=O] | 522.02 | C (0.87) | 105 |

| Example no. | Example | M + H Obs. | LCMS Method; ($t_R$ min) | BACE1 Ki (nM) |
|---|---|---|---|---|
| 114 | | 505.06 | C (0.79) | 329.9 |

Method Y

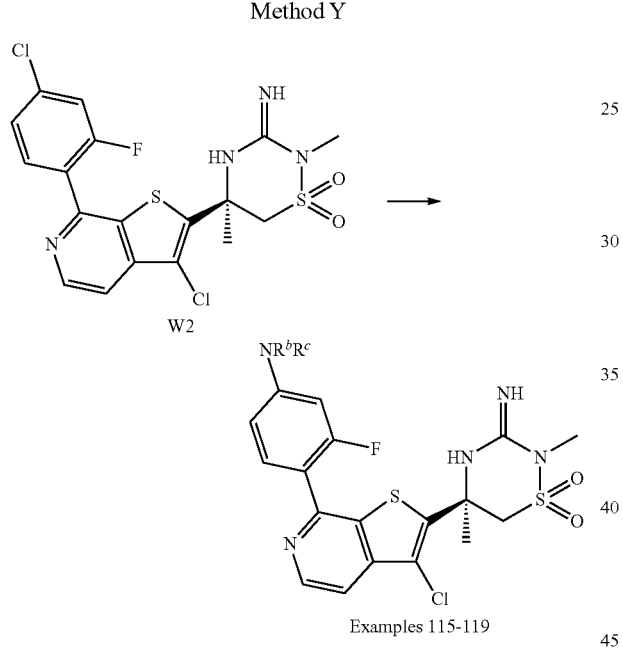

Examples 115-119

Parallel Preparation of Examples 115-119

A capped set of vials containing a mixture of the requisite pyrazole (0.051 mmol) and W2 (20.0 mg, 0.042 mmol) in dioxane (0.75 ml) was transferred into a glove box under an atmosphere of nitrogen. To each vial was added sodium tert-butoxide (12.2 mg, 0.127 mmol) followed by chloro[2-(di-tert-butylphosphino)-2',4',6'-triisopropyl-1,1'-biphenyl][2-(2-aminoethyl)phenyl)]palladium(II) (2.90 mg, 4.23 μmol). The vials were capped and placed into a preheated aluminum block at 100° C. The mixtures were stirred at that temperature for 24 hours. The vials were removed from the heating block, allowed to cool to RT and removed from the glove box. Water (1 mL) was added to each vial followed by DCM (2 mL). The mixtures were transferred to a Varian Bond Elute reservoir and the organic layer from each vial was drained into a new 2-dram vial. To each of the aqueous layers was added additional DCM (1 mL). The organic layer was again drained into the new set of 2-dram vials. The combined organic layers were dried in vacuo. Each crude residue was redissolved in 1 mL of DMSO and filtered. The crude products were purified by mass triggered preparative HPLC [Waters XBridge C18 column, 5 μm, 19×100 mm, using a gradient range from 25-35% initial to 60-70% final MeCN (0.1% NH₄OH) in water (0.1% NH₄OH), 25 mL/min, 12 min run time].

| Example no. | Example | M + H Obs. | LCMS Method; ($t_R$ min) | BACE1 Ki (nM) |
|---|---|---|---|---|
| 115 | | 535.07 | C (0.90) | 17.7 |
| 116 | | 505.06 | C (0.85) | 31.4 |

| Example no. | Example | M + H Obs. | LCMS Method; ($t_R$ min) | BACE1 Ki (nM) |
|---|---|---|---|---|
| 117 | 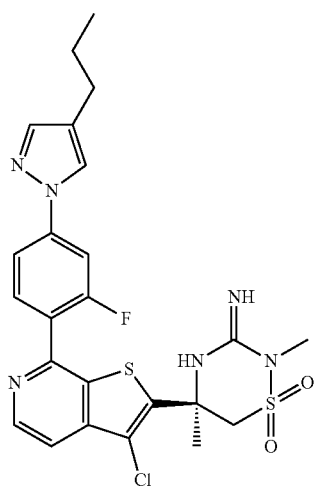 [SMILES: CCCc1cnn(-c2ccc(-c3nccc4c(Cl)c([C@]5(C)CS(=O)(=O)N(C)C(=N)N5)sc34)c(F)c2)c1] | 547.11 | C (1.07) | 259.1 |
| 118 | 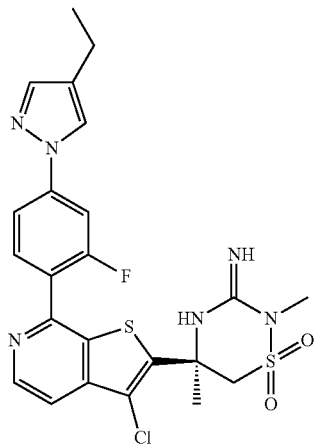 [SMILES: CCc1cnn(-c2ccc(-c3nccc4c(Cl)c([C@]5(C)CS(=O)(=O)N(C)C(=N)N5)sc34)c(F)c2)c1] | 533.09 | C (1.00) | 228.6 |
| 119 | 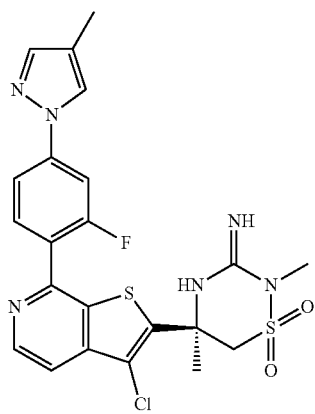 [SMILES: Cc1cnn(-c2ccc(-c3nccc4c(Cl)c([C@]5(C)CS(=O)(=O)N(C)C(=N)N5)sc34)c(F)c2)c1] | 519.08 | C (0.92) | 189.4 |

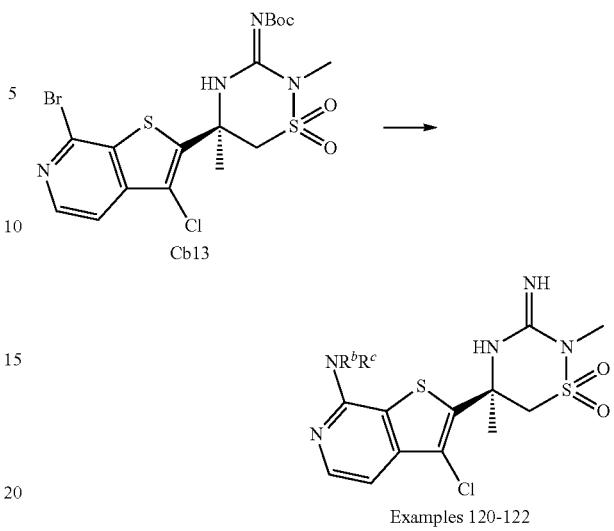

Parallel Preparation of Examples 120-122

To a set of 2-dram vials containing a stir bar in a glove box under an atmosphere of nitrogen was added the requisite amine To each vial was then added a solution of the bromide Cb13 (30 mg, 0.057 mmol) in THF (1 mL), chloro-(2-dicyclohexylphosphino-2',6'-diisopropoxy-1,1'-biphenyl)[2-(2-aminoethyl)phenyl]palladium(II)-methyl-t-butyl ether adduct followed by $Cs_2CO_3$ (56 mg, 0.17 mmol). The vials were capped, removed from the glove box and placed into a preheated aluminum block at 80° C. The mixtures were stirred at that temperature for 18 hours. After that time, the mixtures were allowed to cool to RT. To each vial was added water (2 mL) followed by DCM (2 mL). The layers were separated and the organic layer from each vial was transferred into a new vial. The organic layers were concentrated in vacuo. Each crude product was redissolved in 1 mL of DMSO and filtered. The crude products were purified by mass triggered preparative HPLC [Waters Sunfire C18 column, 5 nm, 19×100 mm, using gradient from 8% to a range of 25-35% MeCN (0.1% Formic acid) in water (0.1% Formic acid); 25 mL/min, 8 min run time] to afford Examples 120-122.

| Example no. | Example | M + H Obs. | LCMS Method; ($t_R$ min) | BACE1 Ki (nM) |
|---|---|---|---|---|
| 102 | 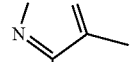 | 511.1 | C (0.81) | 726.4 |

-continued

| Example no. | Example | M+H Obs. | LCMS Method; ($t_R$ min) | BACE1 Ki (nM) |
|---|---|---|---|---|
| 121 | [structure: methoxypyridine-piperazine-chloro-thienopyridine with thiadiazinane sulfone] | 536.12 | C (0.63) | 1855 |
| 122 | [structure: methyl-thiadiazole-piperidine-chloro-thienopyridine with thiadiazinane sulfone] | 526.08 | C (0.71) | 884.6 |

LCMS Conditions
Method A
Column: Agilent Zorbax SB-C18 (3.0×50 mm) 1.8 uM
   Mobile phase: A: 0.05% Trifluoroacetic acid in water
   B: 0.05% Trifluoroacetic acid in acetonitrile
   Gradient: 90:10 (A:B) for 0.3 min, 90:10 to 5:95 (A:B) over 5.1 min, 5:95 (A:B) for 1.2 min.
   Flow rate: 1.0 mL/min
   UV detection: 254 and 220 nm
   Column Temp.=50° C.
   Mass spectrometer: Agilent 6140 quadrupole.
Method B
Column: Agilent Zorbax SB-C18 (3.0×50 mm) 1.8 uM
   Mobile phase: A: $H_2O$/0.05% TFA/0.5% AcOH
   B: Acetonitrile/0.05% TFA/0.5% AcOH
   Gradient: 90:10 to 5:95 (A:B) over 1.5 min, 5:95 (A:B) for 1.2 min.
   Flow rate: 1.0 mL/min
   UV detection: 254 and 220 nm
   Column Temp.=50° C.
   Mass spectrometer: Agilent 6140 quadrupole.
Method C
Acquity UPLC BEH-C18, 1.7 um, 2.1×50 mm
1 mL/min flow
5%-100% MeCN in 1.4 min
0.1% NH3
Assays
   Protocols that used to determine the recited potency values for the compounds of the invention are described below.
BACE1 HTRF FRET Assay Reagents
   $Na^+$-Acetate pH 5.0; 1% Brij-35; Glycerol; Dimethyl Sulfoxide (DMSO); Recombinant human soluble BACE1 catalytic domain (>95% pure); APP Swedish mutant peptide substrate (QSY7-APP$^{swe}$-Eu): QSY7-EISEVNLDAEFC-Europium-amide.
   A homogeneous time-resolved FRET assay can be used to determine $IC_{50}$ values for inhibitors of the soluble human BACE1 catalytic domain. This assay monitors the increase of 620 nm fluorescence that resulted from BACE1 cleavage of an APPswedish APP$^{swe}$ mutant peptide FRET substrate (QSY7-EISEVNLDAEFC-Europium-amide). This substrate contains an N-terminal QSY7 moiety that serves as a quencher of the C-terminal Europium fluorophore (620 nm Em). In the absence of enzyme activity, 620 nm fluorescence is low in the assay and increased linearly over 3 hours in the presence of uninhibited BACE1 enzyme Inhibition of BACE1 cleavage of the QSY7-APP$^{swe}$-Eu substrate by inhibitors is manifested as a suppression of 620 nm fluorescence.
   Varying concentrations of inhibitors at 3× the final desired concentration in a volume of 10 ul are preincubated with purified human BACE1 catalytic domain (3 nM in 10 μl) for 30 minutes at 30° C. in reaction buffer containing 20 mM Na-Acetate pH 5.0, 10% glycerol, 0.1% Brij-35 and 7.5% DSMO. Reactions are initiated by addition of 10 μl of 600 nM QSY7-APP$^{swe}$-Eu substrate (200 nM final) to give a final reaction volume of 30 in a 384 well Nunc HTRF plate. The reactions are incubated at 30° C. for 1.5 hours. The 620 nm fluorescence is then read on a Rubystar HTRF plate reader (BMG Labtechnologies) using a 50 millisecond delay followed by a 400 millisecond acquisition time window. Inhibitor $IC_{50}$ values are derived from non-linear regression analysis of concentration response curves. $K_i$ values are then calculated from $IC_{50}$ values using the Cheng-Prusoff equation using a previously determined μm value of 8 μM for the QSY7-APP$^{swe}$-Eu substrate at BACE1.
BACE-2 Assay
   Inhibitor $IC_{50s}$ at purified human autoBACE-2 are determined in a time-resolved endpoint proteolysis assay that measures hydrolysis of the QSY7-EISEVNLDAEFC-Eu-amide FRET peptide substrate (BACE-HTRF assay). BACE-mediated hydrolysis of this peptide results in an increase in relative fluorescence (RFU) at 620 nm after excitation with 320 nm light Inhibitor compounds, prepared at 3× the desired final concentration in 1×BACE assay buffer (20 mM sodium acetate pH 5.0, 10% glycerol, 0.1% Brij-35) supplemented with 7.5% DMSO are pre-incubated with an equal volume of autoBACE-2 enzyme diluted in 1×BACE assay buffer (final enzyme concentration 1 nM) in black 384-well NUNC plates for 30 minutes at 30° C. The assay is initiated by addition of an equal volume of the QSY7-EISEVNLDAEFC-Eu-amide substrate (200 nM final concentration, $K_m$=8 μM for 4 μM for autoBACE-2) prepared in 1×BACE assay buffer supplemented with 7.5% DMSO and incubated for 90 minutes at 30° C. DMSO is present at 5% final concentration in the assay. Following laser excitation of sample wells at 320 nm, the fluorescence signal at 620 nm is collected for 400 ms following a 50 μs delay on a RUBYstar HTRF plate reader (BMG Labtechnologies). Raw RFU data is normalized to maximum (1.0 nM BACE/DMSO) and minimum (no enzyme/DMSO) RFU values. $IC_{50s}$ are determined by nonlinear regression analysis (sigmoidal dose response, variable slope) of percent inhibition data with minimum and maximum values set to 0 and 100 percent respectively. Similar $IC_{50s}$ are obtained when using raw RFU data. The $K_i$ values are calculated from the $IC_{50}$ using the Cheng-Prusoff equation. BACE2 Ki values for the non-limiting example compounds of the invention are shown in Table 11 below.

TABLE 11

| Ex. # | BACE2 Ki (nM) |
|---|---|
| 1 | 6.0 |
| 2 | 13.8 |
| 3 | 25.9 |
| 4 | 0.35 |
| 5 | 8.9 |
| 6 | 1.4 |
| 7 | 0.73 |
| 8 | 219 |
| 9 | 0.31 |
| 10 | 1.0 |
| 11 | 2.0 |
| 12 | 3.7 |
| 13 | 2.4 |
| 14 | 3.5 |
| 15 | 3.8 |
| 16 | 4.2 |
| 17 | 2.2 |
| 18 | 4.2 |
| 19 | 52 |
| 20 | 8.9 |
| 21 | 16 |
| 22 | 98 |
| 23 | 4.8 |
| 24 | 18 |
| 25 | 4.8 |
| 26 | 5.7 |
| 27 | 152 |
| 28 | 0.28 |
| 29 | 1.3 |
| 30 | 235 |
| 31 | 4.2 |
| 32 | 3.9 |
| 33 | 10 |
| 34 | 11 |
| 35 | 30 |
| 36 | 247 |
| 37 | 4.6 |
| 38 | 3.6 |
| 39 | 9.9 |
| 40 | 9.5 |
| 41 | 0.35 |
| 42 | 1.1 |
| 43 | 6.5 |
| 44 | 0.24 |
| 45 | 3.0 |
| 46 | 0.41 |
| 47 | 0.34 |
| 48 | 0.63 |
| 49 | 1.1 |
| 50 | 2.3 |
| 51 | 2.5 |
| 52 | 17 |
| 54 | 12 |
| 55 | 212 |
| 56 | 20 |
| 57 | 44 |
| 58 | 66 |
| 59 | 92 |
| 60 | 1.6 |
| 61 | 42 |
| 62 | 1.6 |
| 63 | 4.7 |
| 64 | 1043 |
| 65 | 1613 |
| 66 | 1800 |
| 67 | 555 |
| 68 | 77 |
| 69 | 337 |
| 70 | 174 |
| 71 | 654 |
| 72 | 26 |
| 73 | 123 |
| 74 | 122 |
| 75 | 2530 |
| 76 | 52 |
| 77 | 69 |
| 78 | 23 |
| 79 | 22 |
| 80 | 16 |
| 81 | 1715 |
| 82 | 61 |
| 83 | 148 |
| 84 | 764 |
| 85 | 4692 |
| 86 | 3296 |
| 87 | 31 |
| 88 | 3841 |
| 89 | 68 |
| 90 | 214 |
| 91 | 1353 |
| 92 | 1657 |
| 93 | 2659 |
| 94 | 9524 |
| 95 | 2030 |
| 96 | 9524 |
| 97 | 64 |
| 98 | 6.7 |
| 99 | 855 |
| 100 | 224 |
| 101 | 116 |
| 102 | 959 |
| 103 | 30 |
| 104 | 36 |
| 105 | 86 |
| 106 | 1639 |
| 107 | 270 |
| 108 | 19 |
| 109 | 87 |
| 110 | 444 |
| 111 | 27 |
| 112 | 218 |
| 113 | 252 |
| 114 | 134 |
| 115 | 267 |
| 116 | 110 |
| 117 | 35 |
| 118 | 702 |
| 119 | 417 |
| 120 | 96 |
| 121 | 1262 |
| 122 | 408 |

The compounds of the invention, surprisingly and advantageously, inhibit BACE, as shown by the BACE inhibitory data reported herein. Some of the compounds of the invention, surprisingly and advantageously, demonstrate low susceptibility to efflux by human P-glycoprotein, as evidenced by a low efflux ratio (Pgp Mdrl ER) shown in Table 12 below. Some of the compounds of the invention, surprisingly and advantageously, demonstrate good selectivity for BACE over Cathepsin-D (Cath-D), as shown in Table 13. Example 80 exhibits an unexpected combination of good BACE potency, low Pgp susceptibility, and good Cathepsin-D selectivity.

TABLE 12

| Ex | Structure | Pgp Mdr1 ER |
|---|---|---|
| 6 | 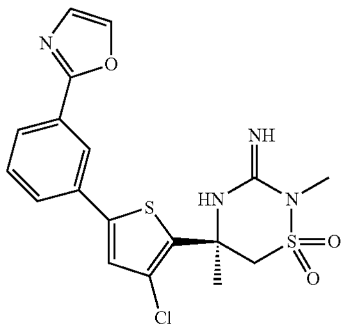 [SMILES: CN1C(=N)N[C@](C)(c2sc(-c3cccc(-c4ncco4)c3)cc2Cl)CS1(=O)=O] | 0.49 |
| 7 | 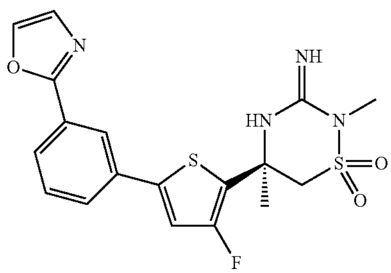 [SMILES: CN1C(=N)N[C@](C)(c2sc(-c3cccc(-c4ncco4)c3)cc2F)CS1(=O)=O] | 1.7 |
| 11 | 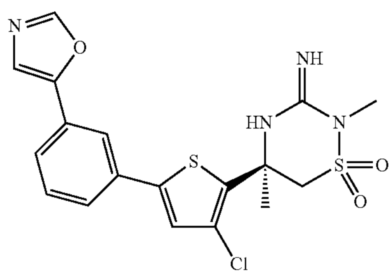 [SMILES: CN1C(=N)N[C@](C)(c2sc(-c3cccc(-c4cnco4)c3)cc2Cl)CS1(=O)=O] | 1.3 |
| 12 | 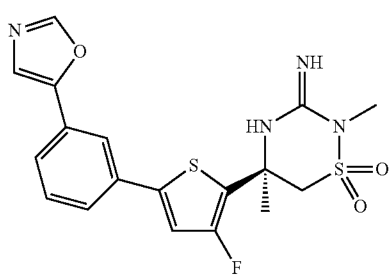 [SMILES: CN1C(=N)N[C@](C)(c2sc(-c3cccc(-c4cnco4)c3)cc2F)CS1(=O)=O] | 1.8 |
| 14 | 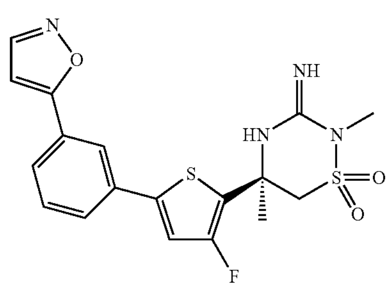 [SMILES: CN1C(=N)N[C@](C)(c2sc(-c3cccc(-c4ccno4)c3)cc2F)CS1(=O)=O] | 1.6 |

TABLE 12-continued

| Ex | Structure | Pgp Mdr1 ER |
|---|---|---|
| 17 | 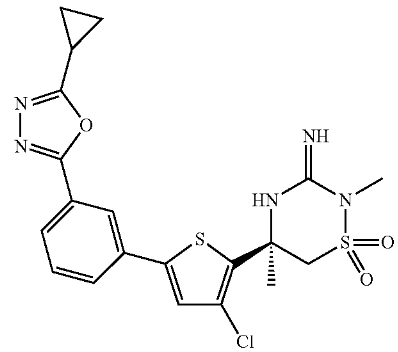 [SMILES: CN1C(=N)N[C@](C)(c2sc(-c3cccc(-c4nnc(C5CC5)o4)c3)cc2Cl)CS1(=O)=O] | 1.0 |
| 18 | 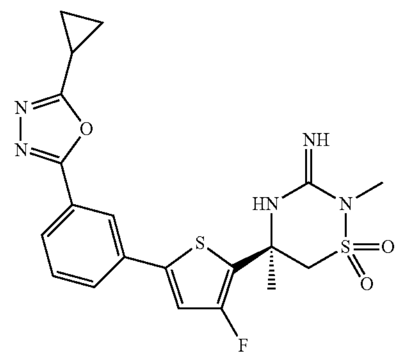 [SMILES: CN1C(=N)N[C@](C)(c2sc(-c3cccc(-c4nnc(C5CC5)o4)c3)cc2F)CS1(=O)=O] | 0.53 |
| 23 | 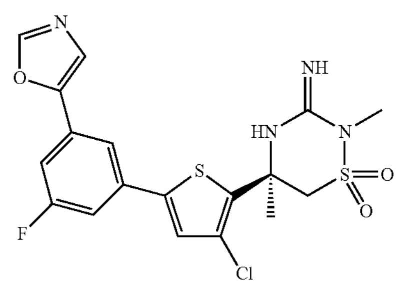 [SMILES: CN1C(=N)N[C@](C)(c2sc(-c3cc(F)cc(-c4cnco4)c3)cc2Cl)CS1(=O)=O] | 0.90 |
| 25 | 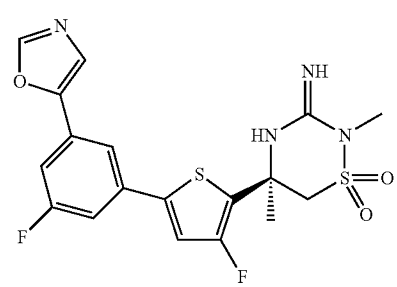 [SMILES: CN1C(=N)N[C@](C)(c2sc(-c3cc(F)cc(-c4cnco4)c3)cc2F)CS1(=O)=O] | 1.1 |
| 38 | 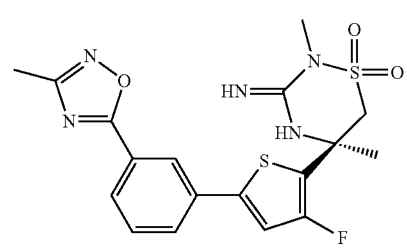 [SMILES: Cc1noc(-c2cccc(-c3cc(F)c([C@]4(C)CS(=O)(=O)N(C)C(=N)N4)s3)c2)n1] | 1.7 |

TABLE 12-continued

| Ex | Structure | Pgp Mdr1 ER |
|----|-----------|-------------|
| 41 | 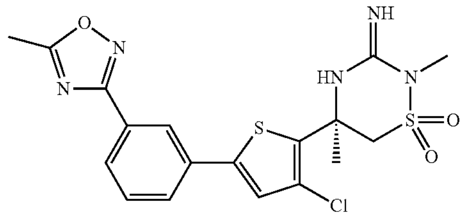 [SMILES: Cc1nc(-c2cccc(-c3cc(Cl)c([C@]4(C)CS(=O)(=O)N(C)C(=N)N4)s3)c2)no1] | 0.34 |
| 42 | 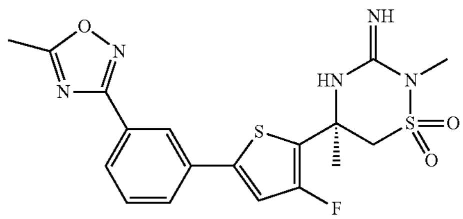 | 1.2 |
| 46 | 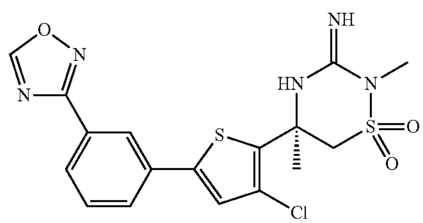 [SMILES: CN1C(=N)N[C@](C)(c2sc(-c3cccc(-c4ncon4)c3)cc2Cl)CS1(=O)=O] | 0.70 |
| 47 | 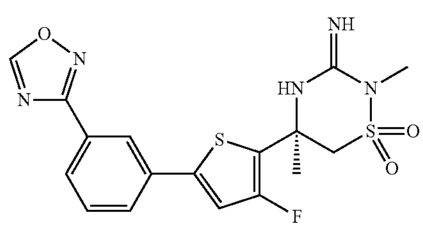 [SMILES: CN1C(=N)N[C@](C)(c2sc(-c3cccc(-c4ncon4)c3)cc2F)CS1(=O)=O] | 1.7 |
| 80 | 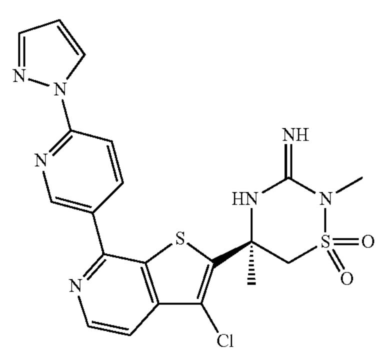 [SMILES: CN1C(=N)N[C@](C)(c2sc3c(-c4ccc(-n5cccn5)nc4)nccc3c2Cl)CS1(=O)=O] | 0.78 |

TABLE 13

| Ex | Structure | Cath-D Ki |
|----|-----------|-----------|
| 80 | 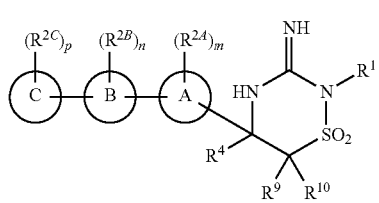 | 6969 nM |

We claim:

1. A compound, or a stereoisomer of said compound, or a pharmaceutically acceptable salt of said compound or said stereoisomer, said compound having the structural Formula (I):

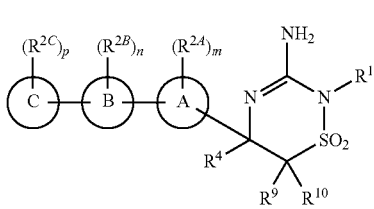

(I)

or a tautomer thereof having the structural Formula (I'):

(I')

or pharmaceutically acceptable salt thereof, wherein:

$R^1$ is selected from the group consisting of H, lower alkyl, lower heteroalkyl, lower cycloalkyl, and -(lower alkyl)-(lower cycloalkyl) wherein each said lower alkyl, lower heteroalkyl, lower cycloalkyl, and -(lower alkyl)-(lower cycloalkyl) is optionally substituted with fluoro;

ring A is selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

each $R^{2A}$ (when present) is independently selected from the group consisting of: halo, oxo, —OH, —CN, —SF$_5$, —OSF$_5$, —NO$_2$, —Si(R$^5$)$_3$, —N(R$^6$)$_2$, —OR$^6$, —SR$^6$, alkyl, haloalkyl, heteroalkyl, alkenyl, alkynyl, cycloalkyl, -alkyl-cycloalkyl, heterocycloalkyl, and -alkyl-heterocycloalkyl, wherein said alkyl, haloalkyl, heteroalkyl, alkenyl, alkynyl, cycloalkyl, -alkyl-cycloalkyl, heterocycloalkyl, and -alkyl-heterocycloalkyl of $R^{2A}$ are each optionally unsubstituted or substituted with one or more groups independently selected from $R^8$;

m is 0 or more;

ring B is selected from the group consisting of a 6-membered aryl, 6-membered cycloalkyl, 6-membered cycloalkenyl, 6-membered heteroaryl, a 6-membered heterocycloalkyl, and a 6-membered heterocycloalkenyl ring, wherein each said heteroatom containing ring comprises from 1 to 4 ring heteroatoms independently selected from the group consisting of N, N-oxide, O, S, S(O), and S(O)$_2$;

each $R^{2B}$ (when present) is independently selected from the group consisting of halo, —CN, alkyl, cycloalkyl, -alkyl-cycloalkyl, heterocycloalkyl, heteroalkyl, haloalkyl —O-alkyl, —O-cycloalkyl, —O-alkyl-cycloalkyl, —O-heteroalkyl, and —O-haloalkyl;

n is 0 or more;

ring C is selected from the group consisting of aryl, monocyclic heteroaryl, monocyclic cycloalkyl, monocyclic cycloalkenyl, monocyclic heterocycloalkyl, monocyclic heterocycloalkenyl, and a multicyclic group;

each $R^2$ (when present) is independently selected from the group consisting of: halo, oxo, —OH, —CN, —SF$_5$, —OSF$_5$, —Si($R^5$)$_3$, —N($R^6$)$_2$, —NR$^7$C(O)R$^6$, —NR$^7$S(O)$_2$R$^{12}$, —NR$^7$S(O)$_2$N($R^6$)$_2$, —NR$^7$C(O)N($R^6$)$_2$, —NR$^7$C(O)OR$^6$, —C(O)R$^6$, —C(O)$_2$R$^6$, —C(O)N($R^6$)$_2$, —S(O)R$^{12}$, —S(O)$_2$R$^{12}$, —S(O)$_2$N($R^6$)$_2$, —OR$^6$, —SR$^6$, alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl, wherein said alkyl, haloalkyl, heteroalkyl, alkenyl, alkynyl, cycloalkyl, -alkyl-cycloalkyl, aryl, -alkyl-aryl, heteroaryl, -alkyl-heteroaryl, heterocycloalkyl, and -alkyl-heterocycloalkyl of $R^{2C}$ are each optionally unsubstituted or substituted with one or more groups independently selected from $R^8$;

p is 0 or more;

$R^4$ is selected from the group consisting of lower alkyl and lower haloalkyl;

each $R^5$ (when present) is independently selected from the group consisting of alkyl, heteroalkyl, haloalkyl, cycloalkyl, and -alkyl-cycloalkyl;

each $R^6$ (when present) is independently selected from the group consisting of H, alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl, wherein each said alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl of $R^6$ is unsubstituted or substituted with one or more groups independently selected from halo, —CN, —OH, lower alkyl, lower cycloalkyl, lower heteroalkyl, lower haloalkyl, lower —O-alkyl, lower —O-heteroalkyl, and lower —O-haloalkyl;

each $R^7$ (when present) is independently selected from the group consisting of H, alkyl, heteroalkyl, haloalkyl, cycloalkyl, -alkyl-cycloalkyl, aryl, -alkyl-aryl, heteroaryl, and -alkyl-heteroaryl, wherein each said cycloalkyl, -alkyl-cycloalkyl, aryl, -alkyl-aryl, heteroaryl, and -alkyl-heteroaryl of $R^7$ is unsubstituted or substituted with one or more groups independently selected from halo, —CN, lower alkyl, lower cycloalkyl, lower heteroalkyl, lower haloalkyl, lower —O-alkyl, lower —O-heteroalkyl, and lower —O-haloalkyl;

each $R^8$ (when present) is independently selected from the group consisting of halo, oxo, —OH, —CN, —SF$_5$, —OSF$_5$, alkyl, —O-alkyl, haloalkyl, haloalkoxy, —C(O)OR$^{11}$, cycloalkyl, -alkyl-cycloalkyl, —O-cycloalkyl, —O-alkyl-cycloalkyl, —O-benzyl, heteroalkyl, —O-heteroalkyl, and -alkyl-OH;

$R^9$ is selected from the group consisting of H, halo, alkyl, cycloalkyl, haloalkyl, and heteroalkyl;

$R^{10}$ is selected from the group consisting of H, halo, alkyl, cycloalkyl, haloalkyl, and heteroalkyl;

$R^{11}$ (when present) is selected from the group consisting of H, lower alkyl, lower heteroalkyl, lower cycloalkyl, and -alkyl-(lower cycloalkyl); and each $R^{12}$ (when present) is independently selected from the group consisting of alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl, wherein each said alkyl, alkenyl, alkynyl, heteroalkyl, haloalkyl, cycloalkyl, -alkyl-cycloalkyl, heterocycloalkyl, -alkyl-heterocycloalkyl, aryl, -alkyl-aryl, heteroaryl, and -alkyl-heteroaryl of $R^{12}$ is unsubstituted or substituted with one or more groups independently selected from halo, —CN, —OH, lower alkyl, lower cycloalkyl, lower heteroalkyl, lower haloalkyl, lower —O-alkyl, lower —O-heteroalkyl, and lower —O-haloalkyl.

2. A compound of claim 1, or a tautomer thereof, or a stereoisomer of said compound or said tautomer, or a pharmaceutically acceptable salt of said compound, said tautomer, or said stereoisomer, wherein:

$R^4$ is selected from the group consisting of —CH$_3$ and —CHF$_2$; and one of $R^9$ and $R^{10}$ is H and the other is selected from the group consisting of H, halo, lower alkyl, cycloalkyl, lower haloalkyl, and lower heteroalkyl.

3. A compound of claim 2, or a tautomer thereof, or a stereoisomer of said compound or said tautomer, or a pharmaceutically acceptable salt of said compound, said tautomer, or said stereoisomer, wherein:

ring B is selected from the group consisting of phenyl, pyridyl, tetrahydropyridyl, pyrimidinyl, pyrazinyl, triazinyl, tetrazinyl, piperdinyl, and piperazinyl.

4. A compound of claim 3, or a tautomer thereof, or a stereoisomer of said compound or said tautomer, or a pharmaceutically acceptable salt of said compound, said tautomer, or said stereoisomer, wherein:

n is 0 or more; and each $R^{2B}$ (when present) is independently selected from the group consisting of halo, —CN, methyl, ethyl, propyl, cyclopropyl, —CH$_2$-cyclopropyl, —OCH$_3$, —CH$_2$OCH$_3$, —CHF$_2$, —CH$_2$F, —CF$_3$, —OCF$_3$, and —OCHF$_2$.

5. A compound of claim 4, or a tautomer thereof, or a stereoisomer of said compound or said tautomer, or a pharmaceutically acceptable salt of said compound, said tautomer, or said stereoisomer, wherein:

ring A is selected from the group consisting of phenyl, pyridyl, pyrazinyl, furanyl, thienyl, pyrimidinyl, pyridazinyl, thiazolyl, thiadiazolyl, isothiazolyl, oxazolyl, oxadiazolyl, isoxazolyl, imidazolyl, pyrazolyl, pyrrolyl, quinazolinyl, benzofuranyl, benzimidazolyl, benzoxazolyl, benzoisoxazolyl, benzothiazolyl, benzoisothiazolyl, benzothienyl, naphthyl, quinolyl, isoquinolyl, indazolyl, indolyl, thienopyridyl, and thienylpyrazolyl.

6. A compound of claim 5, or a tautomer thereof, or a stereoisomer of said compound or said tautomer, or a pharmaceutically acceptable salt of said compound, said tautomer, or said stereoisomer, wherein:

m is 0 or more; and each $R^{2A}$ group (when present) is independently selected from the group consisting of halo, oxo, —CN, —SF$_5$, —NHCH$_3$, —N(CH$_3$)$_2$, —OCH$_3$, —OCH$_2$CH$_3$, —O-cyclopropyl, —O—CH$_2$-cyclopropyl, —CH$_2$OCH$_3$, —S(CH$_3$), methyl, ethyl, propyl, cyclopropyl, —CH$_2$-cyclopropyl, —C≡C—CH$_3$, —CF$_3$, —CHF$_2$, —OCF$_3$, and —OCHF$_2$.

7. A compound according to claim 6, or a tautomer thereof, or a stereoisomer of said compound or said tautomer, or a pharmaceutically acceptable salt of said compound, said tautomer, or said stereoisomer, wherein:

ring C is selected from the group consisting of azetidinyl, benzimidazolyl, benzothiazolyl, cyclopropyl, cyclobutyl, dihydroindenyl, dihydrooxazolyl, furanyl, imadazolyl, indenyl, indolyl, isothiazolyl, isoxazolyl, morpholinyl, oxadiazolyl, oxazolyl, phenyl, piperazinyl, pyrazinyl, pyrazolyl, pyridazinyl, pyridyl, pyrimidinyl, pyrazolopyridinyl, pyrrolyl, pyrrolopyridinyl, pyrrolopyrimidinyl, tetrazolyl, thiadiazolyl, thiazolyl, thienyl, thiomorpholinyl, thiomorpholinyl dioxide, and triazolyl.

8. A compound according to claim 7, or a tautomer thereof, or a stereoisomer of said compound or said tautomer, or a pharmaceutically acceptable salt of said compound, said tautomer, or said stereoisomer, wherein:

p is 0 or more; and each $R^{2C}$ group (when present) is independently selected from the group consisting of halo, oxo, —CN, —SF$_5$, —OSF$_5$, —N(R$^6$)$_2$, —NR$^7$C(O)R$^6$, —NR$^7$S(O)$_2$R$^{12}$, —NR$^7$C(O)N(R$^6$)$_2$, —NR$^7$C(O)OR$^6$, —C(O)R$^6$, —C(O)$_2$R$^6$, —C(O)N(R$^6$)$_2$, —S(O)R$^{12}$, —S(O)$_2$R$^{12}$, —S(O)$_2$N(R$^6$)$_2$, —OR$^6$, —SR$^6$, lower alkyl, lower haloalkyl, lower heteroalkyl, lower alkynyl, aryl, -alkyl-aryl-, cycloalkyl, heteroaryl, -alkyl-heteroaryl, heterocycloalkyl, and heterocycloalkenyl, wherein each said lower alkyl, lower haloalkyl, lower heteroalkyl, lower alkynyl, aryl, -alkyl-aryl-, cycloalkyl, heteroaryl, -alkyl-heteroaryl, heterocycloalkyl, and heterocycloalkenyl of $R^2$ (when present) is independently unsubstituted or substituted with one or more groups independently selected from the group consisting of $R^8$.

9. A compound of claim 1, or a tautomer thereof, or a stereoisomer of said compound or said tautomer, or a pharmaceutically acceptable salt of said compound, said tautomer, or said stereoisomer, said compound selected from the group consisting of:

| Example |
|---|
| 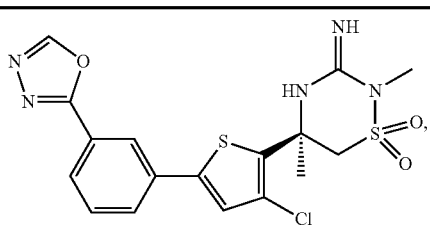 |

-continued

| Example |
|---|
| 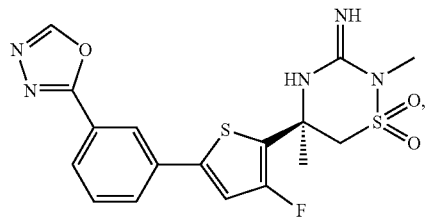 [SMILES: CN1C(=N)N[C@](C)(c2sc(-c3cccc(-c4nnco4)c3)cc2F)CS1(=O)=O] |
| 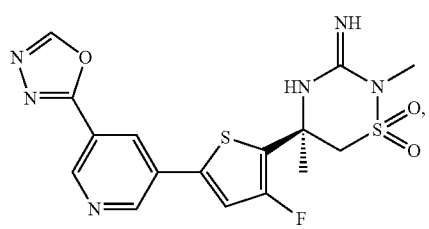 [SMILES: CN1C(=N)N[C@](C)(c2sc(-c3cncc(-c4nnco4)c3)cc2F)CS1(=O)=O] |
| 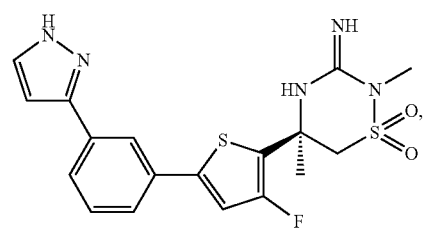 [SMILES: CN1C(=N)N[C@](C)(c2sc(-c3cccc(-c4cc[nH]n4)c3)cc2F)CS1(=O)=O] |
| 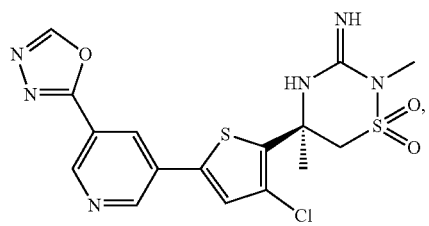 [SMILES: CN1C(=N)N[C@](C)(c2sc(-c3cncc(-c4nnco4)c3)cc2Cl)CS1(=O)=O] |
| 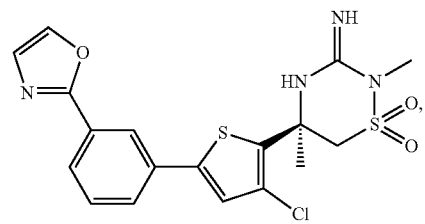 [SMILES: CN1C(=N)N[C@](C)(c2sc(-c3cncc(-c4ncco4)c3)cc2Cl)CS1(=O)=O] |
| 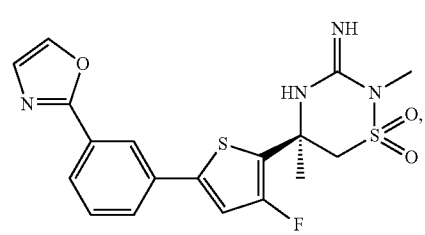 |

| 167 -continued | 168 -continued |
|---|---|
| Example | Example |

| 169 -continued | 170 -continued |
|---|---|
| Example | Example |
| 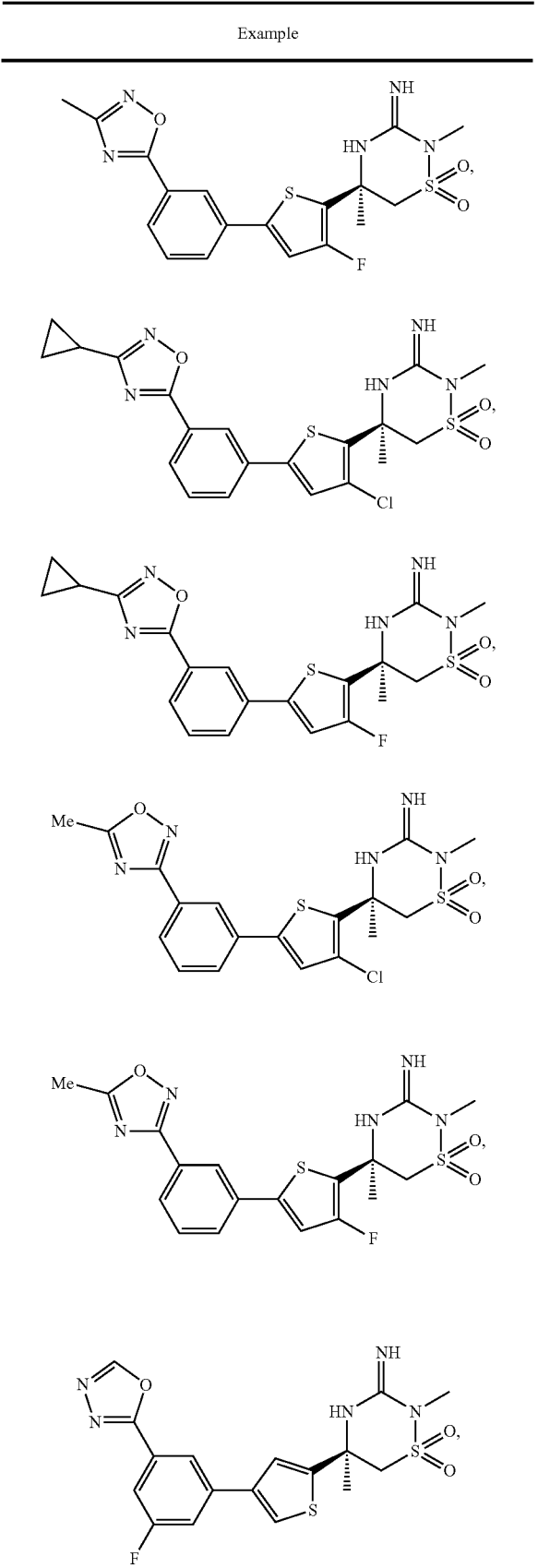 | 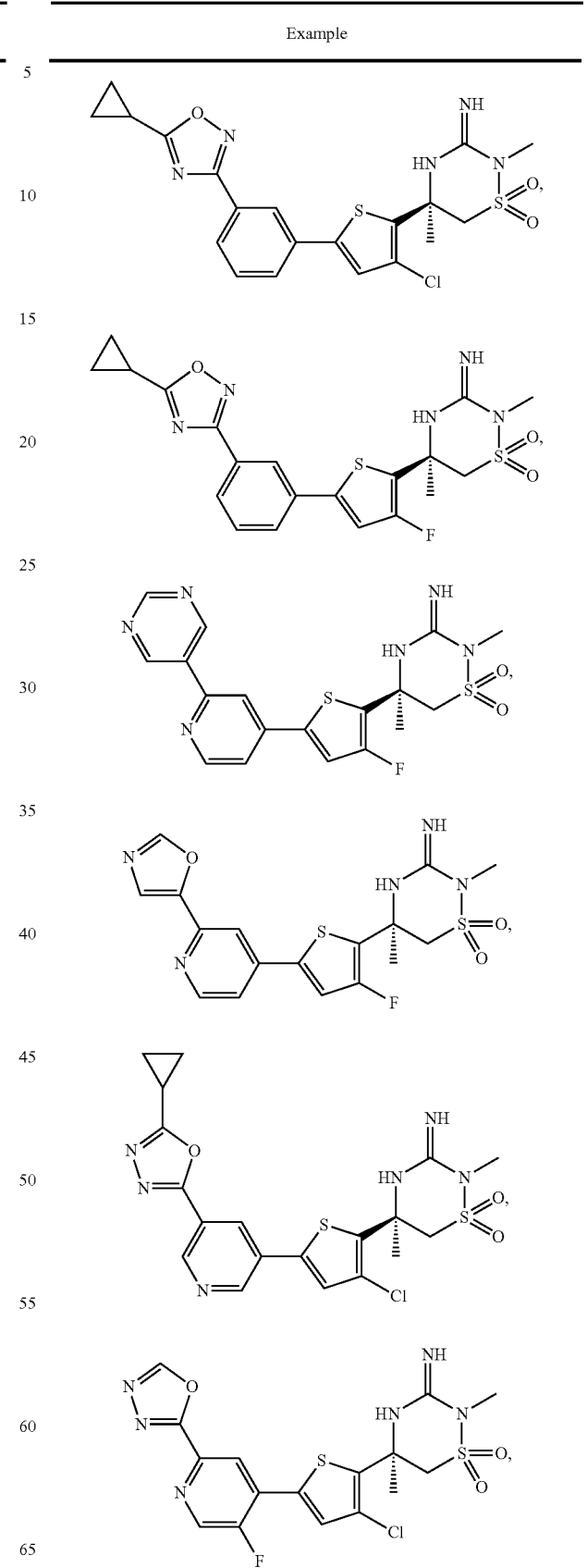 |

| 171 -continued | 172 -continued |
|---|---|
| Example | Example |
| 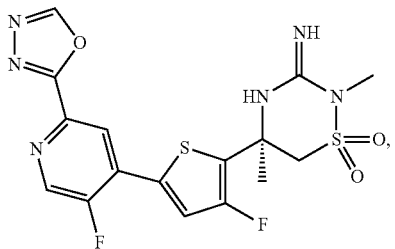 [SMILES: CN1C(=N)N[C@](C)(c2sc(-c3cc(-c4nnco4)ncc3F)cc2F)CS1(=O)=O] | 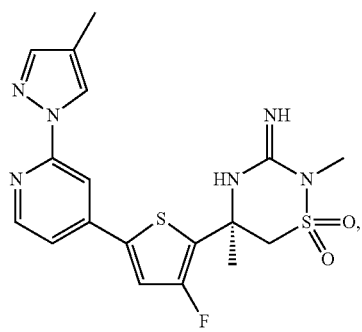 |
| 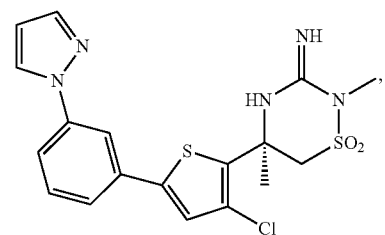 [SMILES: CN1C(=N)N[C@](C)(c2sc(-c3cccc(-n4cccn4)c3)cc2Cl)CS1(=O)=O] | 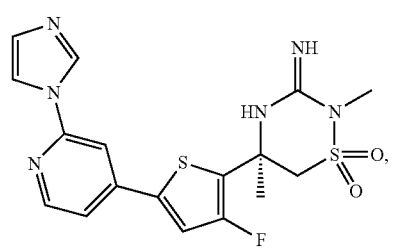 |
| 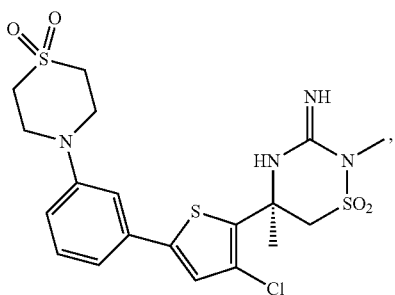 [SMILES: CN1C(=N)N[C@](C)(c2sc(-c3cccc(N4CCS(=O)(=O)CC4)c3)cc2Cl)CS1(=O)=O] | 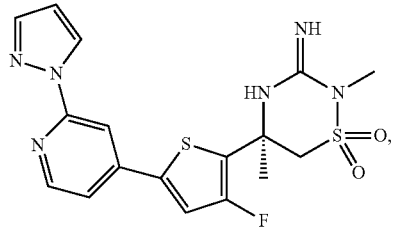 |
| 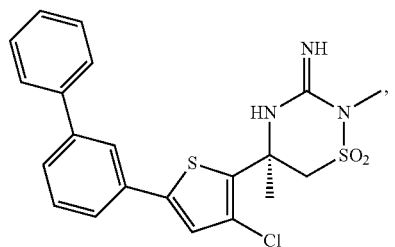 [SMILES: CN1C(=N)N[C@](C)(c2sc(-c3cccc(-c4ccccc4)c3)cc2Cl)CS1(=O)=O] | 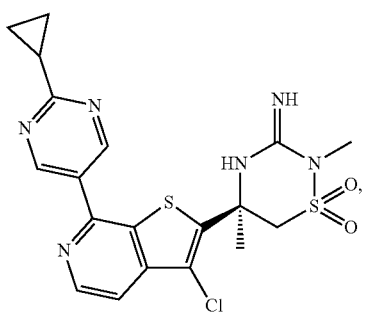 |
| 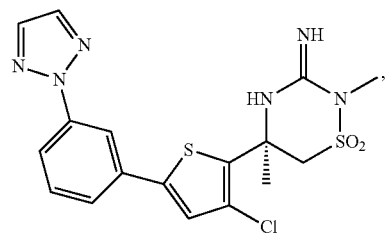 [SMILES: CN1C(=N)N[C@](C)(c2sc(-c3cccc(-n4nccn4)c3)cc2Cl)CS1(=O)=O] | 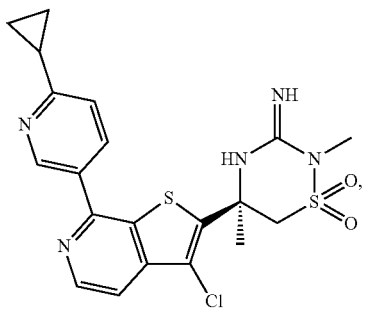 |
| 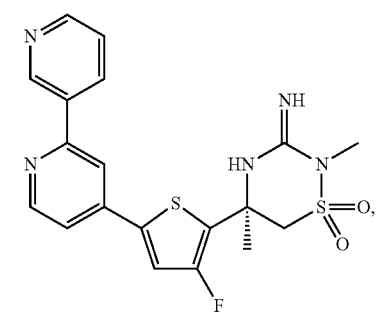 [SMILES: CN1C(=N)N[C@](C)(c2sc(-c3ccnc(-c4cccnc4)c3)cc2F)CS1(=O)=O] | |

| Example | Example |
|---|---|
| 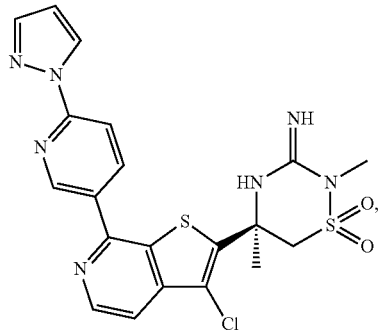 [SMILES: CN1C(=N)N[C@](C)(c2sc3c(-c4ccc(-n5cccn5)nc4)nccc3c2Cl)CS1(=O)=O]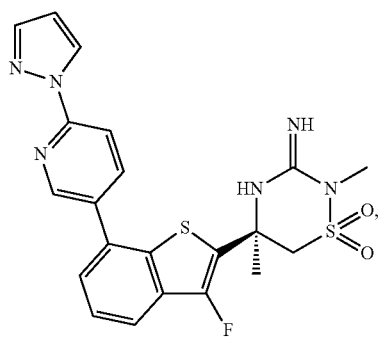 [SMILES: CN1C(=N)N[C@](C)(c2sc3c(-c4ccc(-n5cccn5)nc4)cccc3c2F)CS1(=O)=O]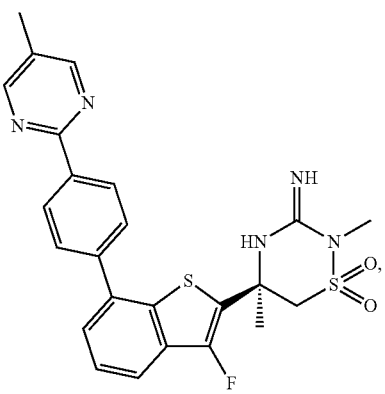 [SMILES: Cc1cnc(-c2ccc(-c3cccc4c(F)c([C@]5(C)CS(=O)(=O)N(C)C(=N)N5)sc34)cc2)nc1]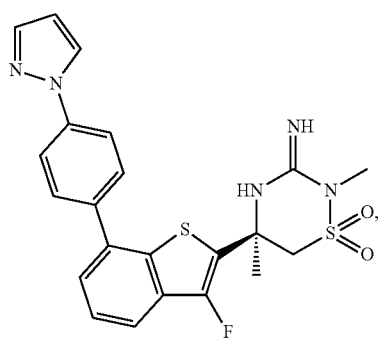 [SMILES: CN1C(=N)N[C@](C)(c2sc3c(-c4ccc(-n5cccn5)cc4)cccc3c2F)CS1(=O)=O] | 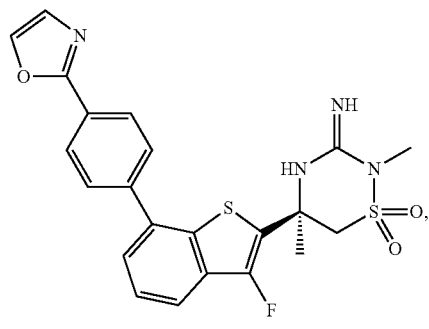 [SMILES: CN1C(=N)N[C@](C)(c2sc3c(-c4ccc(-c5ncco5)cc4)cccc3c2F)CS1(=O)=O]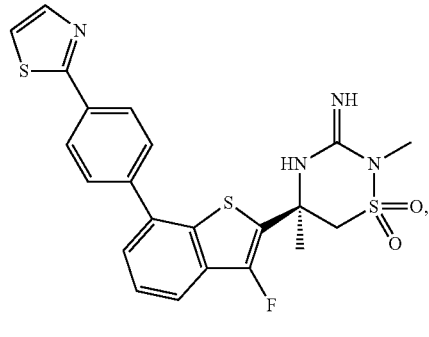 [SMILES: CN1C(=N)N[C@](C)(c2sc3c(-c4ccc(-c5nccs5)cc4)cccc3c2F)CS1(=O)=O]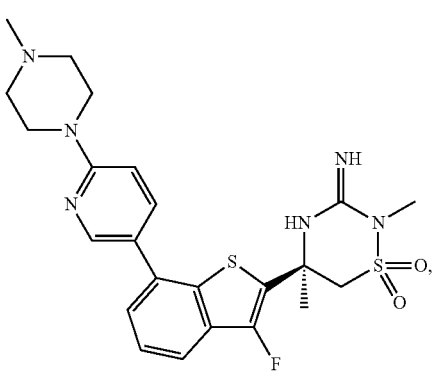 [SMILES: CN1CCN(c2ccc(-c3cccc4c(F)c([C@]5(C)CS(=O)(=O)N(C)C(=N)N5)sc34)cn2)CC1]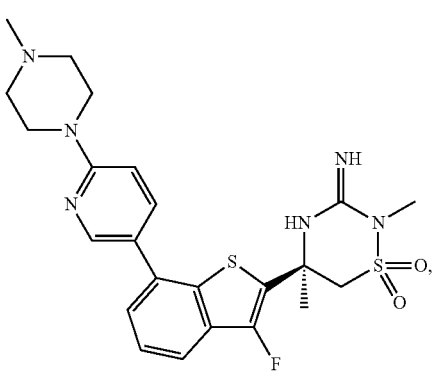 [SMILES: CN1CCN(c2ccc(-c3cccc4c(F)c([C@]5(C)CS(=O)(=O)N(C)C(=N)N5)sc34)cn2)CC1]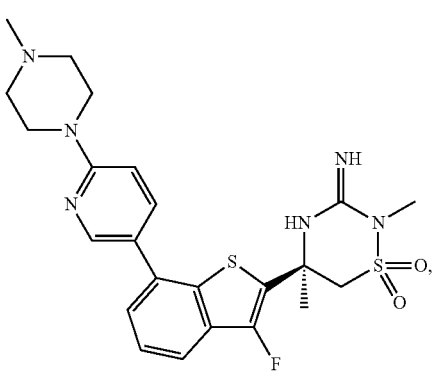 [SMILES: CN1CCN(c2ccc(-c3cccc4c(F)c([C@]5(C)CS(=O)(=O)N(C)C(=N)N5)sc34)cn2)CC1] |

| 175 -continued | 176 -continued |
|---|---|
| Example | Example |
| 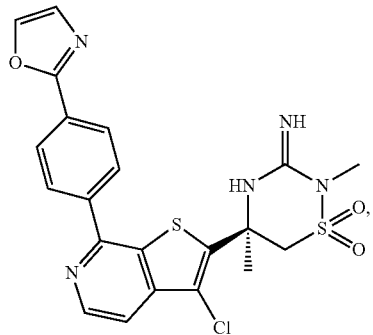 [SMILES: CN1C(=N)N[C@](C)(c2sc3c(-c4ccc(-c5ncco5)cc4)nccc3c2Cl)CS1(=O)=O] | 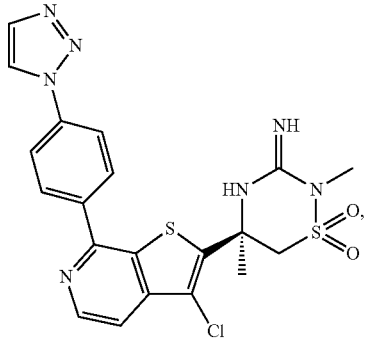 |
| 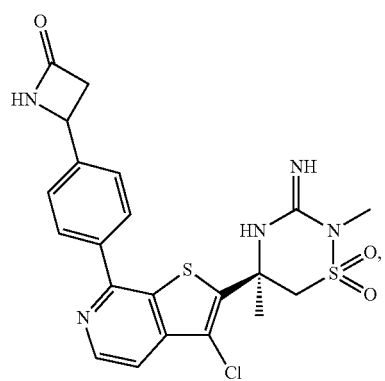 [SMILES: CN1C(=N)N[C@](C)(c2sc3c(-c4ccc(C5CC(=O)N5)cc4)nccc3c2Cl)CS1(=O)=O] | 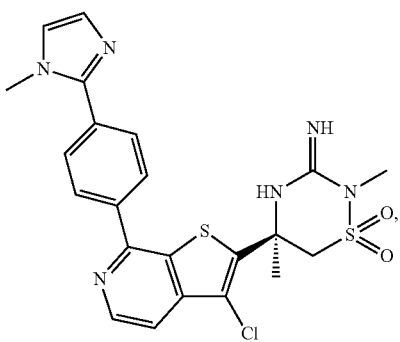 |
| 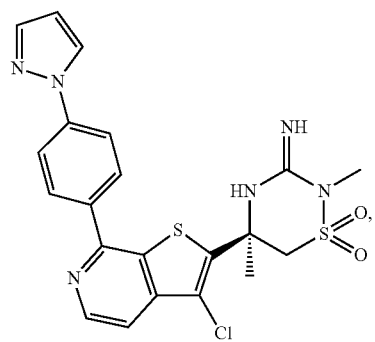 [SMILES: CN1C(=N)N[C@](C)(c2sc3c(-c4ccc(-n5cccn5)cc4)nccc3c2Cl)CS1(=O)=O] | 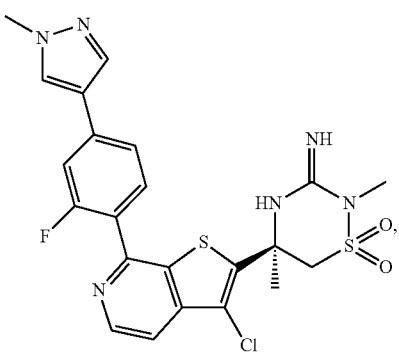 |
| 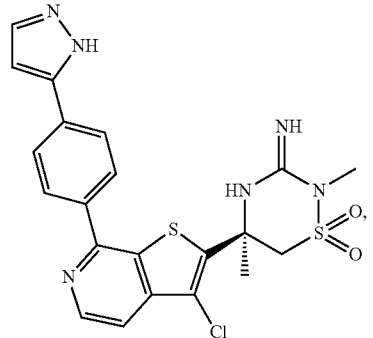 [SMILES: CN1C(=N)N[C@](C)(c2sc3c(-c4ccc(-c5ccn[nH]5)cc4)nccc3c2Cl)CS1(=O)=O] | 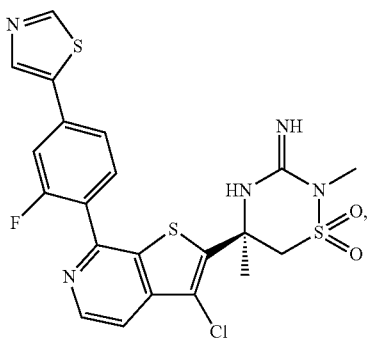 [SMILES: CN1C(=N)N[C@](C)(c2sc3c(-c4ccc(-c5cncs5)cc4F)nccc3c2Cl)CS1(=O)=O] |

| 177 -continued | 178 -continued |
|---|---|
| Example | Example |
| 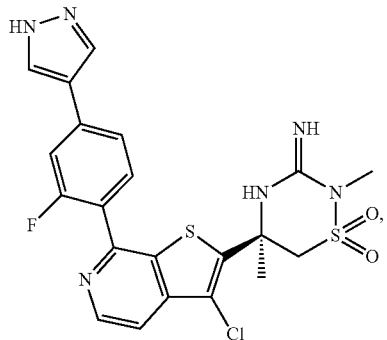 [SMILES: CN1C(=N)N[C@](C)(c2sc3c(-c4ccc(-c5cn[nH]c5)cc4F)nccc3c2Cl)CS1(=O)=O] | 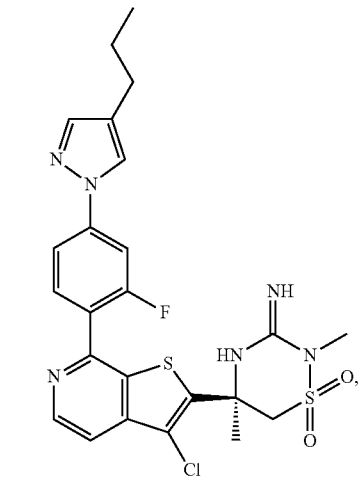 |
| 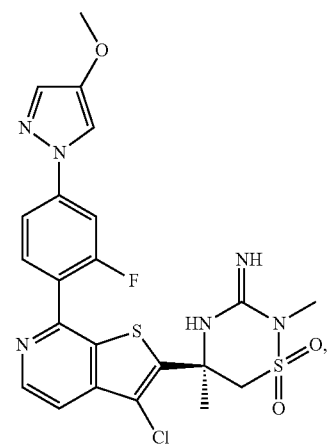 [SMILES: COc1cnn(-c2ccc(-c3nccc4c(Cl)c([C@]5(C)CS(=O)(=O)N(C)C(=N)N5)sc34)c(F)c2)c1] | 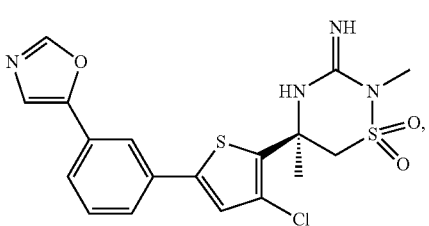 [SMILES: CN1C(=N)N[C@](C)(c2sc(-c3cccc(-c4cnco4)c3)cc2Cl)CS1(=O)=O] |
| | 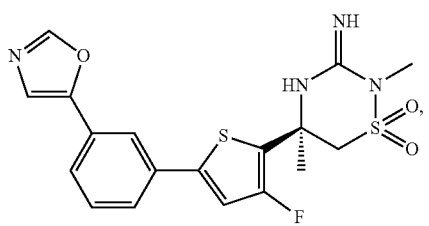 [SMILES: CN1C(=N)N[C@](C)(c2sc(-c3cccc(-c4cnco4)c3)cc2F)CS1(=O)=O] |
| 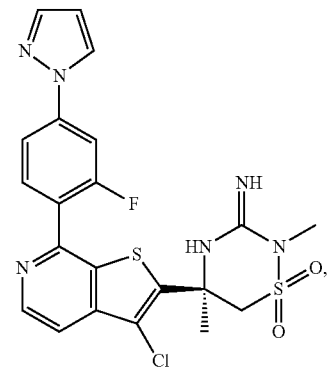 | 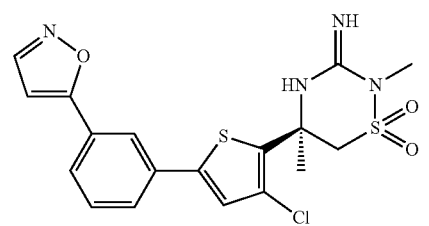 [SMILES: CN1C(=N)N[C@](C)(c2sc(-c3cccc(-c4ccno4)c3)cc2Cl)CS1(=O)=O] |
| | 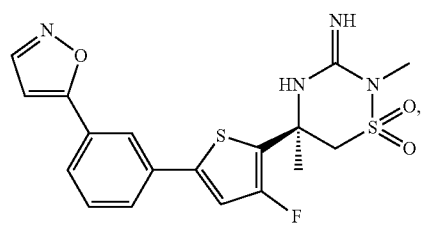 |

| Example |
|---|
| 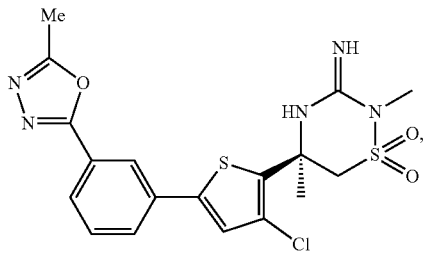 [SMILES: Cc1nnc(-c2cccc(-c3cc(Cl)c([C@]4(C)CS(=O)(=O)N(C)C(=N)N4)s3)c2)o1] |
| 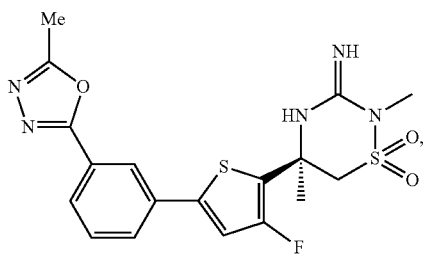 [SMILES: Cc1nnc(-c2cccc(-c3cc(F)c([C@]4(C)CS(=O)(=O)N(C)C(=N)N4)s3)c2)o1] |
| 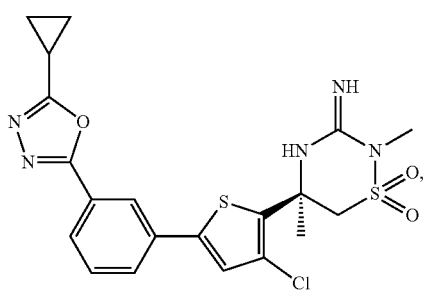 [SMILES: CN1C(=N)N[C@](C)(c2sc(-c3cccc(-c4nnc(C5CC5)o4)c3)cc2F)CS1(=O)=O] |
| 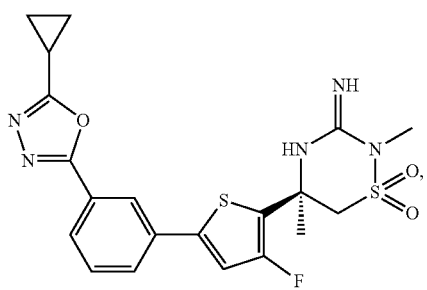 |
| 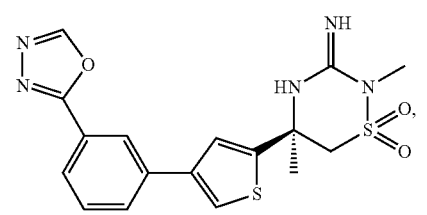 [SMILES: CN1C(=N)N[C@](C)(c2cc(-c3cccc(-c4nnco4)c3)cs2)CS1(=O)=O] |
| 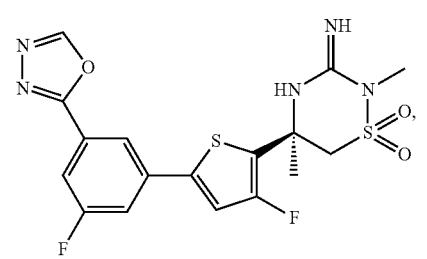 [SMILES: CN1C(=N)N[C@](C)(c2sc(-c3cc(F)cc(-c4nnco4)c3)cc2F)CS1(=O)=O] |
| Example |
|---|
| 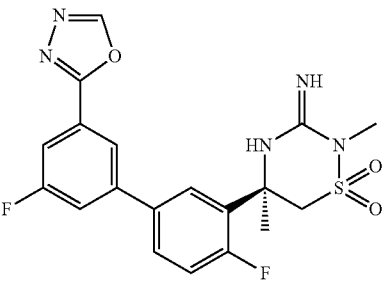 [SMILES: CN1C(=N)N[C@](C)(c2cc(-c3cc(F)cc(-c4nnco4)c3)ccc2F)CS1(=O)=O] |
| 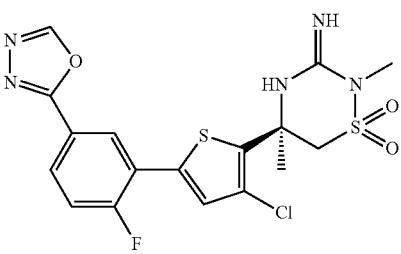 [SMILES: CN1C(=N)N[C@](C)(c2sc(-c3cc(-c4nnco4)ccc3F)cc2Cl)CS1(=O)=O] |
| 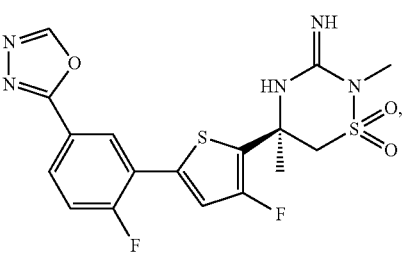 [SMILES: CN1C(=N)N[C@](C)(c2sc(-c3cc(-c4nnco4)ccc3F)cc2F)CS1(=O)=O] |
| 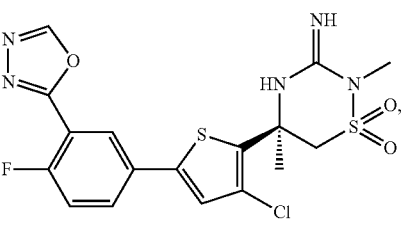 [SMILES: CN1C(=N)N[C@](C)(c2sc(-c3ccc(F)c(-c4nnco4)c3)cc2Cl)CS1(=O)=O] |
| 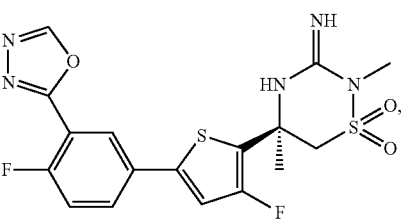 |
| 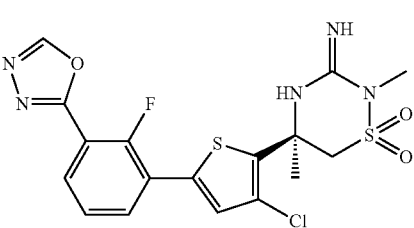 |

| 181 -continued | | 182 -continued | |
|---|---|---|---|
| Example | | Example | |
| 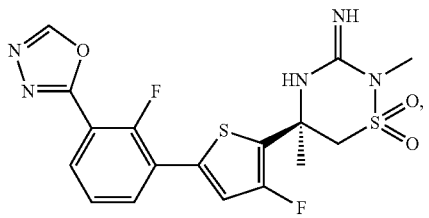 [SMILES: CN1C(=N)N[C@](C)(c2sc(-c3cccc(-c4nnco4)c3F)cc2F)CS1(=O)=O] | | 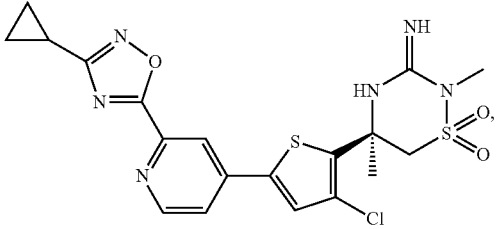 | |
| 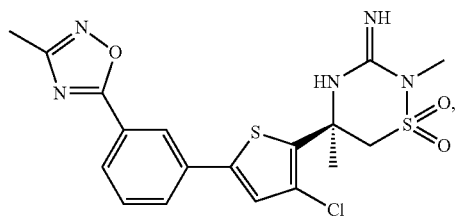 [SMILES: Cc1noc(-c2cccc(-c3cc(Cl)c([C@]4(C)CS(=O)(=O)N(C)C(=N)N4)s3)c2)n1] | | 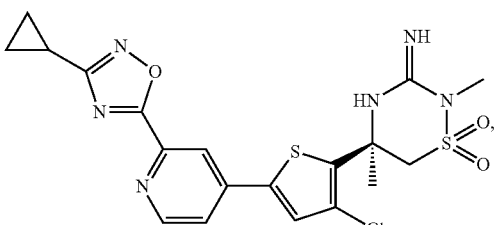 | |
| 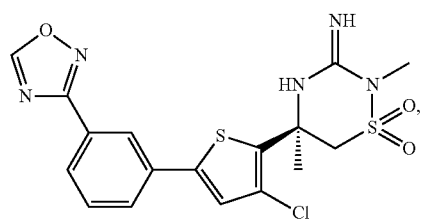 [SMILES: CN1C(=N)N[C@](C)(c2sc(-c3cccc(-c4ncon4)c3)cc2Cl)CS1(=O)=O] | | 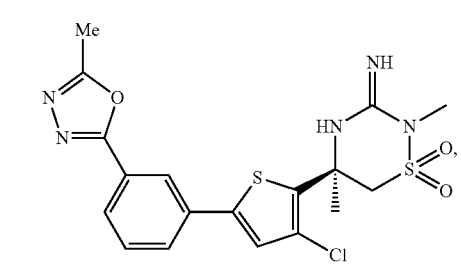 | |
| 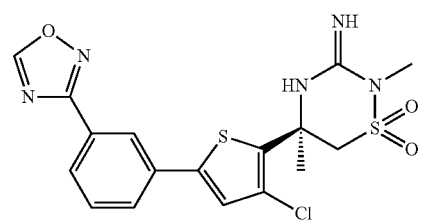 [SMILES: CN1C(=N)N[C@](C)(c2sc(-c3cccc(-c4ncon4)c3)cc2Cl)CS1(=O)=O] | | 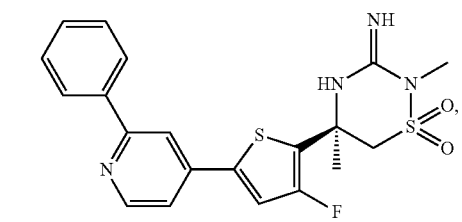 | |
| 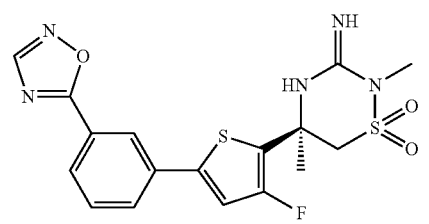 [SMILES: CN1C(=N)N[C@](C)(c2sc(-c3cccc(-c4ncno4)c3)cc2F)CS1(=O)=O] | | 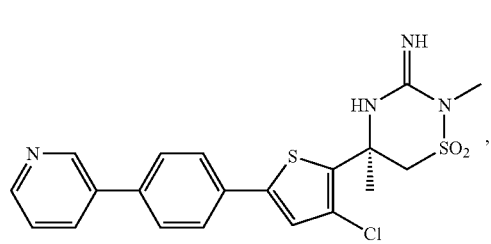 | |
| 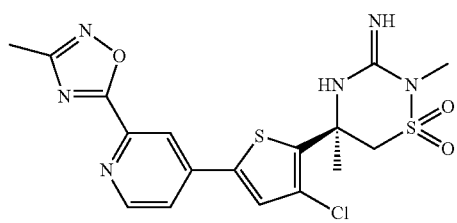 [SMILES: Cc1noc(-c2cc(-c3cc(Cl)c([C@]4(C)CS(=O)(=O)N(C)C(=N)N4)s3)ccn2)n1] | | 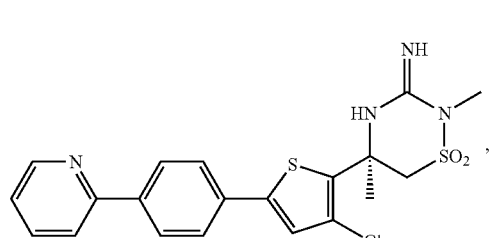 | |
| 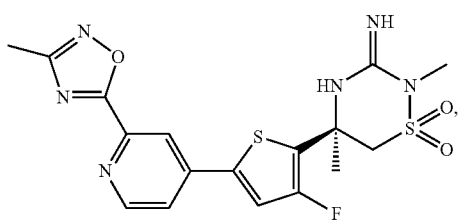 [SMILES: Cc1noc(-c2cc(-c3cc(F)c([C@]4(C)CS(=O)(=O)N(C)C(=N)N4)s3)ccn2)n1] | | 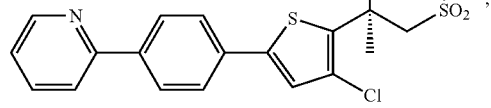 | |

| Example | Example |
|---|---|
| 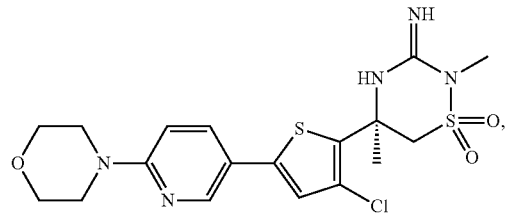 [SMILES: CN1C(=N)N[C@](C)(c2sc(-c3ccc(N4CCOCC4)nc3)cc2Cl)CS1(=O)=O] | 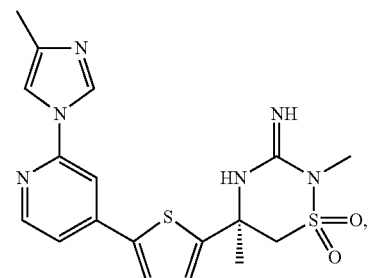 |
| 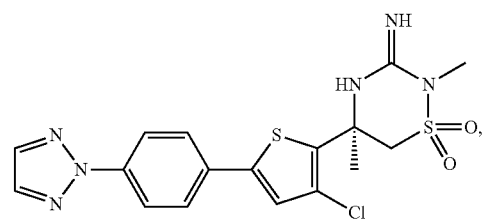 [SMILES: CN1C(=N)N[C@](C)(c2sc(-c3ccc(-n4nccn4)cc3)cc2Cl)CS1(=O)=O] | 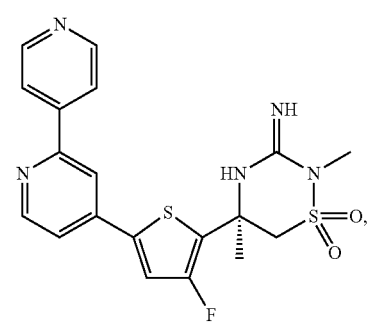 |
| 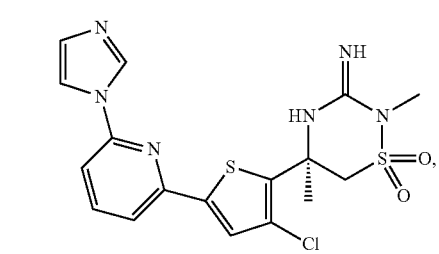 [SMILES: CN1C(=N)N[C@](C)(c2sc(-c3cccc(-n4ccnc4)n3)cc2Cl)CS1(=O)=O] | 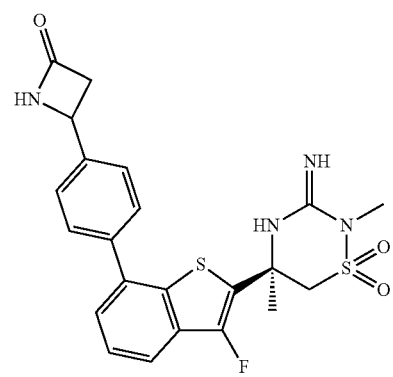 |
| 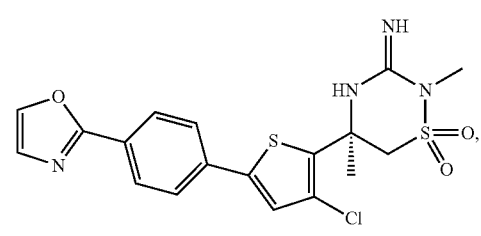 | 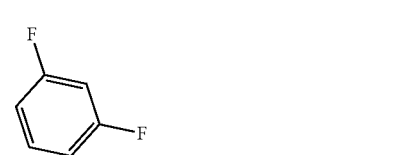 |
| 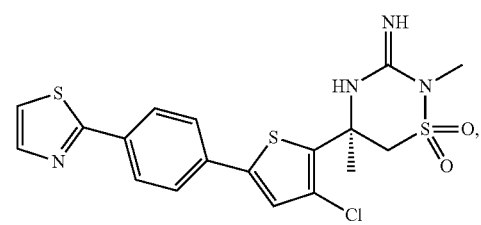 [SMILES: CN1C(=N)N[C@](C)(c2sc(-c3ccc(-c4nccs4)cc3)cc2Cl)CS1(=O)=O] | 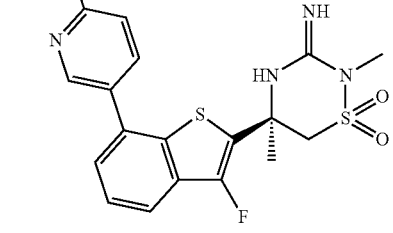 |
| 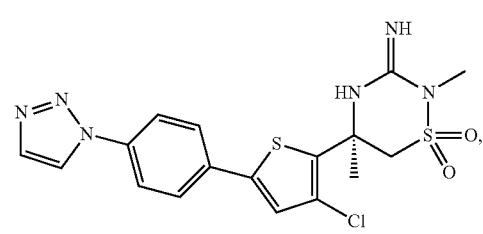 [SMILES: CN1C(=N)N[C@](C)(c2sc(-c3ccc(-n4ccnn4)cc3)cc2Cl)CS1(=O)=O] | |

-continued
Example
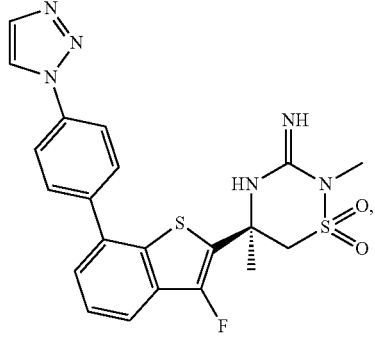 [SMILES: CN1C(=N)N[C@](C)(c2sc3c(-c4ccc(-n5ccnn5)cc4)cccc3c2F)CS1(=O)=O]
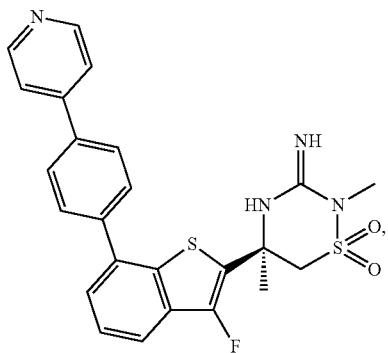 [SMILES: CN1C(=N)N[C@](C)(c2sc3c(-c4ccc(-c5ccncc5)cc4)cccc3c2F)CS1(=O)=O]
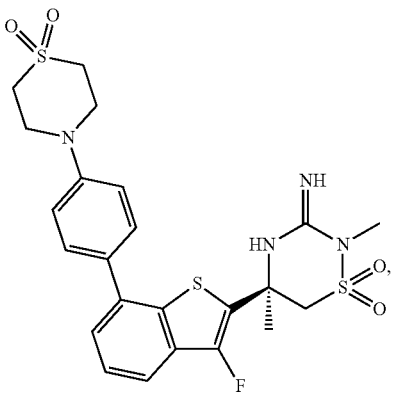 [SMILES: CN1C(=N)N[C@](C)(c2sc3c(-c4ccc(N5CCS(=O)(=O)CC5)cc4)cccc3c2F)CS1(=O)=O]
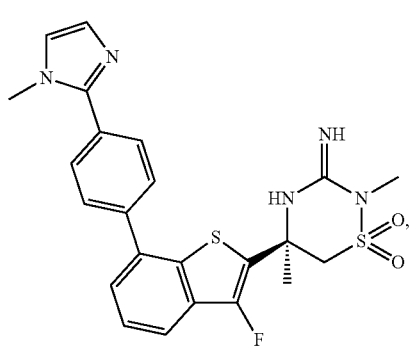 [SMILES: CN1C(=N)N[C@](C)(c2sc3c(-c4ccc(-c5nccn5C)cc4)cccc3c2F)CS1(=O)=O]
-continued
Example
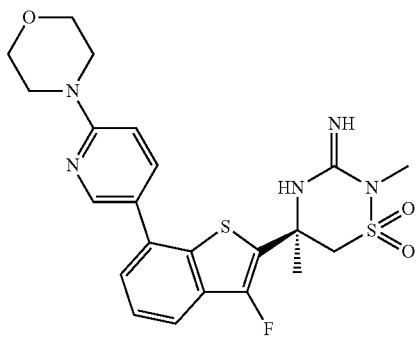 [SMILES: CN1C(=N)N[C@](C)(c2sc3c(-c4ccc(N5CCOCC5)nc4)cccc3c2F)CS1(=O)=O]
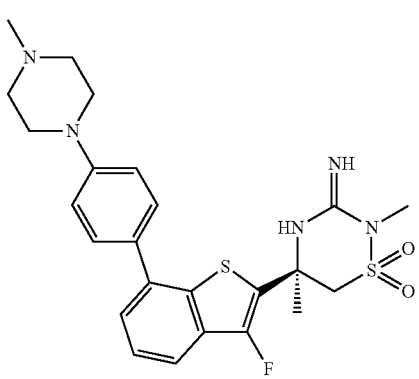 [SMILES: CN1CCN(c2ccc(-c3cccc4c(F)c([C@]5(C)CS(=O)(=O)N(C)C(=N)N5)sc34)cc2)CC1]
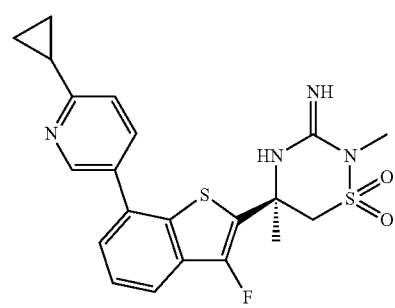 [SMILES: CN1C(=N)N[C@](C)(c2sc3c(-c4ccc(C5CC5)nc4)cccc3c2F)CS1(=O)=O]
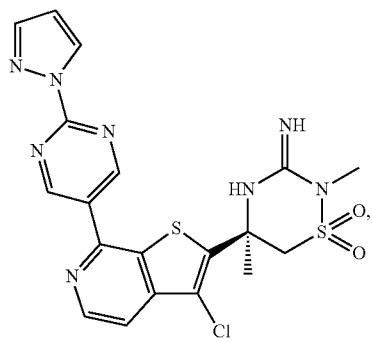 [SMILES: CN1C(=N)N[C@](C)(c2sc3c(-c4cnc(-n5cccn5)nc4)nccc3c2Cl)CS1(=O)=O]

| Example | Example |
|---|---|
| 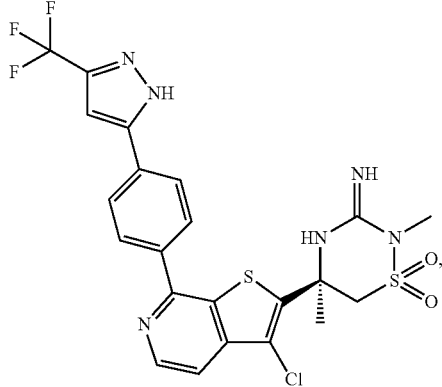 [SMILES: CN1C(=N)N[C@](C)(c2sc3c(-c4ccc(-c5cc(C(F)(F)F)n[nH]5)cc4)nccc3c2Cl)CS1(=O)=O] | 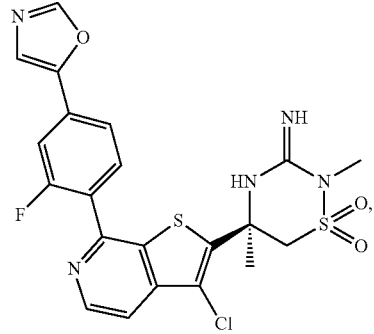 |
| 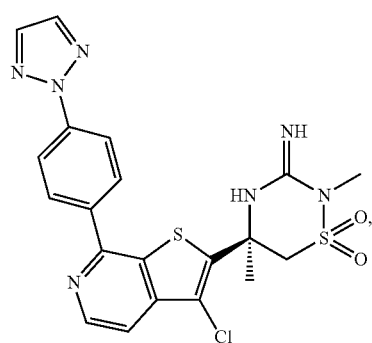 [SMILES: CN1C(=N)N[C@](C)(c2sc3c(-c4ccc(-n5nccn5)cc4)nccc3c2Cl)CS1(=O)=O] | 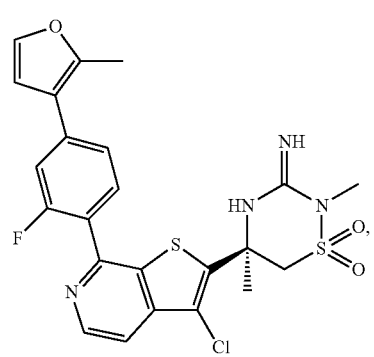 |
| 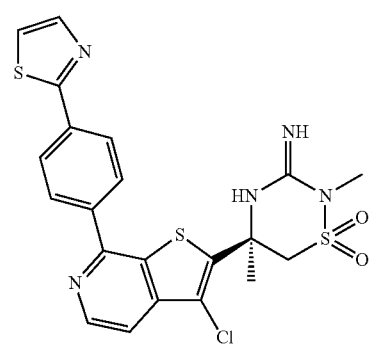 [SMILES: CN1C(=N)N[C@](C)(c2sc3c(-c4ccc(-c5nccs5)cc4)nccc3c2Cl)CS1(=O)=O] | 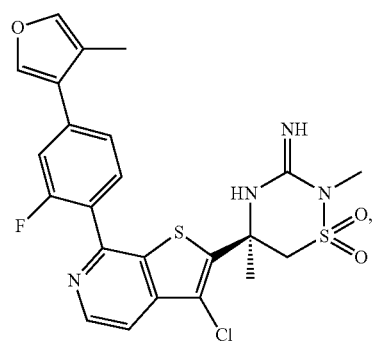 |
| 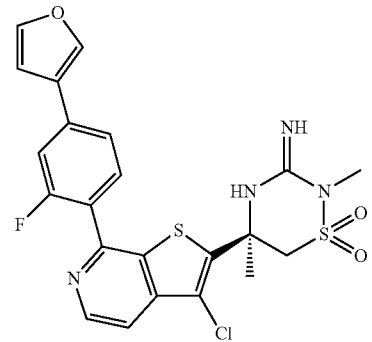 [SMILES: CN1C(=N)N[C@](C)(c2sc3c(-c4ccc(-c5ccoc5)cc4F)nccc3c2Cl)CS1(=O)=O] | 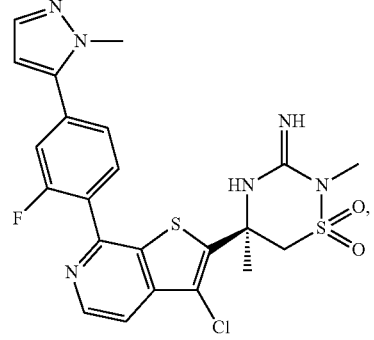 [SMILES: CN1C(=N)N[C@](C)(c2sc3c(-c4ccc(-c5ccnn5C)cc4F)nccc3c2Cl)CS1(=O)=O] |

189
-continued

| Example |
|---|
| 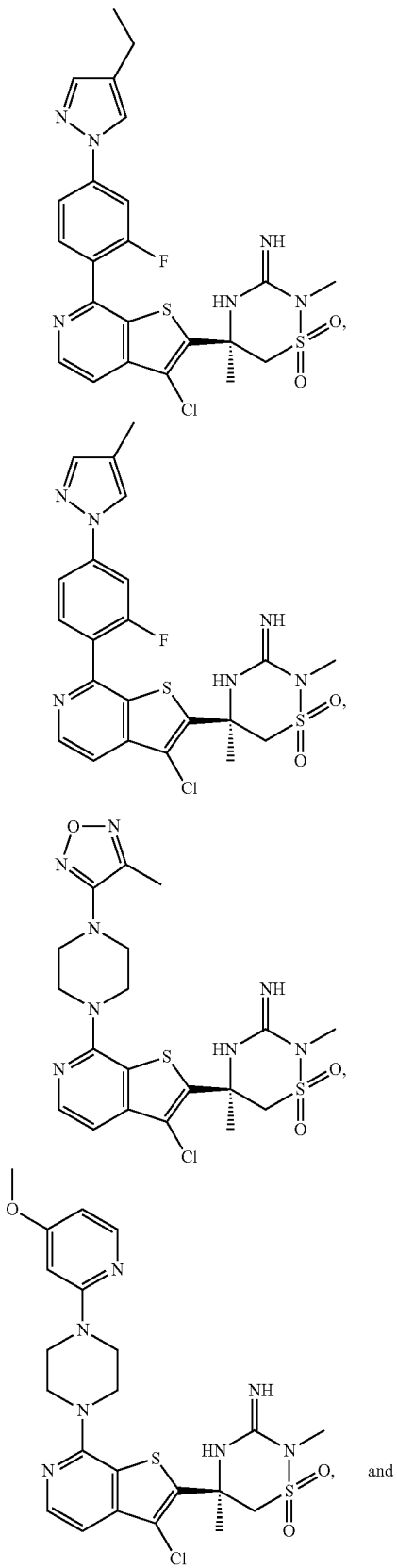 |

190
-continued

| Example |
|---|
| 5 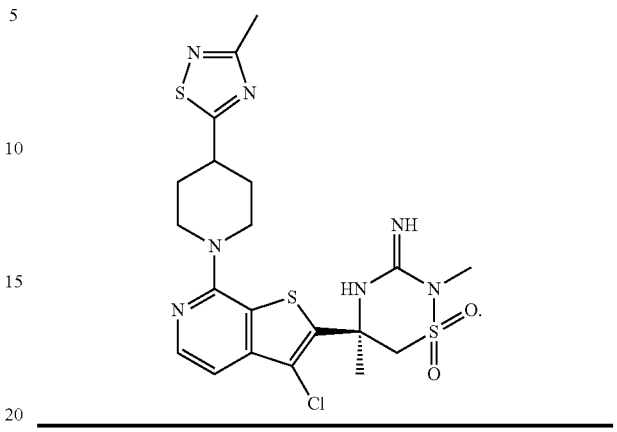 |

10. A pharmaceutical composition comprising a compound according to claim 1, or a tautomer thereof, or a stereoisomer of said compound or said tautomer, or a pharmaceutically acceptable salt thereof, and a pharmaceutically acceptable carrier or diluent.

11. A pharmaceutical composition of claim 10, wherein said at least one additional therapeutic agent is at least one agent selected from:
$m_1$ agonists; $m_2$ antagonists; cholinesterase inhibitors; galantamine; rivastigimine; N-methyl-D-aspartate receptor antagonists; combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies; vitamin E; nicotinic acetylcholine receptor agonists; CB1 receptor inverse agonists; CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors; Tau aggregation inhibitors; RAGE inhibitors; anti-Abeta vaccine; APP ligands; agents that upregulate insulin, cholesterol lowering agents; cholesterol absorption inhibitors; combinations of HMG-CoA reductase inhibitors and cholesterol absorption inhibitors; fibrates; combinations of fibrates and cholesterol lowering agents and/or cholesterol absorption inhibitors; nicotinic receptor agonists; niacin; combinations of niacin and cholesterol absorption inhibitors and/or cholesterol lowering agents; LXR agonists; LRP mimics; H3 receptor antagonists; histone deacetylase inhibitors; hsp90 inhibitors; 5-HT4 agonists; 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux; Metal-protein attenuating compound; GPR3 modulators; and antihistamines.

12. A method of treating and/or delaying the onset of a disease or pathology, wherein said disease or pathology is selected from Alzheimer's disease, Down's syndrome, Parkinson's disease, memory loss, memory loss associated with Alzheimer's disease, memory loss associated with Parkinson's disease, attention deficit symptoms, attention deficit and symptoms associated with Alzheimer's disease, Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, diabetes-associated amyloidogenesis, hemodialysis complications (from ($\beta_2$ microglobulins and complications arising therefrom in hemodialysis patients), scrapie, bovine spongiform encephalitis, traumatic brain injury ("TBI"), Creutzfeld-Jakob disease, and traumatic brain injury, said method comprising administering a compound according to claim 1, or a tautomer or stereoisomer thereof, or a pharmaceutically acceptable salt thereof, to a patient in need thereof in an amount effective to treat said disease or pathology.

13. A method of claim 12, wherein said Aβ pathology is Alzheimer's disease.

\* \* \* \* \*